(12) United States Patent
Kolczewski et al.

(10) Patent No.: US 9,067,911 B2
(45) Date of Patent: Jun. 30, 2015

(54) PIPERIDINE DERIVATIVES

(71) Applicant: Hoffmann-La Roche Inc., Nutley, NJ (US)

(72) Inventors: Sabine Kolczewski, Loerrach (DE); Emmanuel Pinard, Linsdorf (FR); Henri Stalder, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 87 days.

(21) Appl. No.: 13/766,840

(22) Filed: Feb. 14, 2013

(65) Prior Publication Data

US 2013/0158050 A1 Jun. 20, 2013

Related U.S. Application Data

(63) Continuation of application No. 12/690,128, filed on Jan. 20, 2010, now abandoned.

(30) Foreign Application Priority Data

Jan. 27, 2009 (EP) .................................. 09151382

(51) Int. Cl.
| | |
|---|---|
| *C07D 211/56* | (2006.01) |
| *A61K 31/451* | (2006.01) |
| *C07D 407/04* | (2006.01) |
| *C07D 401/04* | (2006.01) |
| *C07D 401/12* | (2006.01) |
| *C07D 405/04* | (2006.01) |
| *C07D 417/10* | (2006.01) |
| *C07D 213/56* | (2006.01) |
| *C07D 221/20* | (2006.01) |

(52) U.S. Cl.
CPC ............ *C07D 407/04* (2013.01); *A61K 31/451* (2013.01); *C07D 211/56* (2013.01); *C07D 401/04* (2013.01); *C07D 401/12* (2013.01); *C07D 405/04* (2013.01); *C07D 417/10* (2013.01); *C07D 213/56* (2013.01); *C07D 221/20* (2013.01)

(58) Field of Classification Search
CPC ............................ C07D 211/56; A61K 31/451
See application file for complete search history.

(56) References Cited

U.S. PATENT DOCUMENTS

| 7,259,157 B2 | 8/2007 | Liverton et al. |
| 2010/0056497 A1 | 3/2010 | Nakahira et al. |

FOREIGN PATENT DOCUMENTS

| DE | 2600557 | 7/1977 |
| WO | 01/81308 | 11/2001 |
| WO | 2005/037782 | 4/2005 |
| WO | 2005/037792 | 4/2005 |
| WO | 2005/040166 | 5/2005 |
| WO | 2008/093737 | 8/2008 |
| WO | 2010/086251 | 8/2010 |

OTHER PUBLICATIONS

Lim "Synthesis and biological evaluation of 3-amino-4-aryl-piperidine derivatives as BACE 1 inhibitors." Bulletin of the Korean Chemical Society, 2006 27(9), 1371-1376.*
Lopez-Corcuera et al., "Mol. Mem. Biol." 18:13-20 ( 2001).
International Search Report for PCT/EP2010/050551 dated Apr. 12, 2010.
Chen et al., "J. Neurophysiol." 89(2):691-703 ( 2003).
Vandenberg et al., "Exp. Opin. Ther. Targets" 5(4):507-518 ( 2001).
Javitt et al., "Biol. Psychiatry" 45:668-679 ( 1999).
Sharma et al., "Br. J. Psychiatry" ((Suppl. 28)), 174:44-51 ( 1999).
Pralong et al., "Prog. in Neurobiol." 67:173-202 ( 2002).
Mohn et al., "Cell" 98:427-436 ( 1999).
Bliss et al., "Nature" 361:31-39 ( 1993).
Carlsson, M. L., "J. Neural Transm." 105:525-535 ( 1998).
Armer et al., "Exp. Opin. Ther. Patents" 11(4):563-572 ( 2001).
(Chilean Off Act Search Report in Corres Chilean App 17902011 Jul. 17, 2012).
Lewis et al., "Neuron" 28:325-333 ( 2000).
Nakazoto et al., "Exp. Opin. Ther. Patents" 10(1):75-98 ( 2000).
Tang et al., "Nature" 401:63-69 ( 1999).
Gainetdinov et al., "Trends in Pharm. Sci." 23(8):367-373 ( 2002).
Bergereon et al., "Proc. Natl. Acad. Sci. USA" 95:15730-15734 ( 1998).

* cited by examiner

*Primary Examiner* — David K O Dell

(57) ABSTRACT

The present invention relates to a compound of formula I

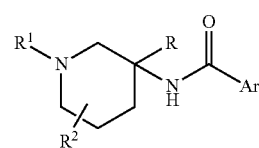

wherein $R^1$, $R^2$, and Ar are as defined herein or to a pharmaceutically acceptable acid addition salt, to a racemic mixture, or to its corresponding enantiomer and/or optical isomer thereof. These compounds and their pharmaceutical compositions are useful in the treatment of neurological and neuropsychiatric disorders.

17 Claims, No Drawings

PIPERIDINE DERIVATIVES

PRIORITY TO RELATED APPLICATION(S)

This application is a continuation application of U.S. Ser. No. 12/690,128, filed Jan. 20, 2010, which claims the benefit of European Patent Application No. 09151382.0, filed Jan. 27, 2009, which are hereby incorporated by reference in their entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 2000, 28:325-33). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 2001, 5(4): 507-518; Nakazato A and Okuyama S, et al., 2000, Exp. Opin. Ther. Patents, 10(1): 75-98). This pharmacological approach poorly address negative and cognitive symptoms which are the best predictors of functional outcome (Sharma T., Br. J. Psychiatry, 1999, 174(suppl. 28): 44-51).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., 1999, Biol. Psychiatry, 45: 668-679 and refs. herein). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., 1999, Cell, 98: 427-236).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Hebb D O, 1949, The organization of behavior, Wiley, NY; Bliss T V and Collingridge G L, 1993, Nature, 361: 31-39). Transgenic mice overexpressing the NMDA NR2B subunit exhibit enhanced synaptic plasticity and superior ability in learning and memory (Tang J P et al., 1999, Nature: 401-63-69).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, 2002, Trends in Pharm. Sci., 23(8): 367-373).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., 2001, Mol. Mem. Biol., 18: 13-20). Thus, one strategy to enhance NMDA receptor activity is to elevate the glycine concentration in the local microenvironment of synaptic NMDA receptors by inhibition of GlyT-1 transporter (Bergereon R. Et al., 1998, Proc. Natl. Acad. Sci. USA, 95: 15730-15734; Chen L et al., 2003, J. Neurophysiol., 89 (2): 691-703).

Glycine transporters inhibitors are suitable for the treatment of neuroligical and neuropsychiatric disorders. The majority of diseases states implicated are psychoses, schizophrenia (Armer R E and Miller D J, 2001, Exp. Opin. Ther. Patents, 11 (4): 563-572), psychotic mood disorders such as severe major depressive disorder, mood disorders associated with psychotic disorders such as acute mania or depression associated with bipolar disorders and mood disorders associated with schizophrenia, (Pralong E T et al., 2002, Prog. Neurobiol., 67: 173-202), autistic disorders (Carlsson M L, 1998, J. Neural Transm. 105: 525-535), cognitive disorders such as dementias, including age related dementia and senile dementia of the Alzheimer type, memory disorders in a mammal, including a human, attention deficit disorders and pain (Armer R E and Miller D J, 2001, Exp. Opin. Ther. Patents, 11 (4): 563-572).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides a compound of formula I

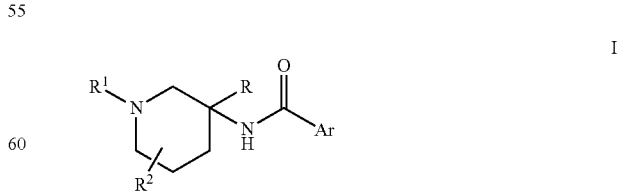

wherein
$R^1$ is hydrogen, lower alkyl, $CD_3$, —$(CH_2)$, —CHO, —$(CH_2)_n$—O-lower alkyl, —$(CH_2)_n$—OH, —$(CH_2)_n$-cycloalkyl or heterocycloalkyl;

$R^2$ is hydrogen, halogen, hydroxy, lower alkyl, di-lower alkyl, —OCH$_2$—O-lower alkyl, or lower alkoxy; or the piperidin ring together with $R^2$ forms 4-aza-spiro[2.5]oct-6-yl;

Ar is aryl or heteroaryl, each of which is optionally substituted by one, two or three substituents selected from halogen, lower alkyl, lower alkyl substituted by halogen, lower alkoxy substituted by halogen, cycloalkyl, lower alkoxy, S-lower alkyl, heteroaryl, heterocycloalkyl, or and phenyl optionally substituted by R';

R' is halogen, lower alkyl, lower alkoxy, lower alkoxy substituted by halogen, or heteroaryl;

R is lower alkyl, cycloalkyl, heterocycloalkyl, aryl or heteroaryl, wherein aryl and heteroaryl are each optionally substituted by one or two R'; and n is 0, 1 2 or 3;

or a pharmaceutically acceptable acid addition salt, a racemic mixture, or its corresponding enantiomer and/or optical isomer thereof.

Furthermore, the invention includes all racemic mixtures, all their corresponding enantiomers and/or optical isomers.

The present invention provides pharmaceutical compositions containing the compounds of formula I or pharmaceutically acceptable acid addition salts thereof. The invention also provides methods for the manufacture of the compounds and compositions of the invention.

Compounds of formula I are good inhibitors of the glycine transporter 1 (GlyT-1) and have a good selectivity to glycine transporter 2 (GlyT-2) inhibitors. As such, the compounds of the invention are useful for the treatment of diseases related to activation of NMDA receptors via Glyt-1 inhibition. The invention provides methods for the treatment of neurological and neuropsychiatric disorders, for example psychoses, dysfunction in memory and learning, schizophrenia, dementia and other diseases in which cognitive processes are impaired, such as attention deficit disorders or Alzheimer's disease.

The preferred indications using the compounds of the present invention are schizophrenia, cognitive impairment and Alzheimer's disease.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a lower alkyl group as defined above, which is linked through an O atom.

The term "cycloalkyl" denotes a saturated or partially saturated ring containing from 3 to 7 carbon atoms, for example cyclopropyl, cyclobutyl, cyclopentyl, cyclopentenyl, cyclohexyl, cyclohexenyl, cycloheptyl or cycloheptenyl. Preferred cycloalkyl rings are cyclopropyl and cyclopentyl.

The term "heterocycloalkyl" denotes a saturated or partially saturated ring containing from 3 to 6 ring atoms, wherein at least one ring atom is a heteroatom selected from N, S and O, with the rest of the ring atoms being carbon, for example piperazinyl, pyrrolidinyl, oxetanyl, morpholinyl piperidinyl, or tetrahydropyranyl.

The term "halogen" denotes chlorine, iodine, fluorine and bromine.

The term "aryl" denotes a monovalent cyclic aromatic hydrocarbon radical consisting of one or more fused rings in which at least one ring is aromatic in nature, for example phenyl or naphthyl.

The term "lower alkyl substituted by halogen" denotes a lower alkyl group as defined above, wherein at least one hydrogen atom is replaced by a halogen atom, for example the following groups: $CF_3$, $CHF_2$, $CH_2F$, $CH_2CF_3$, $CH_2CHF_2$, $CH_2CH_2F$, $CH_2CH_2CF_3$, $CH_2CH_2CH_2CF_3$, $CH_2CH_2Cl$, $CH_2CF_2CF_3$, $CH_2CF_2CHF_2$, $CF_2CHFCF_3$, $C(CH_3)_2CF_3$, $CH(CH_3)CF_3$ or $CH(CH_2F)CH_2F$.

The term "lower alkoxy substituted by halogen" denotes an alkoxy group as defined above, wherein at least one hydrogen atom is replaced by halogen as defined above.

The term "heteroaryl" denotes a cyclic aromatic radical consisting of one or more fused rings containing 5-14 ring atoms, preferably containing 5-10 ring atoms, in which at least one ring is aromatic in nature, and which contains at least one heteroatom, selected from N, O and S, for example quinoxalinyl, dihydroisoquinolinyl, pyrazinyl, pyridazinyl, pyrazolyl, pyridinyl, pyridyl, pyrimidinyl, oxadiazolyl, triazolyl, tetrazolyl, thiazolyl, thiadiazolyl, thienyl, furyl, imidazolyl, benzofuranyl, dihydrobenzofuranyl and benzo[1,3]dioxole. Preferred heteroaryl group is pyridinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

Preferred compounds of formula I are those, wherein $R^1$ is lower alkyl and Ar and R are phenyl.

Especially preferred are compounds, wherein the phenyl group for Ar is substituted by at least two $CF_3$ groups, for example the following compounds:

rac-2-fluoro-N-(1-methyl-3-phenyl-piperidin-3-yl)-4,6-bis-trifluoromethyl-benzamide;

rac-2-methoxy-N-(1-methyl-3-phenyl-piperidin-3-yl)-4,6-bis-trifluoromethyl-benzamide;

rac-2-ethyl-N-(1-methyl-3-phenyl-piperidin-3-yl)-4,6-bis-trifluoromethyl-benzamide;

rac-N-[3-(4-fluoro-phenyl)-1-methyl-piperidin-3-yl]-2-methoxy-4,6-bis-trifluoromethyl-benzamide; and 2-methoxy-N—((R)-1-methyl-3-phenyl-piperidin-3-yl)-4,6-bis-trifluoromethyl-benzamide.

Further preferred are compounds, wherein the phenyl group for Ar is substituted by at least one $CF_3$ group, for example the following compounds:

rac-2-ethyl-N-(1-methyl-3-phenyl-piperidin-3-yl)-4-trifluoromethyl-benzamide;

rac-2-bromo-6-methoxy-N-(1-methyl-3-phenyl-piperidin-3-yl)-4-trifluoromethyl-benzamide;

rac-N-(1,2-dimethyl-3-phenyl-piperidin-3-yl)-2-methoxy-6-methylsulfanyl-4-trifluoromethyl-benzamide;

rac-2-cyclopropyl-N-(1-methyl-3-phenyl-piperidin-3-yl)-4-trifluoromethyl-benzamide;

rac-2-methoxy-N-(1-methyl-3-phenyl-piperidin-3-yl)-6-methylsulfanyl-4-trifluoromethyl-benzamide;

rac-N-(1-methyl-3-phenyl-piperidin-3-yl)-2-methylsulfa-
nyl-4-trifluoromethyl-benzamide;
rac-N-[3-(4-fluoro-phenyl)-1-methyl-piperidin-3-yl]-2-
methoxy-6-methylsulfanyl-4-trifluoromethyl-benzamide;
rac-N-[3-(4-chloro-phenyl)-1-methyl-piperidin-3-yl]-2-
methoxy-6-methylsulfanyl-4-trifluoromethyl-benzamide;
2-methoxy-N—((S)-1-methyl-3-phenyl-piperidin-3-yl)-6-
methylsulfanyl-4-trifluoromethyl-benzamide;
2-methoxy-N—((R)-1-methyl-3-phenyl-piperidin-3-yl)-6-
methylsulfanyl-4-trifluoromethyl-benzamide;
rac-2-difluoromethoxy-N-(1-methyl-3-phenyl-piperidin-3-
yl)-4-trifluoromethyl-benzamide;
rac-N-[3-(3-chloro-phenyl)-1-methyl-piperidin-3-yl]-2-
methoxy-6-methylsulfanyl-4-trifluoromethyl-benzamide;
rac-2-methoxy-N-[3-(4-methoxy-phenyl)-1-methyl-piperi-
din-3-yl]-6-methylsulfanyl-4-trifluoromethyl-benzamide;
rac-N-(5-fluoro-1-methyl-3-phenyl-piperidin-3-yl)-2-meth-
oxy-6-methylsulfanyl-4-trifluoromethyl-benzamide;
rac-N-(1-isopropyl-3-phenyl-piperidin-3-yl)-2-methoxy-6-
methylsulfanyl-4-trifluoromethyl-benzamide;
2-cyclopropyl-N—((S)-1-methyl-3-phenyl-piperidin-3-yl)-
4-trifluoromethyl-benzamide;
2-cyclopropyl-N—((R)-1-methyl-3-phenyl-piperidin-3-yl)-
4-trifluoromethyl-benzamide;
rac-2-cyclobutyl-N-(1-methyl-3-phenyl-piperidin-3-yl)-4-
trifluoromethyl-benzamide;
rac-N-[3-(2,4-difluoro-phenyl)-1-methyl-piperidin-3-yl]-2-
methoxy-6-methylsulfanyl-4-trifluoromethyl-benzamide;
rac-N-[3-(2-fluoro-phenyl)-1-methyl-piperidin-3-yl]-2-
methoxy-6-methylsulfanyl-4-trifluoromethyl-benzamide;
rac-N-[3-(2,5-difluoro-phenyl)-1-methyl-piperidin-3-yl]-2-
methoxy-6-methylsulfanyl-4-trifluoromethyl-benzamide;
rac-2-isopropyl-N-(1-methyl-3-phenyl-piperidin-3-yl)-4-tri-
fluoromethyl-benzamide;
rac-2-methoxy-6-methylsulfanyl-N-(1-methyl-1,4,5,6-tet-
rahydro-2H-[3,4']bipyridinyl-3-yl)-4-trifluoromethyl-
benzamide;
rac-2-ethyl-N-(1-methyl-1,4,5,6-tetrahydro-2H-[3,4]bipy-
ridinyl-3-yl)-4-trifluoromethyl-benzamide;
rac-2-methoxy-6-methylsulfanyl-N-(1-methyl-1,4,5,6-tet-
rahydro-2H-[3,3']bipyridinyl-3-yl)-4-trifluoromethyl-
benzamide;
rac-2-Ethyl-N-(1-methyl-1,4,5,6-tetrahydro-2H-[3,3']bipy-
ridinyl-3-yl)-4-trifluoromethyl-benzamide hydrochloride;
2-methoxy-N-((3RS,5SR)-5-methoxy-1-methyl-3-phenyl-
piperidin-3-yl)-6-methylsulfanyl-4-trifluoromethyl-ben-
zamide;
2-cyclopropyl-N-((3RS,5SR)-5-methoxy-1-methyl-3-phe-
nyl-piperidin-3-yl)-4-trifluoromethyl-benzamide;
2-ethyl-N-((3RS,5SR)-5-methoxy-1-methyl-3-phenyl-pip-
eridin-3-yl)-4-trifluoromethyl-benzamide;
rac-2,6-dimethoxy-N-(1-methyl-3-phenyl-piperidin-3-yl)-4-
trifluoromethyl-benzamide;
2-cyclopropyl-N-((3RS,5SR)-1,5-dimethyl-3-phenyl-pip-
eridin-3-yl)-4-trifluoromethyl-benzamide;
rac-2-cyclopropyl-4-trifluoromethyl-N-(1,5,5-trimethyl-3-
phenyl-piperidin-3-yl)-benzamide;
rac-2-methoxy-6-methylsulfanyl-4-trifluoromethyl-N-(1,6,
6-trimethyl-3-phenyl-piperidin-3-yl)-benzamide;
N-((3RS,5SR)-1,5-dimethyl-3-phenyl-piperidin-3-yl)-2-
methoxy-6-methylsulfanyl-4-trifluoromethyl-benzamide;
2-methoxy-N-((3RS,5SR)-5-methoxymethoxy-1-methyl-3-
phenyl-piperidin-3-yl)-6-methylsulfanyl-4-trifluorom-
ethyl-benzamide;
rac-N-[3-(3-bromo-phenyl)-1-methyl-piperidin-3-yl]-2-
methoxy-6-methylsulfanyl-4-trifluoromethyl-benzamide;
rac-N-[3-(2-chloro-4-fluoro-phenyl)-1-methyl-piperidin-3-
yl]-2-methoxy-6-methylsulfanyl-4-trifluoromethyl-ben-
zamide;
rac-2-methoxy-6-methylsulfanyl-N-[1-methyl-3-(3-trifluo-
romethyl-phenyl)-piperidin-3-yl]-4-trifluoromethyl-ben-
zamide;
rac-2-methoxy-N-[3-(3-methoxy-phenyl)-1-methyl-piperi-
din-3-yl]-6-methylsulfanyl-4-trifluoromethyl-benzamide;
rac-N-[3-(3-fluoro-phenyl)-1-methyl-piperidin-3-yl]-2-
methoxy-6-methylsulfanyl-4-trifluoromethyl-benzamide;
rac-N-[3-(3-chloro-4-fluoro-phenyl)-1-methyl-piperidin-3-
yl]-2-methoxy-6-methylsulfanyl-4-trifluoromethyl-ben-
zamide
rac-N-[3-(3,4-difluoro-phenyl)-1-methyl-piperidin-3-yl]-2-
methoxy-6-methylsulfanyl-4-trifluoromethyl-benzamide;
rac-2-methoxy-6-methylsulfanyl-N-(1-methyl-3-m-tolyl-pi-
peridin-3-yl)-4-trifluoromethyl-benzamide;
rac-N-[3-(4-fluoro-3-methyl-phenyl)-1-methyl-piperidin-3-
yl]-2-methoxy-6-methylsulfanyl-4-trifluoromethyl-ben-
zamide;
rac-N-[3-(3,5-difluoro-phenyl)-1-methyl-piperidin-3-yl]-2-
methoxy-6-methylsulfanyl-4-trifluoromethyl-benzamide;
rac-2-methoxy-6-methylsulfanyl-4-trifluoromethyl-N-(1,5,
5-trimethyl-3-phenyl-piperidin-3-yl)-benzamide;
rac-2-ethyl-3-methyl-N-(1-methyl-3-phenyl-piperidin-3-
yl)-4-trifluoromethyl-benzamide;
rac-N-(1-tert-butyl-3-phenyl-piperidin-3-yl)-2-methoxy-6-
methylsulfanyl-4-trifluoromethyl-benzamide;
rac-2-methoxy-N-(4-methyl-6-phenyl-4-aza-spiro[2.5]oct-
6-yl)-6-methylsulfanyl-4-trifluoromethyl-benzamide;
N-((3R,5S) or (3S,5R)-5-hydroxy-1-methyl-3-phenyl-pip-
eridin-3-yl)-2-methoxy-6-methylsulfanyl-4-trifluorom-
ethyl-benzamide;
2-methoxy-N-((3R,5S) or (3S,5R)-5-methoxy-1-methyl-3-
phenyl-piperidin-3-yl)-6-methylsulfanyl-4-trifluorom-
ethyl-benzamide;
2-methoxy-N-((3S,5R) or (3R,5S)-5-methoxy-1-methyl-3-
phenyl-piperidin-3-yl)-6-methylsulfanyl-4-trifluorom-
ethyl-benzamide;
N—[(R or S)-3-(2-fluoro-phenyl)-1-methyl-piperidin-3-yl]-
2-methoxy-6-methylsulfanyl-4-trifluoromethyl-benza-
mide;
N—[(R or S)-3-(2,5-difluoro-phenyl)-1-methyl-piperidin-3-
yl]-2-methoxy-6-methylsulfanyl-4-trifluoromethyl-ben-
zamide;
2-ethyl-N—((R or S)-1-methyl-3-phenyl-piperidin-3-yl)-4-
trifluoromethyl-benzamide;
2-methoxy-6-methylsulfanyl-4-trifluoromethyl-N—((S or
R)-1,5,5-trimethyl-3-phenyl-piperidin-3-yl)-benzamide;
N-((3S,6S) or (3R,6R)-1,6-dimethyl-3-phenyl-piperidin-3-
yl)-2-methoxy-6-methylsulfanyl-4-trifluoromethyl-ben-
zamide;
N-((3R,6R) or (3S,6S)-1,6-dimethyl-3-phenyl-piperidin-3-
yl)-2-methoxy-6-methylsulfanyl-4-trifluoromethyl-ben-
zamide;
N-((3R,6S) or (3S,6R)-1,6-dimethyl-3-phenyl-piperidin-3-
yl)-2-methoxy-6-methylsulfanyl-4-trifluoromethyl-ben-
zamide;
N-((3S,5R) or (3R,5S)-1,5-dimethyl-3-phenyl-piperidin-3-
yl)-2-methoxy-6-methylsulfanyl-4-trifluoromethyl-ben-
zamide;
N-((3R,5S) or (3S,5R)-1,5-dimethyl-3-phenyl-piperidin-3-
yl)-2-ethyl-4-trifluoromethyl-benzamide;
2-ethyl-N-((3R,5S) or (3S,5R)-5-methoxy-1-methyl-3-phe-
nyl-piperidin-3-yl)-4-trifluoromethyl-benzamide;
2-cyclopropyl-N-((3R,5S) or (3S,5R)-5-methoxy-1-methyl-
3-phenyl-piperidin-3-yl)-4-trifluoromethyl-benzamide;
and
2,6-Dimethoxy-N—(R or (S)-1-methyl-3-phenyl-piperidin-
3-yl)-4-trifluoromethyl-benzamide.

Preferred compounds of formula I are those, wherein R¹ is cycloalkyl or heterocycloalkyl and Ar and R are phenyl, for example
rac-N-(1-cyclopentyl-3-phenyl-piperidin-3-yl)-2-methoxy-4,6-bis-trifluoromethyl-benzamide;
rac-N-(1-cyclopropylmethyl-3-phenyl-piperidin-3-yl)-2-methoxy-4,6-bis-trifluoromethyl-benzamide; and
rac-2-methoxy-N-[3-phenyl-1-(tetrahydro-pyran-4-yl)-piperidin-3-yl]-4,6-bis-trifluoromethyl-benzamide.

Preferred compounds of formula I are those, wherein R¹ is lower alkyl, Ar is phenyl and R is heteroaryl, for example
rac-N-(5-fluoro-1'-methyl-1',4',5',6'-tetrahydro-2'H-[2,3']bipyridinyl-3'-yl)-2-methoxy-6-methylsulfanyl-4-trifluoromethyl-benzamide;
rac-2-methoxy-6-methylsulfanyl-N-(1-methyl-1,4,5,6-tetrahydro-2H-[3,4]bipyridinyl-3-yl)-4-trifluoromethyl-benzamide;
rac-2-ethyl-N-(1-methyl-1,4,5,6-tetrahydro-2H-[3,4']bipyridinyl-3-yl)-4-trifluoromethyl-benzamide hydrochloride;
rac-2-methoxy-6-methylsulfanyl-N-(1-methyl-1,4,5,6-tetrahydro-2H-[3,3']bipyridinyl-3-yl)-4-trifluoromethyl-benzamide; and
rac-2-ethyl-N-(1-methyl-1,4,5,6-tetrahydro-2H-[3,3']bipyridinyl-3-yl)-4-trifluoromethyl-benzamide.

Preferred compounds of formula I are those, wherein R¹ is hydrogen and Ar and R are phenyl, for example, rac-2-cyclopropyl-N-(3-phenyl-piperidin-3-yl)-4-trifluoromethyl-benzamide.

Preferred compounds of formula I are those, wherein R² is hydroxy, for example
rac-N-(5-hydroxy-1-methyl-3-phenyl-piperidin-3-yl)-2-methoxy-6-methylsulfanyl-4-trifluoromethyl-benzamide and
N-((3R,5S) or (3S,5R)-5-hydroxy-1-methyl-3-phenyl-piperidin-3-yl)-2-methoxy-6-methylsulfanyl-4-trifluoromethyl-benzamide.

Preferred compounds of formula I are those, wherein R² is halogen, for example
rac-N-(5-fluoro-1-methyl-3-phenyl-piperidin-3-yl)-2-methoxy-6-methylsulfanyl-4-trifluoromethyl-benzamide.

Preferred compounds of formula I are those, wherein R¹ is $CD_3$, for example the following compound [2H-methyl]-2-methoxy-N—(R) or (S)-1-methyl-3-phenyl-piperidin-3-yl)-6-methylsulfanyl-4-trifluoromethyl-benzamide hydrochloride.

The present compounds of formula I and their pharmaceutically acceptable salts can be prepared by methods known in the art, for example, by processes described below, which process comprises
a) reacting a compound of formula

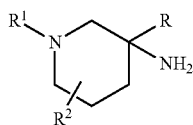

II with a compound of formula

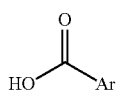

III in the presence of an activating agent such as HATU (o-(7-azabenzotriazol-1-yl)-1,1,3,3-tetramethyluronium hexafluorophosphate) or thionyl chloride to obtain a compound of formula

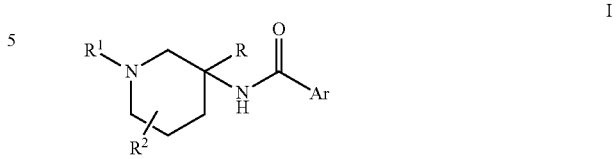

I wherein the substituents are as defined above, or
b) reacting a compound of formula

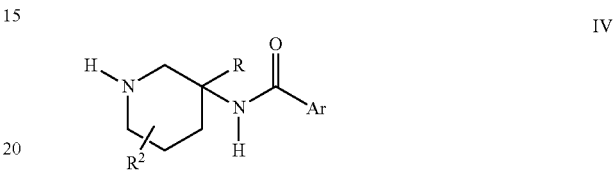

IV with a compound of formula

R¹X in the presence of base like N-ethyldiisopropylamine to obtain a compound of formula

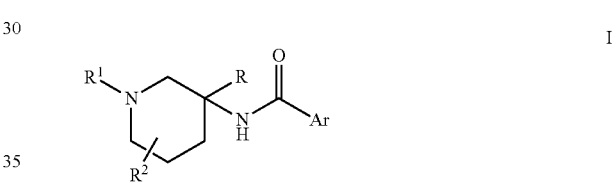

I wherein X is halogen and the other substituents are as defined above, or
c) reacting a compound of formula

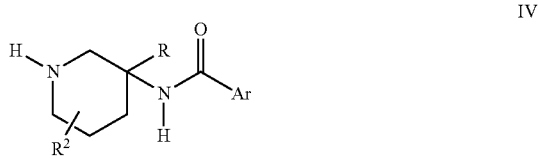

IV with a carbonyl reagent of formula $R^4$—C(O)—$R^5$, in the presence of a reducing agent like sodium cyanoborohydride to obtain a compound of formula

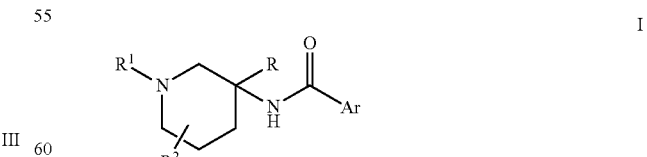

I wherein the substituents are as defined above, $R^4$ and $R^5$ are lower alkyl or form together with the carbon atom to which they are attached a cycloalkyl or heterocycloalkyl group, and if desired, converting the compounds obtained into pharmaceutically acceptable acid addition salts.

The compounds of formula I can be prepared in accordance with process variant a) or b) or c) and with the following schemes 1-12. The starting material is commercially available or can be prepared in accordance with known methods.

agent like Raney Nickel under an atmosphere of hydrogen or like Zinc in the presence of acid like hydrochloride acid to provide amino-piperidone derivatives XIII which can be reduced to II in the presence of reducing agent like lithium Scheme 1

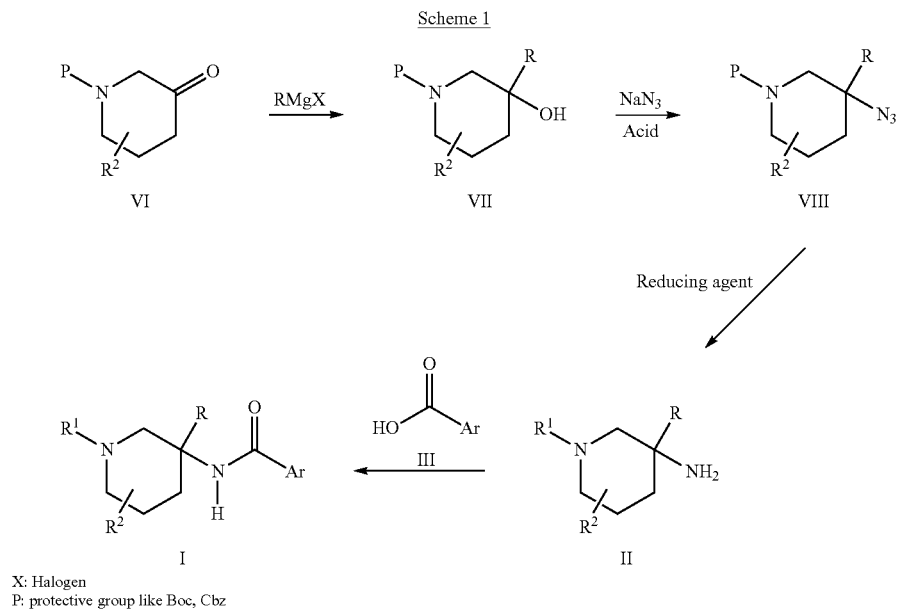

X: Halogen
P: protective group like Boc, Cbz

Compounds of general formula I can be prepared by reacting piperidine derivatives of formula II with acid of formula III in the presence of an activating agent like HATU (o-(7-azabenzotriazol-1-yl)-1,1,3,3-tetramethyluronium hexafluorophosphate) or thionyl chloride. Piperidine derivatives of formula II can be prepared by reacting piperidone derivative VI with an organometallic reagent like a Grignard to provide alcohol VII followed by a treatment with sodium azide in the presence of an acid like TFA to provide azide derivative VIII which is transformed into II in the presence of a reducing agent like lithium aluminium hydride.

aluminium hydride. Nitro-piperidone derivatives XII can be prepared from nitro derivatives XI according to an intramolecular Mannich type reaction performed in the presence of an amine: $R^1NH_2$ and an aldehyde like formaldehyde. XI can be prepared by Michael addition of nitro-methyl-aryl derivatives IX onto methyl acrylate in the presence of base like Amberlyst A21 or Triton B or by reacting aryl halide derivatives X with methyl 4-nitrobutyrate in the presence of Palla- Scheme 2

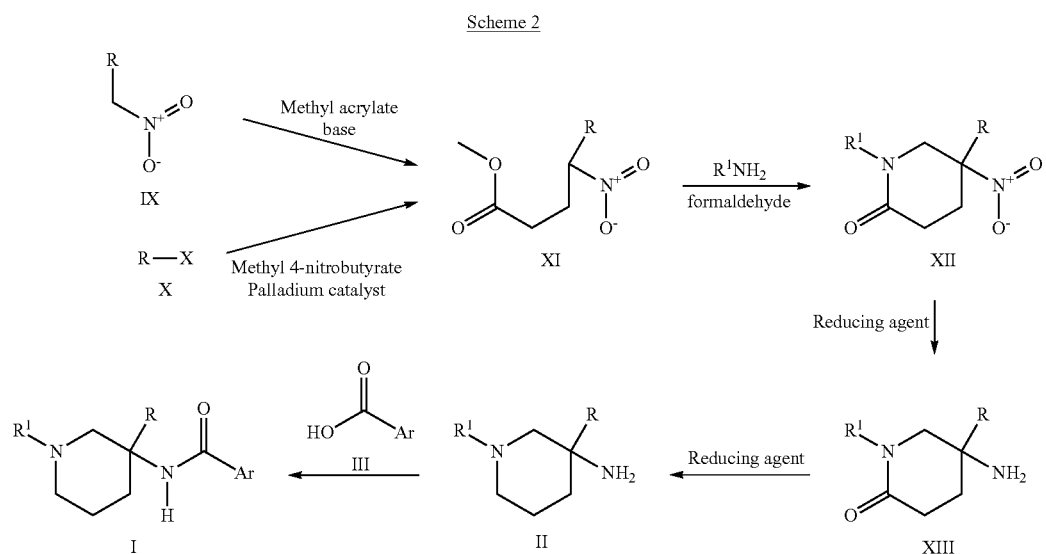

Alternatively, piperidine derivatives of formula II in which $R^2$ is hydrogen can be prepared from nitro-piperidone derivatives XII after reduction of the nitro group with reducing dium catalyst like $Pd_2dba_3$, ligand like 2-(di-t-butylphosphino)-2'-methybiphenyl and base like cesium carbonate as described by Buchwald et al. in J. Org. Chem. 2002, 106.

Scheme 3

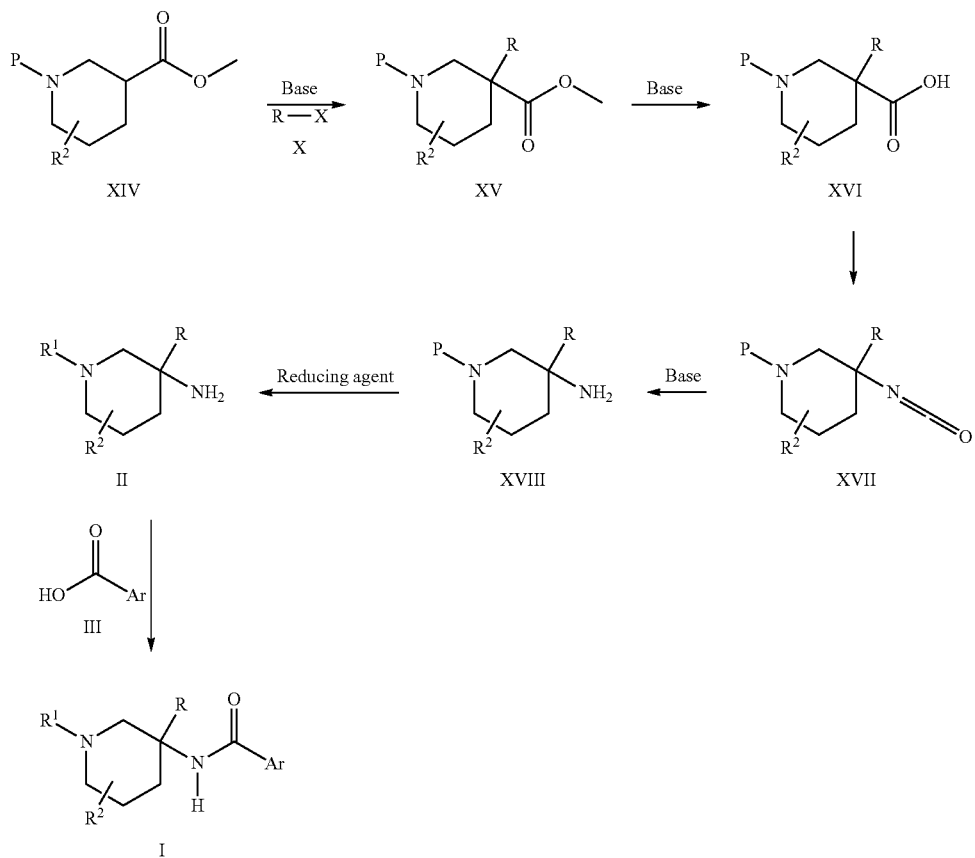

P: protective group like: Boc
X: Halogen

Alternatively, piperidine derivatives of formula II in which R is an alkyl group can be prepared from acid XVI after a Curtius rearrangement in the presence of a reagent like DPPA (diphenylphosphoryl azide) to provide isocyanate XVII which is then hydrolyzed in presence of base like sodium hydroxide to lead to protected piperidine XVIII that is reduced in II in a presence of a reducing agent like lithium aluminiumhydride. Acid XVI can be prepared from ester XIV after treatment with a base like lithium diisopropylamide and an alkylating agent R—X to provide intermediate ester XV which is then saponified to XVI in the presence of base like lithium hydroxide.

Scheme 4

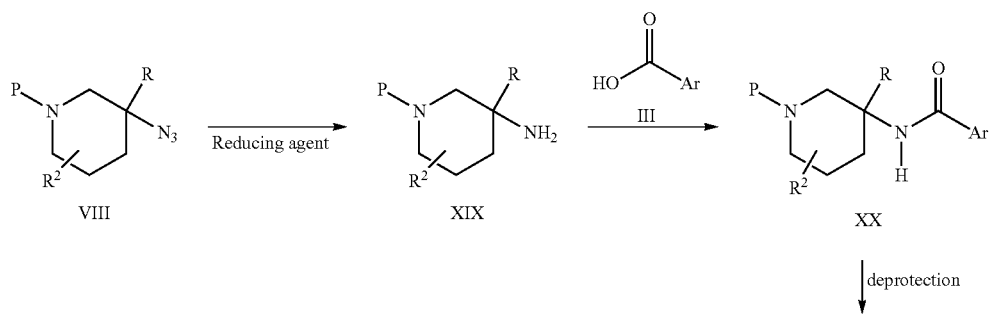

-continued

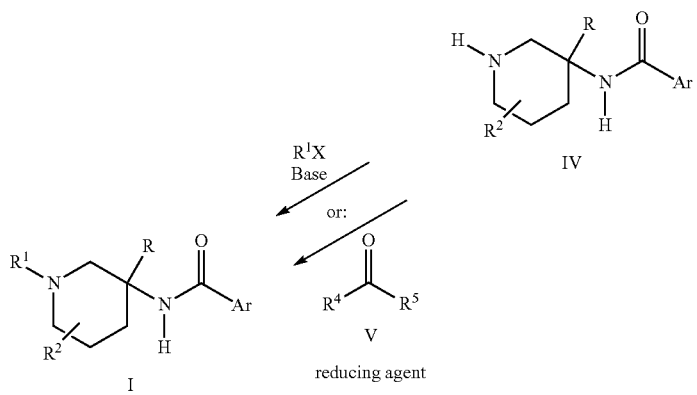

P: protective group like Cbz
X: halogen

The substituents are as described above, $R^4$ and $R^5$ are lower alkyl or form together with the carbon atom to which they are attached a cycloalkyl or heterocycloalkyl group.

Alternatively, compounds of general formula I can be prepared by reaction of piperidine derivative IV with either an alkylating agent $R^1X$ in the presence of base like N-ethyldiisopropylamine or with a carbonyl reagent V in the presence of a reducing agent like sodium cyanoborohydride. Piperidine derivative IV can be prepared after reduction of azide VIII with reagent like sodium borohydride to provide amine derivative XIX which can be then coupled with acid III in the presence of an activating agent like HATU or thionyl chloride to yield amide derivative XX which is then transformed into IV after cleavage of the N-protective group.

Scheme 5

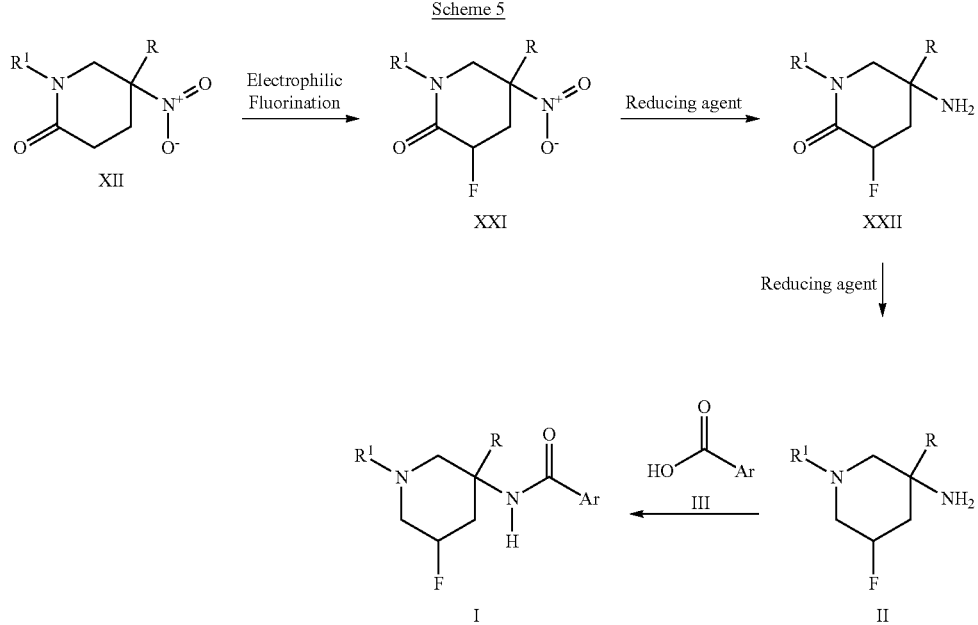

Alternatively, piperidine derivatives of formula II in which R² is fluorine can be prepared from fluorinated nitro piperidone XXI after two consecutive reductions. The first reduction uses an agent like Raney Nickel, and the second reduction uss an agent like lithium aluminiumhydride. XXI can be prepared by reaction of nitro piperidine XII with a base like lithium diisopropylamine followed by treatment with an electrophilic fluorinating agent like N-fluorobenzenesulphonimide.

Alternatively, piperidine derivatives of formula II which contains two geminal alkyl group R² can be prepared from bis-alkylated nitro piperidone XXV after two consecutive reductions. The first reduction uses an agent like Raney Nickel, and the second reduction uses an agent like lithium aluminiumhydride. XXV can be prepared by reaction of mono-alkylated nitro piperidine XXIII with a base like lithium diisopropylamine in the presence of TMEDA (tetramethylethylenediamine) followed by treatment with an electrophilic alkylating agent like R²X where X is an halogen.

Scheme 6

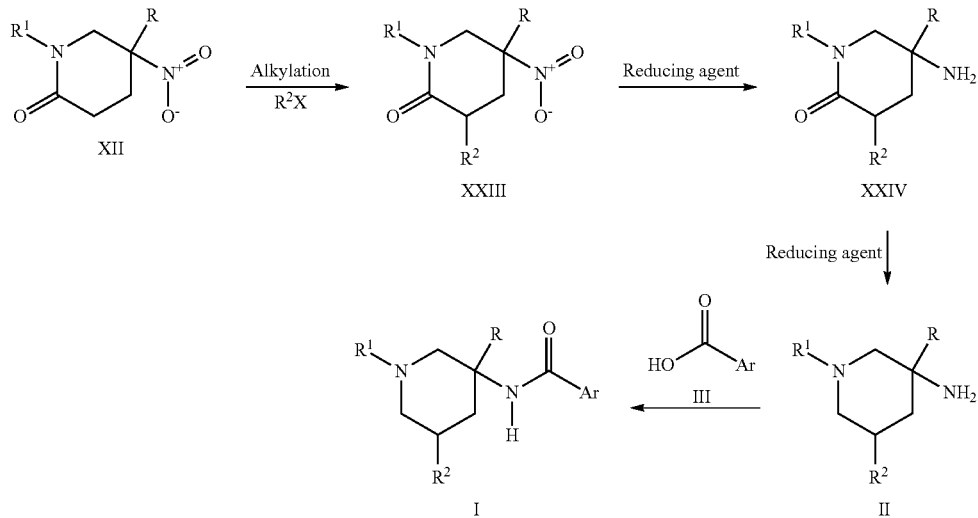

Alternatively, piperidine derivatives of formula II in which R² is alkyl can be prepared from alkylated nitro piperidone XXIII after two consecutive reductions. The first reduction uses an agent like Raney Nickel, and the second reduction uses an agent like lithium aluminiumhydride. XXIII can be prepared by reaction of nitro piperidine XII with a base like lithium diisopropylamine followed by treatment with an electrophilic alkylating agent like R²X where X is a halogen.

Scheme 7

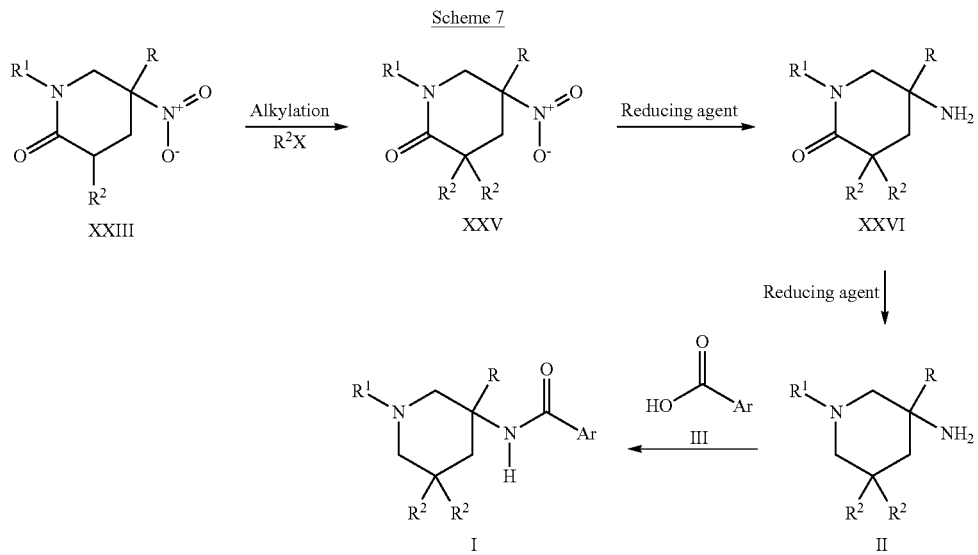

Scheme 8

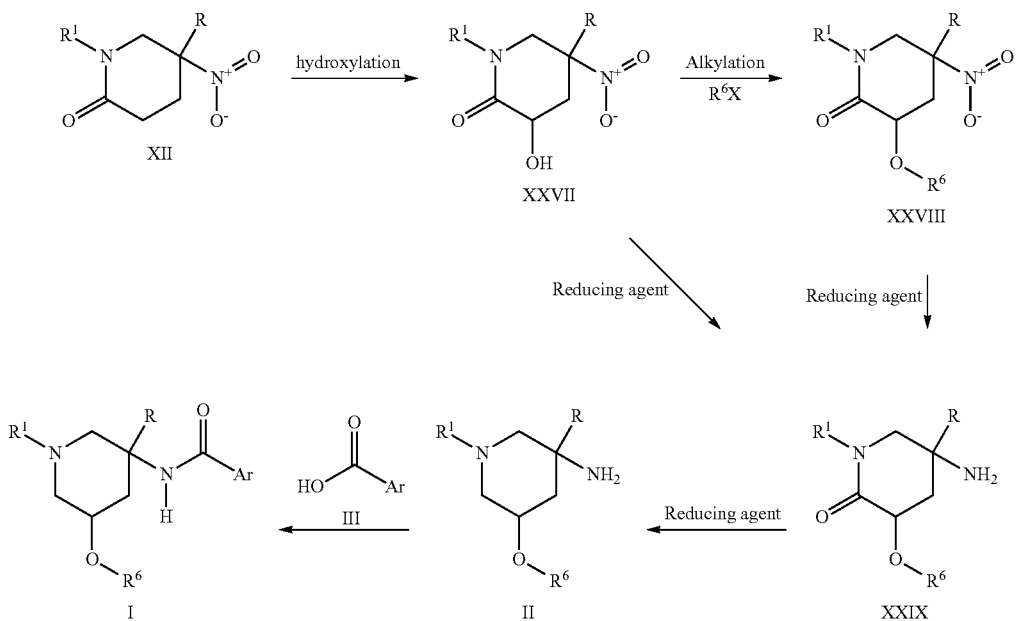

Alternatively, piperidine derivatives of formula II in which $R^2$ is a hydroxyl ($R^6$=H) or an alkoxy group ($R^6$=Alkyl) can be prepared from hydroxy nitro piperidone XXVII or alkoxy nitro piperidone XXVIII after two consecutive reductions. The first reduction uses an agent like Raney Nickel, and the second reduction uses an agent like lithium aluminiumhydride. XXVIII can be prepared from XXVII by reaction with a base like sodium hydride and an electrophilic alkylating agent like $R^6X$ where X is a halogen. XXVII can be prepared by reaction of nitro piperidine XII with a base like lithium diisopropylamine followed by treatment with an electrophilic hydroxylating agent like (oxodiperoxy(pyridine) (1,3-dimethyl-3,4,5,6-tetrahydro-2(1H)-pyrimidone)molybdenum (IV)) or bis(trimethylsilyl)peroxide.

Scheme 9

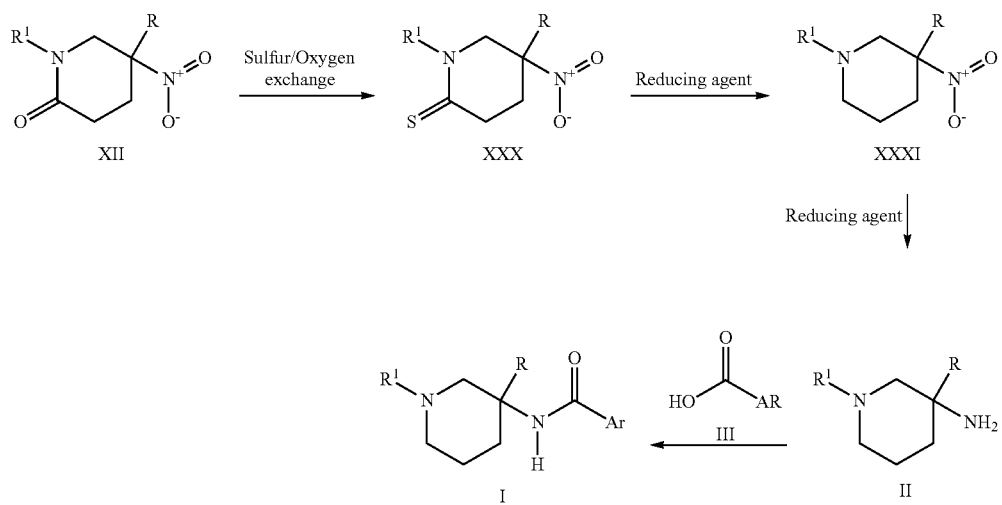

Alternatively, piperidine derivatives of formula II in which R is an heteroaryl group like pyridine can be prepared from nitro piperidine thione XXX after two consecutive reductions The first reduction uses an agent like sodium borohydride, and the second reduction uses an agent like Raney Nickel. XXX can be prepared from nitro piperidinone XXII by reaction with Lawesson's reagent.

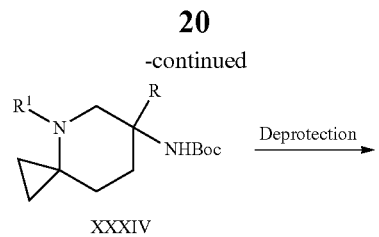

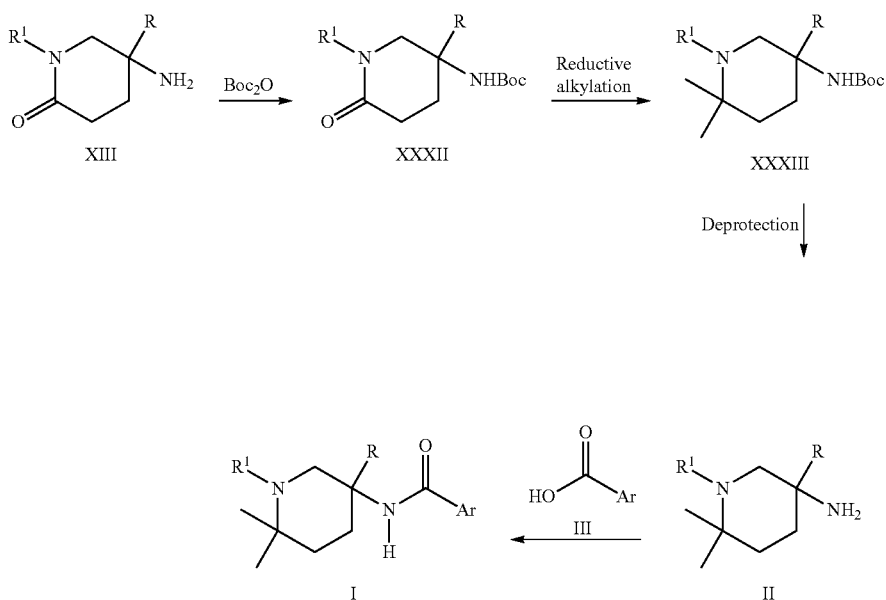

Alternatively, piperidine derivatives of formula II which contains two geminal methyl groups can be prepared from Boc-protected amino piperidinone XXXII after reaction with methylmagnesium bromide and Zirconium (IV) chloride followed by cleavage of the Boc group under acidic condition. XXXII can be prepared after reaction of amino piperidone XIII with di-tert-butyl dicarbonate.

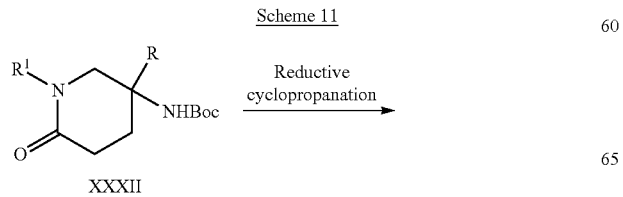

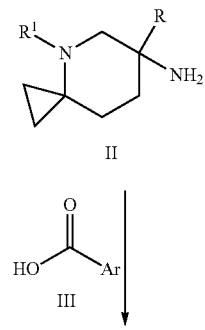

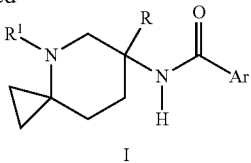

Alternatively, piperidine derivatives of formula II which contains a cyclopropyl unit can be prepared from Boc-protected amino piperidinone XXXII after reaction with ethyl magnesium bromide and titanium isopropoxide followed by cleavage of the Boc group under acidic condition.

base such as sodium or potassium hydroxide, potassium carbonate, sodium bicarbonate, ammonia, and the like.

EXPERIMENTAL PART

Abbreviations
HATU O-(7-azabenzotriazol-1-yl)-1,1,3,3-tetramethyluronium hexafluorophosphate
DMF Dimethylformamide
DMSO Dimethylsulfoxide
THF Tetrahydrofuran
TMEDA Tetramethylethylenediamine

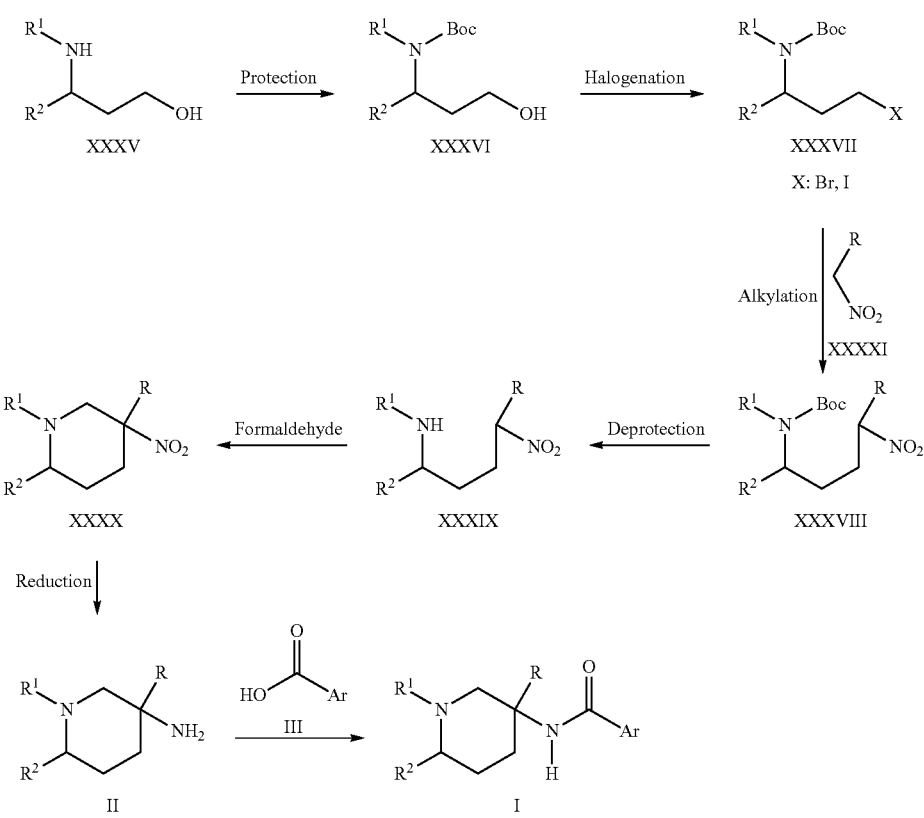

Scheme 12

Alternatively, piperidine derivatives of formula II in which $R^2$ is an alkyl group can be prepared from nitro derivative XXXIX following an intramolecular Mannich reaction performed in the presence of an aldehyde like formaldehyde to provide nitro piperidine XXXX which is then treated with a reducing agent like Raney Nickel. XXXIX can be obtained by deprotection of Boc-protected nitro derivative XXXVIII which can be prepared by reaction of nitro derivative XXXXI with halogenated compound XXXVII in the presence of a base like n-butyl lithium. XXXVII can be obtained after protection and halogenation of amino alcohol XXXV.

Racemic mixtures of chiral compound I can be separated using chiral HPLC.

The acid addition salts of the basic compounds of formula I can be converted to the corresponding free bases by treatment with at least a stoichiometric equivalent of a suitable Preparation of Intermediates Example A.1

Preparation of rac-1-Methyl-3-phenyl-piperidin-3-ylamine

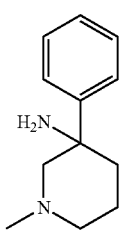

a) step 1:
rac-3-Hydroxy-3-phenyl-piperidine-1-carboxylic acid benzyl ester

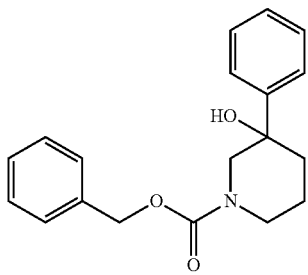 [SMILES: O=C(OCc1ccccc1)N1CCCC(O)(c2ccccc2)C1]

To a solution of 9 ml (9 mmol) phenylmagnesium bromide (1M solution in THF) in THF (13 ml) was added a solution of 1.5 g (6.00 mmol) 3-oxo-piperidine-1-carboxylic acid benzyl ester (commercial) in THF (5 ml) at room temperature over a period of 15 minutes. The mixture was stirred for 30 minutes and then quenched under ice bath cooling with a 20% ammonium chloride solution (4 ml). The organic layer was decanted and the residue was extracted once with ethyl acetate. The combined organic layers were dried over sodium sulfate, filtered and concentrated in vacuo. The crude oil was purified on silica gel (Eluent: Heptane/ethyl acetate 0 to 50%) to provide 0.55 g (30%) of the title compound as a white solid. MS (m/e): 312.0 (M+H+)

a) step 2:
rac-3-Azido-3-phenyl-piperidine-1-carboxylic acid benzyl ester

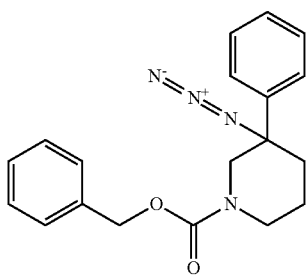 [SMILES: [N-]=[N+]=NC1(c2ccccc2)CCCN(C(=O)OCc2ccccc2)C1]

g (3.212 mmol) 3-Hydroxy-3-phenyl-piperidine-1-carboxylic acid benzyl ester was dissolved in a cold mixture (10° C.) of trifluoroacetic acid (12.3 ml) and water (2.0 ml). The solution was cooled to 0° C. and 1.46 g (22.48 mmol) sodium azide were added portionwise. The temperature rose to 10° C. The ice bath was removed and the mixture was stirred at room temperature for 3 hours. The mixture was cooled in an ice bath and basified by dropwise addition of a 25% ammonium hydroxide solution (13.0 ml) maintaining the temperature below 20° C. The mixture was diluted with water (45 ml) and extracted 3 times with dichloromethane. The combined extracts were washed once with brine, dried over sodium sulfate, filtered and concentrated in vacuo to provide the title compound as a light yellow oil which was used in the next step without further purification.

a) step 3:
rac-1-Methyl-3-phenyl-piperidin-3-ylamine

To a suspension of 126 mg (3.15 mmol) LiAlH4 in THF (2.7 ml) at temperature below 10° C. was added dropwise a solution of 530 mg (1.576 mmol) rac-3-azido-3-phenyl-piperidine-1-carboxylic acid benzyl ester in THF (5.3 ml). The ice bath was removed. The temperature rose to 35° C. The mixture was then heated in a 65° C. oil bath for 1 hour. The mixture was cooled to 0° C. Water (125 ul), NaOH 5N (125 ul) and finally water (0.375 ml) were added dropwise maintaining the temperature below 10° C. The mixture was diluted with ethyl acetate. Sodium sulfate was added. The mixture was filtered and the filtrate was concentrated in vacuo. The crude oil was purified on silica gel (Eluent: Heptane/ethyl acetate 0 to 100%) to provide 0.14 g (47%) of the title compound as a yellow oil. MS (m/e): 191.5 (M+H+)

Example A.2

Preparation of rac-3-(4-Fluoro-phenyl)-1-methyl-piperidin-3-ylamine

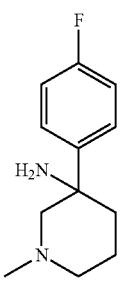

In analogy to the procedure described for the synthesis of example A.1 (step 1-3), the title compound was prepared from 3-oxo-piperidine-1-carboxylic acid benzyl ester (commercial) and 4-fluoro-phenylmagnesium bromide. MS (m/e): 209.2 (M+H+).

Example A.3

Preparation of rac-3-(4-Chloro-phenyl)-1-methyl-piperidin-3-ylamine

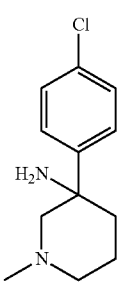

In analogy to the procedure described for the synthesis of example A.1 (step 1-3), the title compound was prepared from 3-oxo-piperidine-1-carboxylic acid benzyl ester (commercial) and 4-chloro-phenylmagnesium bromide. MS (m/e): 225.3 (M+H+).

Example A.4

Preparation of
rac-1-Methyl-3-p-tolyl-piperidin-3-ylamine

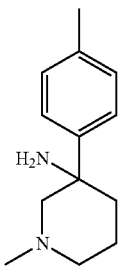

In analogy to the procedure described for the synthesis of example A.1 (step 1-3), the title compound was prepared from 3-oxo-piperidine-1-carboxylic acid benzyl ester (commercial) and 4-methyl-phenylmagnesium bromide. MS (m/e): 205.3 (M+H$^+$).

Example A.5

Preparation of
rac-1,2-Dimethyl-3-phenyl-piperidin-3-ylamine

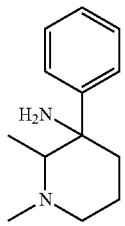

a) step 1:
3-Hydroxy-2-methyl-piperidine-1-carboxylic acid benzyl ester

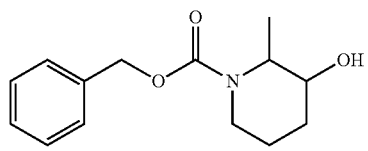 [SMILES: CC1C(O)CCCN1C(=O)OCc1ccccc1]

To a solution of 1.4 g (9.232 mmol) 2-methyl-piperidin-3-ol (CAS: 4766-56-7) in 9.8 ml dichloromethane under argon at room temperature, was added 2.57 ml (18.46 mmol) triethylamine. The mixture was stirred for 15 minutes and then cooled to 0° C. 1.37 ml (9.232 mmol) benzyl chloroformate was added dropwise. The reaction mixture was allowed to come to room temperature and the stirring was continued overnight. The mixture was extracted three times with water and the combined extracts were dried over sodium sulfate, filtered and concentrated in vacuo. The crude product was purified with flash column chromatography on silica gel (Eluent: Heptane/ethyl acetate 0 to 30) to provide 800 mg (34.8%) of the title compound as a colorless oil. MS (m/e): 272.4 (M+Na$^+$)

b) step 2:
rac-2-Methyl-3-oxo-piperidine-1-carboxylic acid benzyl ester

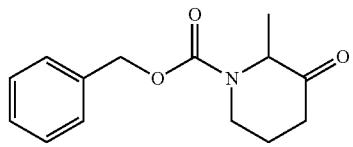 [SMILES: CC1C(=O)CCCN1C(=O)OCc1ccccc1]

To a stirred solution of 309.5 ul (3.530 mmol) oxalyl chloride in 3 ml dichloromethane at −50° C. to −60° C. was added a solution of 873 ul DMSO in 2 ml dichloromethane. The reaction mixture was stirred for 10 minutes, after which a solution of 800 mg (3.209 mmol) 3-hydroxy-2-methyl-piperidine-1-carboxylic acid benzyl ester in 3 ml dichloromethane was added over a period of 10 minutes. Stirring was continued for an additional 30 minutes. To this, was subsequently added 2.24 ml (16.05 mmol) triethylamine. The reaction mixture was stirred for 15 minutes, then allowed to warm to room temperature, taken in water, separated, and the aqueous layer extracted with dichloromethane. The combined organic layers were washed twice with water, dried over sodium sulfate, filtered and concentrated in vacuo. The crude product was purified with flash column chromatography on silica gel (Eluent: Heptane/ethyl acetate 0 to 40) to provide 600 mg (76%) of the title compound as a light yellow oil. MS (m/e): 270.2 (M+Na$^+$).

c) step 3:
rac-1,2-Dimethyl-3-phenyl-piperidin-3-ylamine

In analogy to the procedure described for the synthesis of example A.1 (step 1-3), the title compound was prepared from rac-2-methyl-3-oxo-piperidine-1-carboxylic acid benzyl ester and phenylmagnesium bromide. MS (m/e): 205.2 (M+H$^+$).

Example A.6

Preparation of rac-3-(3-Chloro-phenyl)-1-methyl-piperidin-3-ylamine

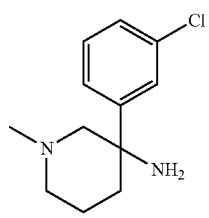

a) step 1: rac-4-(3-Chloro-phenyl)-4-nitro-butyric acid methyl ester

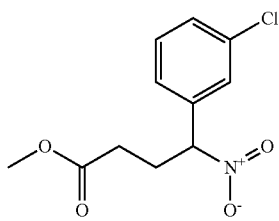 [SMILES: COC(=O)CCC(c1cccc(Cl)c1)[N+](=O)[O-]]

To a solution of 1 g (5.828 mmol) 1-chloro-3-nitromethyl-benzene (CAS: 38362-91-3) at 0° C. in 2 ml dioxane was added 0.512 g (5.828 mmol) methyl acrylate followed by 3.3 g Amberlyst A-21. The reaction mixture was stirred overnight at room temperature, filtered and the filtrate was dried over sodium sulfate and concentrated in vacuo. The crude product was purified with flash column chromatography on silica gel (Eluent: Heptane/ethyl acetate 0 to 10%) to provide 980 mg (65%) of the title compound as a colorless oil.

b) step 2: rac-5-(3-Chloro-phenyl)-1-methyl-5-nitro-piperidin-2-one

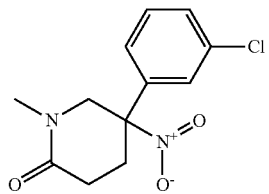 [SMILES: CN1CC(c2cccc(Cl)c2)([N+](=O)[O-])CCC1=O]

To a stirred room temperature solution of 164 ul (1.940 mmol) methylamine (41% in water) in 1 ml dioxane was added 141 ul (1.940 mmol) formaldehyde (37% in water) dropwise (exothermic reaction). The mixture was stirred for 5 min and then a solution of 0.5 g (1.940 mmol) rac-4-(3-chloro-phenyl)-4-nitro-butyric acid methyl ester in 1.5 ml dioxane was added at once. The mixture was stirred at 65° C. for 6 h. The mixture was cooled to room temperature, ethyl acetate and a saturated NaCl solution were added. Aqueous phase was extracted 2 times with ethyl acetate. Combined organic phases were washed with a saturated NaCl solution, dried over sodium sulfate and concentrated in vacuo. The crude product was purified with flash column chromatography on silica gel (Eluent: Heptane/ethyl acetate 0 to 100%) to provide 395 mg (76%) of the title compound as a colorless oil. MS (m/e): 269.2 (MH+).

c) step 3: rac-5-Amino-5-(3-chloro-phenyl)-1-methyl-piperidin-2-one

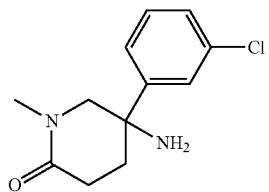 [SMILES: CN1CC(N)(c2cccc(Cl)c2)CCC1=O]

To a solution of 115 mg (0.428 mmol) 5-(3-chloro-phenyl)-1-methyl-5-nitro-piperidin-2-one in 0.5 ml dioxane was added 2 ml 3N HCl and 280 mg (4.28 mmol) zinc dust. The mixture was stirred at room temperature for 30 minutes. The mixture was filtered and the filtrate was basified with a 5N NaOH solution. Ethyl acetate was added. The mixture was filtered through a pad of dicalite. The organic layer was separated and the aqueous layer was extracted twice with ethyl acetate. The combined extracts were dried over sodium sulfate, filtered and concentrated in vacuo to provide 88 mg (86%) of the title compound as a light yellow oil. MS (m/e): 239.0 (MH+).

d) step 4: rac-3-(3-Chloro-phenyl)-1-methyl-piperidin-3-ylamine

To a slurry of 20 mg (0.494 mmol) LiAlH$_4$ in 0.5 ml THF was added dropwise a solution of 59 mg (0.247 mmol) rac-5-amino-5-(3-chloro-phenyl)-1-methyl-piperidin-2-one in 0.6 ml THF at room temperature. The mixture was refluxed for 30 minutes. The mixture was cooled in an ice bath and quenched carefully with 20 ul water, 20 ul 5N NaOH and finally 60 ul water. Ethyl acetate was added. The mixture was filtered and the filtrate was concentrated in vacuo to provide 48 mg (86%) of the title compound as a colorless oil. MS (m/e): 225.2 (MH+).

Example A.7

Preparation of rac-3-(4-Methoxy-phenyl)-1-methyl-piperidin-3-ylamine

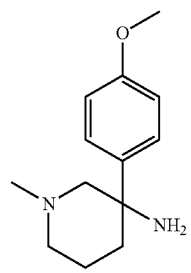 [SMILES: COc1ccc(C2(N)CCCN(C)C2)cc1]

a) step 1: rac-4-(4-Methoxy-phenyl)-4-nitro-butyric acid methyl ester

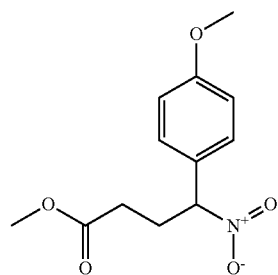 [SMILES: COC(=O)CCC(c1ccc(OC)cc1)[N+](=O)[O-]]

As described by Buchwald et al. (J. Org. Chem. 2002, 106): in a flask was added successively: 187 mg (0.198 mmol) Pd$_2$dba$_3$, 247 mg (0.791 mmol) 2-(Di-t-butylphosphino)-2'-methybiphenyl, and 1.555 g (4.747 mmol) cesium carbonate. The mixture was put under argon and 740 mg (3.956 mmol) 4-bromoanisole, 15 ml of DME and finally 600 mg (3.956 mmol) of methyl 4-nitrobutyrate were successively added. The mixture was stirred vigorously for 1 minute at room temperature and the flask was placed in a preheated oil bath at 50° C. and stirred at this temperature overnight. The reaction mixture was cooled to room temperature, and a saturated NH$_4$Cl solution and ethyl acetate were added. Aqueous phase was extracted 3 times with ethyl acetate and combined organic phases were washed with brine, and concentrated in vacuo. The crude product was purified with flash column chromatography on silica gel (Eluent: heptane/ethyl acetate 0 to 20%) to provide 897 mg (90%) of the title compound as a orange oil.

b) step 2: rac-3-(4-Methoxy-phenyl)-1-methyl-piperidin-3-ylamine

In analogy to the procedure described for the synthesis of example A.6 (steps: 2-4), the title compound was prepared from rac-4-(4-Methoxy-phenyl)-4-nitro-butyric acid methyl ester. MS (m/e): 221.2 (MH+).

Example A.8

Preparation of rac-5-Fluoro-1'-methyl-1',4',5',6'-tetrahydro-2H-[2,3']bipyridinyl-3'-ylamine

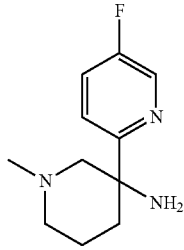

In analogy to the procedure described for the synthesis of example A.7 (steps: 1-2), the title compound was prepared from methyl 4-nitrobutyrate and 2-bromo-5-fluoropyridine. MS (m/e): 210.2 (MH+).

Example A.9

Preparation of rac-5-Fluoro-1-methyl-3-phenyl-piperidin-3-ylamine

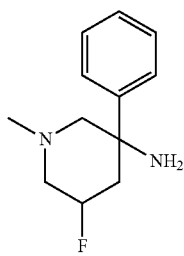

a) step 1:
rac-1-Methyl-5-nitro-5-phenyl-piperidin-2-one

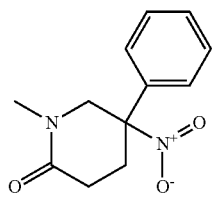 [SMILES: CN1CC(c2ccccc2)([N+](=O)[O-])CCC1=O]

In analogy to the procedure described for the synthesis of example A.6 (steps: 1-2), the title compound was prepared from nitromethyl-benzene (CAS: 622-42-4). MS (m/e): 235.2 (MH+).

b) step 2: rac-3-Fluoro-1-methyl-5-nitro-5-phenyl-piperidin-2-one

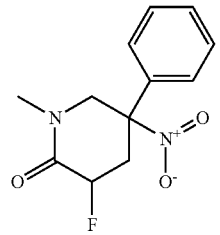 [SMILES: CN1CC(c2ccccc2)([N+](=O)[O-])CC(F)C1=O]

To a solution of 78.4 ul (0.555 mmol) diisopropylamine in 2 ml THF were added 347 ul (0.555 mmol) of a 1.6M n-BuLi solution in hexane at −5° C. The solution was stirred for 15 minutes at 0° C. and then cooled to −70° C. A solution of 100 mg (0.427 mmol) rac-1-methyl-5-nitro-5-phenyl-piperidin-2-one in 1 ml THF was added dropwise. The brown solution was stirred at −70° C. for 45 minutes. A solution of 180 mg (0.555 mmol) N-fluorobenzenesulphonimide in 1 ml THF was added dropwise. The mixture was stirred at −70° C. for 1.5 hour, quenched with 2 ml of a 20% NH$_4$Cl solution and allowed to warm to room temperature. Water and ethyl acetate were added. The aqueous layer was extracted twice with ethyl acetate. The combined organic layers were dried over sodium sulfate, filtered and concentrated in vacuo. The crude oil was purified on silica gel (Eluent: Heptane/ethyl acetate 0 to 100%) to provide 58 mg (54%) of the title compound as a light yellow solid. MS (m/e): 253.2 (M+H).

c) step 3: rac-5-Amino-3-fluoro-1-methyl-5-phenyl-piperidin-2-one

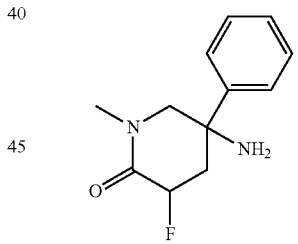

To a solution of 55 mg (0.218 mmol) rac-3-fluoro-1-methyl-5-nitro-5-phenyl-piperidin-2-one in 1.5 ml THF at 0° C. was added 100 ul Raney Nickel (50% in water). The mixture was stirred under a hydrogen atmosphere at 0° C. for 2 hours. The mixture was filtered and the catalyst was washed with THF. The filtrate was concentrated in vacuo to provide 48 mg (99%) of the title compound as a light yellow solid. MS (m/e): 223.3 (M+H).

d) step 4:
rac-5-Fluoro-1-methyl-3-phenyl-piperidin-3-ylamine

In analogy to the procedure described for the synthesis of example A.6 (steps: 4), the title compound was prepared from rac-5-amino-3-fluoro-1-methyl-5-phenyl-piperidin-2-one. MS (m/e): 192.3 (M-NH$_2$).

Example A.10

Preparation of rac-5-Methoxymethoxy-1-methyl-3-phenyl-piperidin-3-ylamine

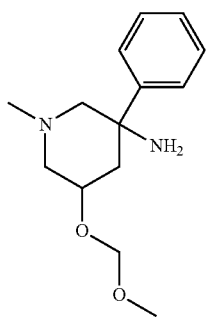 [SMILES: COCOC1CN(C)CC(N)(c2ccccc2)C1]

a) step 1: rac-3-Hydroxy-1-methyl-5-nitro-5-phenyl-piperidin-2-one

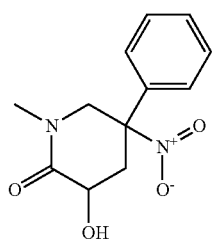 [SMILES: CN1CC(c2ccccc2)([N+](=O)[O-])CC(O)C1=O]

To a solution of 118 ul (0.833 mmol) diisopropylamine in 3 ml THF were added 520 ul (0.833 mmol) of a 1.6M n-BuLi solution in hexane at −5° C. The solution was stirred for 15 minutes at 0° C. and then cooled to −70° C. A solution of 150 mg (0.641 mmol) rac-1-methyl-5-nitro-5-phenyl-piperidin-2-one (example A.9, step 1) in 1.5 ml THF was added dropwise. The brown solution was stirred at −70° C. for 45 minutes. 517 mg (1.282 mmol) (oxodiperoxy(pyridine) (1,3-dimethyl-3,4,5,6-tetrahydro-2(1H)-pyrimidone) molybdenum(IV)) were added portionwise at −70° C. The mixture was stirred at −70° C. for 1 hour and then allowed to warm to 0° C. After 1 hour at 0° C., the mixture was quenched with 2.5 ml of a saturated solution of sodium sulfite. Water and ethyl acetate were added. The aqueous layer was extracted once with ethyl acetate. The combined organic layers were dried over sodium sulfate, filtered and concentrated in vacuo. The crude oil was purified on silica gel (Eluent: Heptane/ethyl acetate 0 to 100%) to provide 82 mg (51%) of the title compound as a light brown oil. MS (m/e): 251.1 (MH+).

b) step 2: rac-3-Methoxymethoxy-1-methyl-5-nitro-5-phenyl-piperidin-2-one

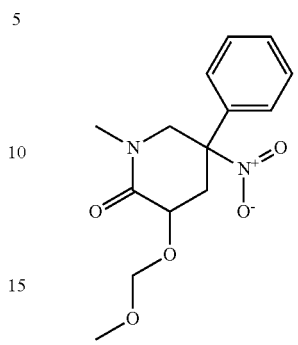

To a solution of 50 mg (0.2 mmol) rac-3-hydroxy-1-methyl-5-nitro-5-phenyl-piperidin-2-one and 52 ul (0.3 mmol) N-ethyl diisopropylamine in 1,2-dimethoxyethane were added 23 ul (0.3 mmol) chloromethyl methyl ether at room temperature. After 1 hour, the solution was heated in a 60° C. oil bath for 20 hours. The mixture was cooled to room temperature. 52 ul (0.3 mmol) N-ethyl diisopropylamine and 23 ul (0.3 mmol) chloromethyl methyl ether were added. The mixture was heated in a 60° C. oil bath for 4 hours. The solvent was removed in vacuo. The residue was taken in ethyl acetate. The mixture was washed once with water. The aqueous layer was extracted once with ethyl acetate. The combined extracts were dried over sodium sulfate, filtered and concentrated in vacuo. The crude oil was purified on silica gel (Eluent: Heptane/ethyl acetate 0 to 100%) to provide 30 mg (51%) of the title compound as a yellow oil. MS (m/e): 295.2 (MH+).

c) step 3: rac-5-Amino-3-methoxymethoxy-1-methyl-5-phenyl-piperidin-2-one

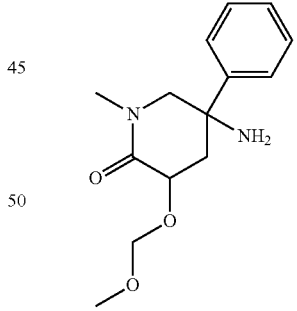

In analogy to the procedure described for the synthesis of example A.9 (steps: 3), the title compound was prepared from rac-3-methoxymethoxy-1-methyl-5-nitro-5-phenyl-piperidin-2-one. MS (m/e): 265.1 (MH+).

d) step 4: rac-5-Methoxymethoxy-1-methyl-3-phenyl-piperidin-3-ylamine

In analogy to the procedure described for the synthesis of example A.6 (steps: 4), the title compound was prepared from rac-5-amino-3-methoxymethoxy-1-methyl-5-phenyl-piperidin-2-one. MS (m/e): 251.2 (MH+).

Example A.11

Preparation of rac-3-Cyclohexyl-1-methyl-piperidin-3-ylamine

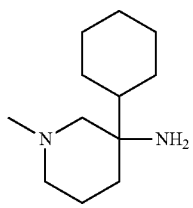

a) step 1: rac-4-Cyclohexyl-4-nitro-butyric acid methyl ester

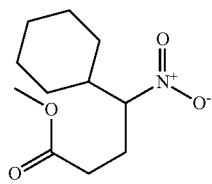

To a solution of 3.18 g (22.2 mmol) nitromethyl-cyclohexane (CAS: 2625-30-1) in 1 ml tert-butanol and 0.12 ml 35% benzyltrimethylammonium hydroxide in methanol warmed to 40° C. were added 1.99 ml (22.2 mmol) methyl acrylate. The yellow mixture was stirred at 40° C. for 2 hours then diluted with water and extracted with ethyl acetate. The combined extracts were washed with brine, dried over sodium sulfate, filtered and evaporated. The title compound was obtained in as slightly yellow oil: MS (EI): 198 (M.$^+$–MeO), 183 (M.$^+$–NO2), 151 (M–(MeO+NO2+H)).$^+$ (100%).

b) step 2: rac-5-Cyclohexyl-1-methyl-5-nitro-piperidin-2-one

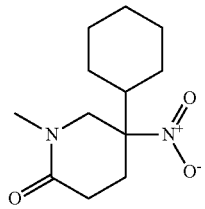 [SMILES: CN1CC(C2CCCCC2)([N+](=O)[O-])CCC1=O]

To 4.25 g (18.5 mmol) rac-4-cyclohexyl-4-nitro-butyric acid methyl ester were added 4.56 ml (32.5 mmol) 1,3,5-trimethylhexahydro-1,3,5-triazine and the mixture heated to 100° C. for 4 hours. The reaction mixture was cooled to ambient temperature and adsorbed on silica gel which was transferred on top of a silica gel column and purified by flash-chromatography with a gradient of heptane and 10 to 75% ethyl acetate: 2.55 g of title compound were isolated as colourless oil: MS (m/e): 240 (MH+).

c) step 3: rac-5-Amino-5-cyclohexyl-1-methyl-piperidin-2-one

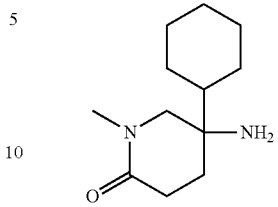

To a solution of 500 mg (2.08 mmol) rac-5-cyclohexyl-1-methyl-5-nitro-piperidin-2-one in 5 ml methanol were added 500 mg wet Raney Nickel and the mixture stirred under a hydrogen atmosphere at normal pressure and ambient temperature for 22 hours. Then the reaction mixture was filtered through a Dicalite pad, the precipitate washed with methanol and the filtrate evaporated: 452 mg title compound were obtained as colourless oil which was used without purification for the next step.

d) step 4: rac-3-Cyclohexyl-1-methyl-piperidin-3-yl-amine

To 2.06 ml of a 2.5M lithium aluminium hydride solution in tetrahydrofuran cooled to 0° C. was added dropwise a solution of 452 mg (2.15 mmol) rac-5-amino-5-cyclohexyl-1-methyl-piperidin-2-one in 6 ml tetrahydrofuran. Then the solution was heated to 65° C. for 1 hour. The turbid reaction solution was cooled with an ice bath and below 12° C. were added drop-wise 0.13 ml water, 0.32 ml 2N NaOH and further 0.19 ml water. The suspension was diluted with tert-butyl methyl ether, dried over sodium sulfate, filtered and evaporated: 368 mg title compound were obtained as colourless oil which was used without purification for the next step.

Example A.12

Preparation of rac-1-Methyl-3-(tetrahydro-pyran-4-yl)-piperidin-3-ylamine

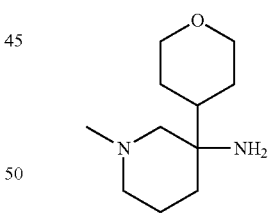

a) step 1: 4-Nitromethyl-tetrahydro-pyran

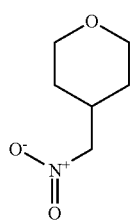

To a stirred suspension of 1.81 g (11.8 mmol) silver nitrite in 6 ml acetonitrile in a reaction flask enwrapped with aluminum foil, cooled to 0° C. was added drop-wise within 5 min 1.60 g (8.93 mmol) 4-bromomethyl-tetrahydro-pyran. Stirring was then continued at ambient temperature for 93 h. The reaction mixture was filtered and washed thoroughly with diethyl ether. The filtrate was mixed with silica gel and evaporated. The residue was transferred onto a silica gel column and purified by flash-chromatography on silica gel (eluent: heptane/ethyl acetate 9:1). The title compound (441 mg) was obtained as colorless oil.

b) step 2: rac-1-Methyl-3-(tetrahydro-pyran-4-yl)-piperidin-3-ylamine

In analogy to the procedure described for the synthesis of example A.11 (steps: 1-4), the title compound was prepared from 4-nitromethyl-tetrahydro-pyran.

Example A.13

Preparation of rac-1,3-Dimethyl-piperidin-3-ylamine dihydrochloride

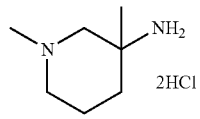

a) step 1:
rac-3-Isocyanato-3-methyl-piperidine-1-carboxylic acid tert-butyl ester

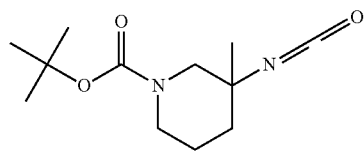 [SMILES: CC1(N=CC=O)CCCN(C(=O)OC(C)(C)C)C1]

To a suspension of 727 mg (3.0 mmol) rac-3-methyl-piperidine-1,3-dicarboxylic acid 1-tert-butyl ester (CAS: 534602-47-6) in 8 ml toluene was added at ambient temperature 0.42 ml (3.0 mmol) triethylamine. To the resulting solution was added under stirring 0.72 ml (3.3 mmol) diphenylphosphoryl azide and the mixture heated to 90° C. (gas evolution) for 90 min. The reaction mixture was poured onto iced water and extracted 3 times with tert-butyl methyl ether. The combined extracts were washed with brine, dried over sodium sulfate, filtered and evaporated. The title compound was obtained as slightly yellow oil which was used without purification in the next step. MS (m/e): 240 (M).

b) step 2:
rac-3-Amino-3-methyl-piperidine-1-carboxylic acid tert-butyl ester

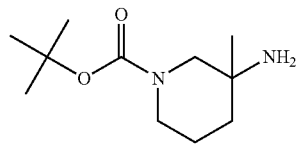

To a solution of 812 mg (3.38 mmol) rac-3-isocyanato-3-methyl-piperidine-1-carboxylic acid tert-butyl ester in 17 ml THF were added 16.9 ml 2N NaOH and the emulsion stirred vigorously at ambient temperature for 20 h. The emulsion was diluted with tert-butyl methyl ether and extracted three times. The combined extracts were washed with brine to neutral pH, dried over sodium sulfate, filtered and evaporated. The crude product was purified by column chromatography on silica gel with a gradient of heptane and 10 to 100% ethyl acetate then with ethyl acetate/MeOH provided the title compound: 232 mg colourless oil which crystallized at ambient temperature MS (m/e): 215.2 (M+H).

c) step 3: rac-1,3-Dimethyl-piperidin-3-ylamine dihydrochloride

To 3.15 ml 1M lithium aluminium hydride in THF was added at 5-10° C. drop-wise a solution of 225 mg (1.05 mmol) rac-3-amino-3-methyl-piperidine-1-carboxylic acid tert-butyl ester in 4 ml dry THF. The reaction mixture was heated to 65° C. for 1 h. The turbid reaction solution was cooled with an ice bath and below 12° C., were added drop-wise 0.13 ml water, 0.32 ml 2N NaOH and further 0.19 ml water. The suspension was diluted with tert-butyl methyl ether, dried over sodium sulfate, filtered and acidified with 2N HCl in diethyl ether. Evaporation provided 210 mg of the title compound as a colourless semisolid. MS (m/e): 129.3 (M+H).

Example A.14

Preparation of rac-3-(2,4-Difluorophenyl)-1-methyl-piperidin-3-ylamine

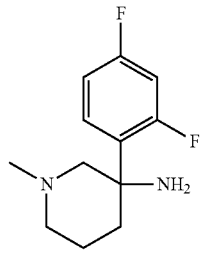 [SMILES: CN1CCCC(N)(c2ccc(F)cc2F)C1]

In analogy to the procedure described for the synthesis of example A.6 (steps: 1-4), the title compound was prepared from 2,4-difluoro-1-nitromethyl-benzene.

Example A.15

Preparation of rac-3-(2-Fluoro-phenyl)-1-methyl-piperidin-3-ylamine

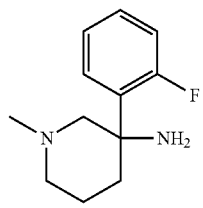

In analogy to the procedure described for the synthesis of example A.6 (steps: 1-4), the title compound was prepared from 1-fluoro-2-nitromethyl-benzene.

Example A.16

Preparation of rac-3-(2,5-Difluoro-phenyl)-1-methyl-piperidin-3-ylamine

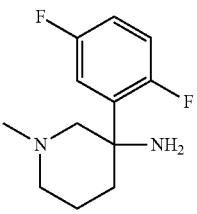

In analogy to the procedure described for the synthesis of example A.6 (steps: 1-4), the title compound was prepared from 1,4-Difluoro-2-nitromethyl-benzene.

Example A.17

Preparation of rac-1-Methyl-1,4,5,6-tetrahydro-2H-[3,4']bipyridinyl-3-ylamine

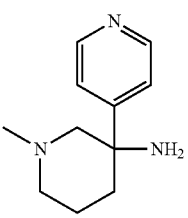

a) step 1: rac-1-Methyl-3-nitro-2,3,4,5-tetrahydro-1H-[3,4']bipyridinyl-6-one

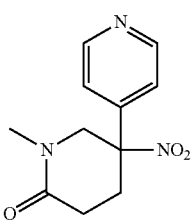 [SMILES: CN1CC(c2ccncc2)([N+](=O)[O-])CCC1=O]

In analogy to the procedure described for the synthesis of example A.6 (steps: 1-2), the title compound was prepared from 4-nitromethyl-pyridine (CAS: 22918-06-5).

b) step 2: rac-1-Methyl-3-nitro-2,3,4,5-tetrahydro-1H-[3,4']bipyridinyl-6-thione

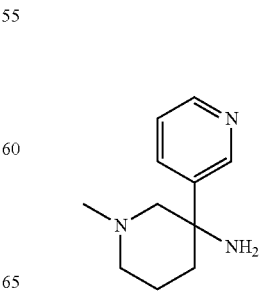

To a solution of 125 mg (0.531 mmol) rac-1-Methyl-3-nitro-2,3,4,5-tetrahydro-1H-[3,4]bipyridinyl-6-one in 2.5 ml toluene were added 240 mg (0.584 mmol) Lawesson reagent. The suspension was heated in a 80° C. oil bath for 30 minutes. The mixture was concentrated in vacuo. The crude oil was purified on silica gel (Eluent: Heptane/ethyl acetate 0 to 100%) to provide 105 mg (79%) of the title compound as a light yellow solid. MS (m/e): 252.1 (M+H).

c) step 3: rac-1-Methyl-3-nitro-1,2,3,4,5,6-hexahydro-[3,4']bipyridinyl

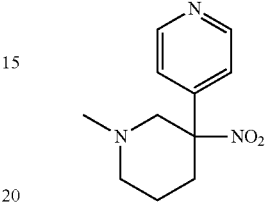

To a solution of 105 mg (0.418 mmol) rac-1-Methyl-3-nitro-2,3,4,5-tetrahydro-1H-[3,4']bipyridinyl-6-thione in 2.1 ml methanol was added 144 mg (3.8 mmol) NaBH$_4$. The mixture was stirred at room temperature for 20 minutes. Water (1.0 ml) was added. The mixture was stirred for 1 hour. The methanol was removed in vacuo. The residue was diluted with water and extracted 3 times with dichloromethane. The combined extracts were dried over sodium sulfate, filtered and concentrated in vacuo. The crude oil was purified on silica gel (Eluent: Heptane/ethyl acetate 0 to 100%) to provide 53 mg (57%) of the title compound as a yellow oil. MS (m/e): 222.3 (M+H).

d) step 4: rac-1-Methyl-1,4,5,6-tetrahydro-2H-[3,4'] bipyridinyl-3-ylamine

To a 0° C. cooled solution of 52 mg (0.235 mmol) rac-1-Methyl-3-nitro-1,2,3,4,5,6-hexahydro-[3,4']bipyridinyl in 2.0 ml THF were added 150 ul of Raney Nickel (50% in water). The mixture was stirred at 0° C. under a hydrogen atmosphere for 7 hours. The catalyst was filtered and the filtrate was concentrated in vacuo to provide 45 mg (88%) of the title compound as a light yellow oil. MS (m/e): 192.4 (M+H).

Example A.18

Preparation of rac-1-Methyl-1,4,5,6-tetrahydro-2H-[3,3']bipyridinyl-3-ylamine

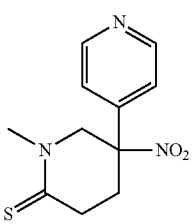 [SMILES: CN1CC(c2ccncc2)([N+](=O)[O-])CCC1=S]

a) step 1: rac-1-Methyl-3-nitro-2,3,4,5-tetrahydro-1H-[3,3']bipyridinyl-6-one

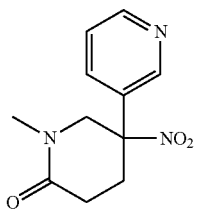 [SMILES: CN1CC(c2cccnc2)([N+](=O)[O-])CCC1=O]

In analogy to the procedure described for the synthesis of example A.7 (steps: 1-2), the title compound was prepared from 3-nitromethyl-pyridine (CAS: 69966-29-6).

b) step 2: rac-1-Methyl-1,4,5,6-tetrahydro-2H-[3,3']bipyridinyl-3-ylamine

In analogy to the procedure described for the synthesis of example A.17 (steps: 2-4), the title compound was prepared from rac-1-Methyl-3-nitro-2,3,4,5-tetrahydro-1H-[3,3]bipyridinyl-6-one.

Example A.19

Preparation of (3RS,5SR)-5-Methoxy-1-methyl-3-phenyl-piperidin-3-ylamine

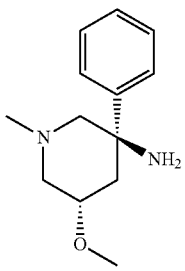 [SMILES: CO[C@@H]1CN(C)C[C@](N)(c2ccccc2)C1]

a) step 1: (3SR,5RS)-3-Methoxy-1-methyl-5-nitro-5-phenyl-piperidin-2-one

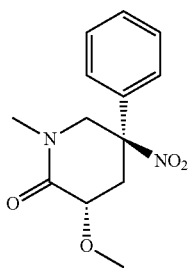 [SMILES: CO[C@H]1C[C@](c2ccccc2)([N+](=O)[O-])CN(C)C1=O]

A solution of 1.15 g (4.595 mmol) rac-3-Hydroxy-1-methyl-5-nitro-5-phenyl-piperidin-2-one (example A.10, step 1) in 11.5 ml DMF was cooled to 0° C. 220 mg (5.514 mmol) NaH (60% in oil) was added. The temperature rose to 3° C. The mixture was stirred at 0° C. for 15 minutes. 430 ul (6.893 mmol) iodomethane was added and the mixture was stirred at 0° C. for 30 minutes. 6.5 ml water was added and the solvent was removed in vacuo. The residue was taken in ethyl acetate. The solution was washed twice with water. The washings were reextracted once with ethyl acetate. The combined extracts were dried over sodium sulfate, filtered and concentrated in vacuo. The crude oil was purified on silica gel (Eluent: Heptane/ethyl acetate 0 to 100%) to provide 500 mg (42%) of the title compound as a light brown solid. MS (m/e): 265.1 (M+H).

b) step 2: (3SR,5RS)-5-Amino-3-methoxy-1-methyl-5-phenyl-piperidin-2-one

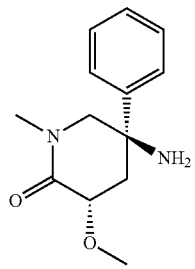 [SMILES: CO[C@H]1C[C@@](N)(c2ccccc2)CN(C)C1=O]

In analogy to the procedure described for the synthesis of example A.17 (steps: 4), the title compound was prepared from (3SR,5RS)-3-Methoxy-1-methyl-5-nitro-5-phenyl-piperidin-2-one.

c) step 3: (3RS,5SR)-5-Methoxy-1-methyl-3-phenyl-piperidin-3-ylamine

In analogy to the procedure described for the synthesis of example A.6 (steps: 4), the title compound was prepared from (3SR,5RS)-5-Amino-3-methoxy-1-methyl-5-phenyl-piperidin-2-one.

Example A.20

Preparation of (3RS,5SR)-1,5-Dimethyl-3-phenyl-piperidin-3-ylamine

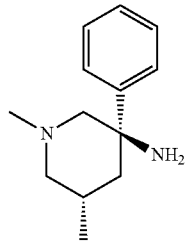

a) step 1: (3SR,5RS)-1,3-Dimethyl-5-nitro-5-phenyl-piperidin-2-one

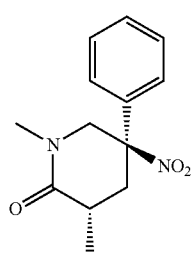 [SMILES: C[C@H]1C[C@](c2ccccc2)([N+](=O)[O-])CN(C)C1=O]

To a solution of 1.6 ml (11.1 mmol) diisopropylamine in 40 ml THF were added 7 ml (11.1 mmol) of a 1.6M n-BuLi solution in hexane at −5° C. The solution was stirred for 15 minutes at 0° C. and then cooled to −70° C. A solution of 2 g (8.538 mmol) rac-1-methyl-5-nitro-5-phenyl-piperidin-2-one (example A9, step 1) in 20 ml THF was added dropwise. The brown solution was stirred at −70° C. for 45 minutes. 639 ul (10.25 mmol) methyliodide in THF (8 ml) were added dropwise at −70° C. The mixture was stirred at −70° C. for 1 hour and then allowed to warm to 0° C. After 30 minutes at 0° C., the mixture was quenched with 30 ml of a 20% NH₄Cl solution. Water and ethyl acetate were added. The aqueous layer was extracted once with ethyl acetate. The combined organic phases were dried over sodium sulfate, filtered and concentrated in vacuo. The crude product was purified on silica gel (Eluent: Heptane/ethyl acetate 0 to 100%) to provide 1.72 g (81%) of the title compound as a yellow oil. MS (m/e): 249.2 (M+H)

b) step 2: (3SR,5RS)-5-Amino-1,3-dimethyl-5-phenyl-piperidin-2-one

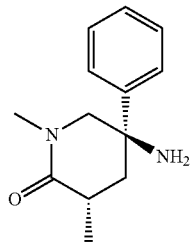 [SMILES: C[C@H]1C[C@@](N)(c2ccccc2)CN(C)C1=O]

In analogy to the procedure described for the synthesis of example A.17, step 4, the title compound was prepared from (3SR,5RS)-1,3-Dimethyl-5-nitro-5-phenyl-piperidin-2-one.
MS (m/e): 202.2 (M-NH₂)

c) step 3: (3RS,5SR)-1,5-Dimethyl-3-phenyl-piperidin-3-ylamine

In analogy to the procedure described for the synthesis of example A.6, step 4, the title compound was prepared from (3SR,5RS)-5-Amino-1,3-dimethyl-5-phenyl-piperidin-2-one.
MS (m/e): 205.3 (M+H).

Example A.21

Preparation of
rac-1,5,5-Trimethyl-3-phenyl-piperidin-3-ylamine

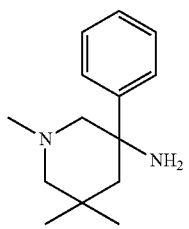 [SMILES: CN1CC(C)(C)CC(N)(c2ccccc2)C1]

a) step 1:
1,3,3-Trimethyl-5-nitro-5-phenyl-piperidin-2-one

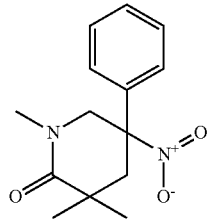 [SMILES: CN1CC(c2ccccc2)([N+](=O)[O-])CC(C)(C)C1=O]

To a solution of 170.7 ul (1.208 mmol) diisopropylamine in 4 ml THF were added 755 ul (1.208 mmol) of a 1.6M n-BuLi solution in hexane at −5° C. The solution was stirred for 15 minutes at 0° C. and then cooled to −70° C. Then 300 ul HMPA was added. A solution of 200 mg (0.805 mmol) (3SR,5RS)-1,3-dimethyl-5-nitro-5-phenyl-piperidin-2-one (example A.20, step a) in 2 ml THF was added dropwise. The brown solution was stirred at −70° C. for 45 minutes. 151 ul (2.415 mmol) methyliodide in THF (1 ml) were added dropwise at −70° C. The mixture was stirred at −70° C. for 1 hour and then allowed to warm to 0° C. After 1 hour at 0° C., the mixture was quenched with 7 ml of a 20% NH₄Cl solution. Water and ethyl acetate were added. The aqueous layer was extracted once with ethyl acetate. The combined organic phases were dried over sodium sulfate, filtered and concentrated in vacuo. The crude product was purified on silica gel (Eluent: Heptane/ethyl acetate 0 to 100%) to provide 131 mg (62%) of the title compound as a yellow oil. MS (m/e): 263.2 (M+H).

b) step 2:
rac-1,5,5-Trimethyl-3-phenyl-piperidin-3-ylamine

In analogy to the procedure described for the synthesis of example A.20, step 2-3, the title compound was prepared from 1,3,3-Trimethyl-5-nitro-5-phenyl-piperidin-2-one. MS (m/e): 219.4 (M+H).

Example A.22

Preparation of
rac-1,6,6-Trimethyl-3-phenyl-piperidin-3-ylamine

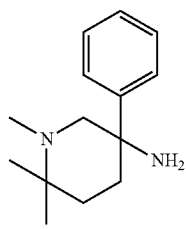 [SMILES: CN1CC(N)(c2ccccc2)CCC1(C)C]

a) step 1:
5-Amino-1-methyl-5-phenyl-piperidin-2-one

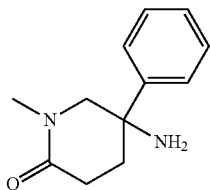

In analogy to the procedure described for the synthesis of example A.6, step 3, the title compound was prepared from 1-Methyl-5-nitro-5-phenyl-piperidin-2-one (example A.9, step 1). MS (m/e): 205.2 (M+H).

b) step 2: (1-Methyl-6-oxo-3-phenyl-piperidin-3-yl)-carbamic acid tert-butyl ester

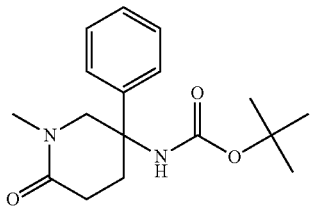 [SMILES: CN1CC(NC(=O)OC(C)(C)C)(c2ccccc2)CCC1=O]

To a solution of 1.5 g (7.35 mmol) 5-Amino-1-methyl-5-phenyl-piperidin-2-one in 30 ml THF under nitrogen at room temperature, were added 2.1 ml (14.7 mmol) triethylamine. A solution of 3.24 g (14.7 mmol) di-tert-butyl dicarbonate in 15 ml THF was added dropwise. The reaction mixture was stirred in a 55° C. oil bath for 7 hours and then at room temperature overnight. 100 ml water was added. The mixture was extracted 3 times with ethyl acetate. The combined organic phases were dried over sodium sulfate, filtered and concentrated in vacuo. The crude product was purified on silica gel (Eluent: Heptane/ethyl acetate 0 to 100%) to provide 1.21 g (54%) of the title compound as a yellow oil. MS (m/e): 305.3 (M+H).

c) step 3: (1,6,6-Trimethyl-3-phenyl-piperidin-3-yl)-carbamic acid tert-butyl ester

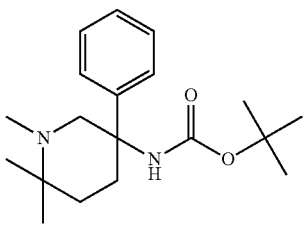 [SMILES: CN1CC(NC(=O)OC(C)(C)C)(c2ccccc2)CCC1(C)C]

A solution of 61 mg (0.2 mmol) (1-Methyl-6-oxo-3-phenyl-piperidin-3-yl)-carbamic acid tert-butyl ester in 2 ml THF was cooled to −20° C. 48 mg (0.2 mmol) Zirconium (IV) chloride were added at once. The temperature rose to −12° C. The mixture was stirred at −10° C. for 30 minutes. 400 ul (1.2 mmol) of a 3M methylmagnesium bromide solution in ether was added dropwise maintaining the temperature below −10° C. After 10 minutes the mixture was allowed to warm to room temperature. After 2 hours the mixture was cooled in an ice bath and quenched with 2 ml of a saturated NH₄Cl solution. Ethyl acetate and water were added. The organic layer was separated and the aqueous layer was extracted twice with ethyl acetate. The combined organic phases were dried over sodium sulfate, filtered and concentrated in vacuo to provide 50 mg (80%) of the title compound as a yellow oil. MS (m/e): 319.3 (M+H).

d) step 4:
rac-1,6,6-Trimethyl-3-phenyl-piperidin-3-ylamine

To a solution of 50 mg (0.157 mmol) (1,6,6-Trimethyl-3-phenyl-piperidin-3-yl)-carbamic acid tert-butyl ester in 0.3 ml dioxane was added 0.39 ml (1.57 mmol) of a 4M HCl solution in dioxane at room temperature. After 30 minutes 0.3 ml methanol was added to dissolve the product. The mixture was stirred at room temperature for 5 hours. The solvent was removed in vacuo. The residue was dissolved in water. The aqueous layer was extracted twice with ethyl acetate and then basified with a 2M sodium carbonate solution. The aqueous layer was extracted 3 times with dichloromethane. The combined organic phases were dried over sodium sulfate, filtered and concentrated in vacuo to provide 22 mg (64%) of the title compound as a brown oil. MS (m/e): 219.4 (M+H).

Example A.23

Preparation of rac-3-(3-Bromo-phenyl)-1-methyl-piperidin-3-ylamine

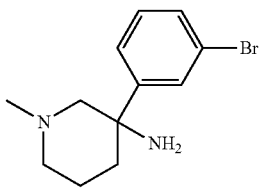

a) step 1: rac-3-(3-Bromo-phenyl)-1-methyl-3-nitro-piperidine

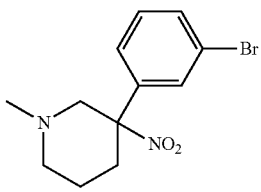 [SMILES: CN1CCCC(c2cccc(Br)c2)([N+](=O)[O-])C1]

In analogy to the procedure described for the synthesis of example A.17, step 1-3, the title compound was prepared from 1-Bromo-3-nitromethyl-benzene (CAS:854634-33-6).

MS (m/e): 300.3 (M+H).

b) step 2: rac-3-(3-Bromo-phenyl)-1-methyl-piperidin-3-ylamine

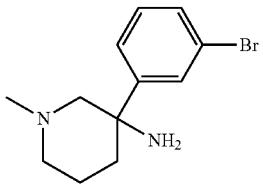

In analogy to the procedure described for the synthesis of example A.6, step 3, the title compound was prepared from rac-3-(3-Bromo-phenyl)-1-methyl-3-nitro-piperidine. MS (m/e): 269.2 (M+H).

Example A.24

Preparation of rac-3-(2-Chloro-4-fluoro-phenyl)-1-methyl-piperidin-3-ylamine

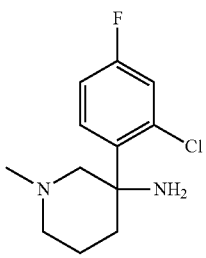 [SMILES: CN1CCCC(N)(c2ccc(F)cc2Cl)C1]

In analogy to the procedure described for the synthesis of example A.6 (steps: 1-4), the title compound was prepared from 2-chloro-4-fluoro-1-nitromethyl-benzene.

Example A.25

Preparation of rac-3-(5-Chloro-2-fluoro-phenyl)-1-methyl-piperidin-3-ylamine

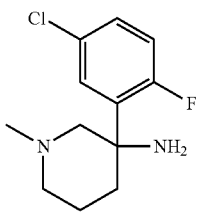 [SMILES: CN1CCCC(N)(c2cc(Cl)ccc2F)C1]

In analogy to the procedure described for the synthesis of example A.6 (steps: 1-4), the title compound was prepared from 4-Chloro-1-fluoro-2-nitromethyl-benzene.

Example A.26

Preparation of rac-1-Methyl-3-(3-trifluoromethyl-phenyl)-piperidin-3-ylamine

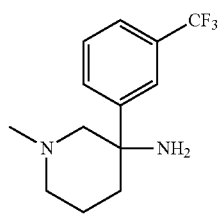 [SMILES: CN1CCCC(N)(c2cccc(C(F)(F)F)c2)C1]

In analogy to the procedure described for the synthesis of example A.6 (steps: 1-4), the title compound was prepared from 1-Nitromethyl-3-trifluoromethyl-benzene.

Example A.27

Preparation of rac-1-Methyl-3-(3-trifluoromethoxy-phenyl)-piperidin-3-ylamine

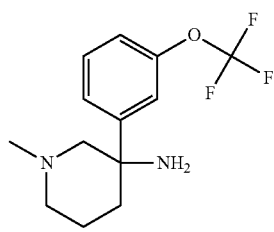 [SMILES: CN1CCCC(N)(c2cccc(OC(F)(F)F)c2)C1]

In analogy to the procedure described for the synthesis of example A.6 (steps: 1-4), the title compound was prepared from 1-Nitromethyl-3-trifluoromethoxy-benzene.

Example A.28

Preparation of rac-3-(3-Methoxy-phenyl)-1-methyl-piperidin-3-ylamine

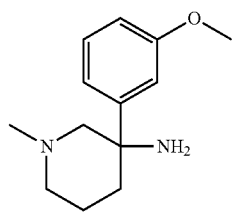

In analogy to the procedure described for the synthesis of example A.6 (steps: 1-4), the title compound was prepared from 1-Methoxy-3-nitromethyl-benzene.

Example A.29

Preparation of rac-3-(3-Difluoromethoxy-phenyl)-1-methyl-piperidin-3-ylamine

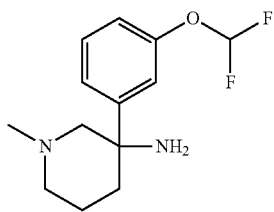 [SMILES: CN1CCCC(N)(c2cccc(OC(F)F)c2)C1]

In analogy to the procedure described for the synthesis of example A.6 (steps: 1-4), the title compound was prepared from 1-Difluoromethoxy-3-nitromethyl-benzene

Example A.30

Preparation of rac-3-(3-Fluoro-phenyl)-1-methyl-piperidin-3-ylamine

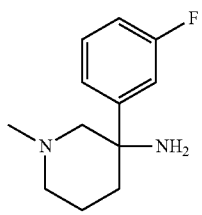

In analogy to the procedure described for the synthesis of example A.6 (steps: 1-4), the title compound was prepared from 1-Fluoro-3-nitromethyl-benzene.

Example A.31

Preparation of rac-3-(3-Chloro-4-fluoro-phenyl)-1-methyl-piperidin-3-ylamine

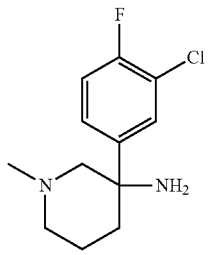 [SMILES: CN1CCCC(N)(c2ccc(F)c(Cl)c2)C1]

In analogy to the procedure described for the synthesis of example A.6 (steps: 1-4), the title compound was prepared from 2-Chloro-1-fluoro-4-nitromethyl-benzene.

Example A.32

Preparation of rac-3-(3,4-Difluoro-phenyl)-1-methyl-piperidin-3-ylamine

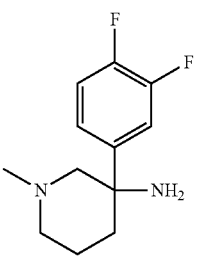 [SMILES: CN1CCCC(N)(c2ccc(F)c(F)c2)C1]

In analogy to the procedure described for the synthesis of example A.6 (steps: 1-4), the title compound was prepared from 1,2-Difluoro-4-nitromethyl-benzene.

Example A.33

Preparation of rac-1-Methyl-3-m-tolyl-piperidin-3-ylamine

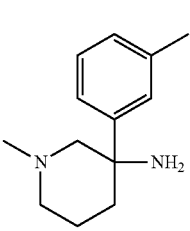

In analogy to the procedure described for the synthesis of example A.6 (steps: 1-4), the title compound was prepared from 1-Methyl-3-nitromethyl-benzene.

Example A.34

Preparation of rac-3-(4-Fluoro-3-methyl-phenyl)-1-methyl-piperidin-3-ylamine

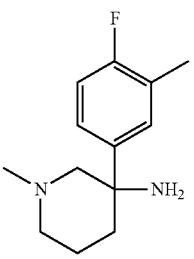

In analogy to the procedure described for the synthesis of example A.6 (steps: 1-4), the title compound was prepared from 1-Fluoro-2-methyl-4-nitromethyl-benzene.

Example A.35

Preparation of rac-3-(3,5-Difluoro-phenyl)-1-methyl-piperidin-3-ylamine

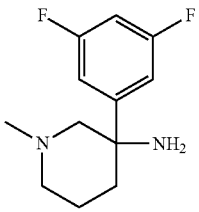 [SMILES: CN1CCCC(N)(c2cc(F)cc(F)c2)C1]

In analogy to the procedure described for the synthesis of example A.6 (steps: 1-4), the title compound was prepared from 1,3-Difluoro-5-nitromethyl-benzene.

Example A.36

Preparation of rac-1-Methyl-3-(3-thiazol-2-yl-phenyl)-piperidin-3-ylamine

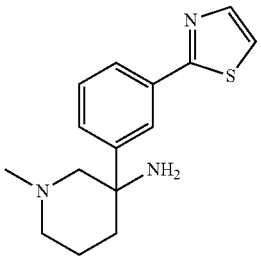 [SMILES: CN1CCCC(N)(c2cccc(-c3nccs3)c2)C1]

In analogy to the procedure described for the synthesis of example A.6 (steps: 1-4), the title compound was prepared from 2-(3-Nitromethyl-phenyl)-thiazole.

Example A.37

Preparation of rac-1-tert-Butyl-3-phenyl-piperidin-3-ylamine

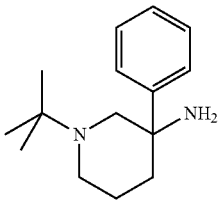 [SMILES: CC(C)(C)N1CCCC(N)(c2ccccc2)C1]

a) step 1: rac-4-Nitro-4-phenyl-butyric acid methyl ester

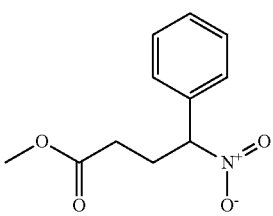 [SMILES: COC(=O)CCC(c1ccccc1)[N+](=O)[O-]]

In analogy to the procedure described for the synthesis of example A.6, step 1, the title compound was prepared from Nitromethyl-benzene (CAS: 622-42-4).

b) step 2: rac-5-Nitro-5-phenyl-piperidin-2-one

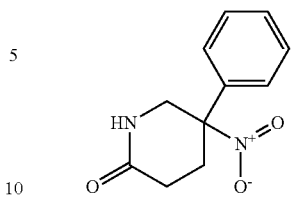

To a stirred solution of 2.11 g (26.88 mmol) ammonium acetate in 15 ml ethanol under nitrogen at room temperature, was added 980 ul (13.44 mmol) formaldehyde (37% in water), followed by a solution of 3 g (13.44 mmol) rac-4-Nitro-4-phenyl-butyric acid methyl ester in 7.5 ml ethanol. The mixture was refluxed for 26 hours then cooled to room temperature and the solvent was evaporated. Water was added. The resulting suspension was stirred for 15 minutes, filtered, rinsed with water, then with diethyl ether and dried in vacuo to provide 2.49 g (y: 84.1%) of the title compound as a white solid. MS (m/e): 221.2 (M+H).

c) step 3: rac-5-Amino-5-phenyl-piperidin-2-one

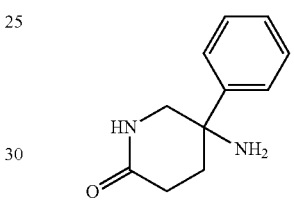

In analogy to the procedure described for the synthesis of example A.17, step 4, the title compound was prepared from rac-5-Nitro-5-phenyl-piperidin-2-one. MS (m/e): 191.4 (M+H).

d) step 4: rac-3-Phenyl-piperidin-3-ylamine

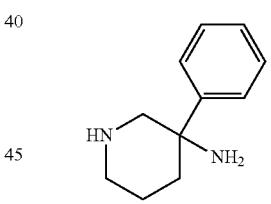

In analogy to the procedure described for the synthesis of example A.6, step 4, the title compound was prepared from rac-5-Amino-5-phenyl-piperidin-2-one. MS (m/e): 177.7 (M+H).

e) step 5: rac-2-(3-Amino-3-phenyl-piperidin-1-yl)-2-methyl-propionitrile

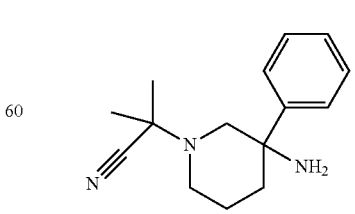

To a solution of 300 mg (1.701 mmol) rac-3-Phenyl-piperidin-3-ylamine in 1.3 ml acetic acid, was added dropwise 188 ul (2.553 mmol) acetone. The mixture was stirred at room temperature for 5 minutes. 320 ul (2.553 mmol) trimethylsilyl cyanide was added dropwise. The temperature rose to 31° C. The mixture was stirred at room temperature for 4 hours. The mixture was diluted with dichloromethane and cooled to 0° C. NaOH 2N was added dropwise to basify the mixture. The organic layer was separated and the aqueous layer was extracted twice with dichloromethane. The combined organic layers were dried over sodium sulfate, filtered and concentrated in vacuo to provide 315 mg (76.1%) of the title compound as a yellow oil.

MS (m/e): 244.4 (M+H).

f) step 6:
rac-1-tert-Butyl-3-phenyl-piperidin-3-ylamine

To a solution of 100 mg (0.411 mmol) rac-2-(3-Amino-3-phenyl-piperidin-1-yl)-2-methyl-propionitrile in 2.0 ml tetrahydrofuran over mol-sieve at 0° C. under nitrogen, was added dropwise 1.4 ul (4.11 mmol) of a 3M methylmagnesium bromide solution in diethyl ether. The mixture was stirred at 0° C. for 10 minutes, and then at 60° C. for 30 hours. The mixture was cooled in an ice bath and quenched with a saturated ammonium chloride solution. The mixture was extracted 3 times with ethyl acetate. The combined extracts were dried over sodium sulfate, filtered and concentrated in vacuo to provide 60 mg (63%) of the title compound as a yellow gum. MS (m/e): 233.2 (M+H).

Example A.38

Preparation of rac-4-Methyl-6-phenyl-4-aza-spiro[2.5]oct-6-ylamine hydrochloride

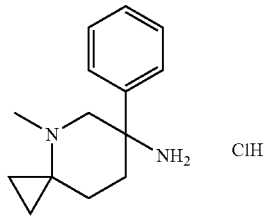 [SMILES: CN1CC(N)(c2ccccc2)CCC12CC2 ; Cl]

a) step 1: rac-(4-Methyl-6-phenyl-4-aza-spiro[2.5]oct-6-yl)-carbamic acid tert-butyl ester

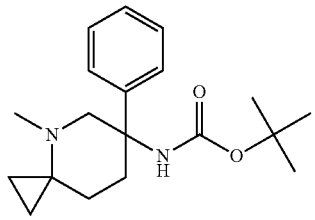 [SMILES: CN1CC(NC(=O)OC(C)(C)C)(c2ccccc2)CCC12CC2]

A solution of 333 ul (1.0 mmol) of a 3M ethyl magnesium bromide solution in ether in 4 ml THF was cooled to −70° C. A solution of 124 ul (0.42 mmol) titanium isopropoxide in 0.4 ml THF was added dropwise. The light brown mixture was stirred for 2 minutes. A solution of 122 mg (0.4 mmol) rac-(1-Methyl-6-oxo-3-phenyl-piperidin-3-yl)-carbamic acid ter!-butyl ester (example A.22, step 2) in 2.4 ml THF was added dropwise. The mixture was allowed to warm to room temperature and was stirred for 3 hours. The mixture was cooled in an ice bath and quenched with a 20% ammonium chloride solution. Water and ethyl acetate were added. The white suspension was filtered through a pad of dicalite. The organic layer was separated and the aqueous layer was extracted twice with ethyl acetate. The combined organic phases were dried over sodium sulfate, filtered and concentrated in vacuo. The crude product was purified on silica gel (Eluent: Heptane/ethyl acetate 0 to 100%) to provide 14 mg (11%) of the title compound as a colorless oil. MS (m/e): 317.2 (M+H).

b) step 2: rac-4-Methyl-6-phenyl-4-aza-spiro[2.5]oct-6-ylamine hydrochloride

In analogy to the procedure described for the synthesis of example A.22, step 4, the title compound was prepared from rac-(4-Methyl-6-phenyl-4-aza-spiro[2.5]oct-6-yl)-carbamic acid tert-butyl ester. MS (m/e): 217.4 (M+H).

Example B.1

Preparation of 2-bromo-6-methoxy-4-trifluoromethyl-benzoic acid

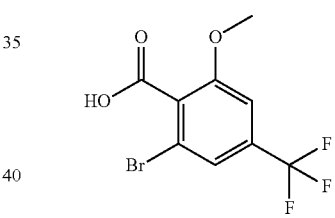

To −75° C. cooled THF (70 ml) was added dropwise 36 ml (50.0 mmol) of a 1.4 M sec-BuLi solution in cyclohexane within 5 minutes keeping the temperature below −70° C. 7.5 ml (50.0 mmol) TMEDA were added dropwise at temperature below −70° C. within 5 minutes. A solution of 5.0 g (22.71 mmol) 2-methoxy-4-(trifluoromethyl)benzoic acid (commercial) in THF (25 ml) was added dropwise at over a period of 20 minutes. The dark green solution was stirred at −75° C. for 2 hours. A solution of 29.6 g (90.84 mmol) 1,2-dibromotetrachloroethane in THF (30 ml) was added dropwise. The off-white suspension was stirred at −75° C. for 1 hour and then allowed to warm to room temperature. The yellow solution was quenched by dropwise addition of 60 ml water under ice bath cooling. The mixture was diluted with ethyl acetate (70 ml) and water (30 ml). The aqueous layer was extracted with ethyl acetate (50 ml), acidified with HCl 25% and extracted with ethyl acetate (3×50 ml). The extracts were combined, dried over sodium sulfate, filtered and concentrated in vacuo. The crude product was stirred in heptane, filtered and dried. The solid was recrystallized from heptane (7 ml) and ethyl acetate (2 ml) to provide 815 mg (12%) of the title compound as a white solid. MS (m/e): 298.9 (M−H).

Example B.2

Preparation of 2-Methoxy-6-methylsulfanyl-4-trifluoromethyl-benzoic acid

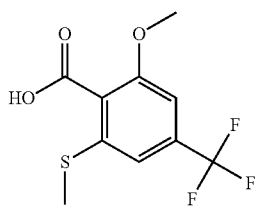 [SMILES: COc1cc(C(F)(F)F)cc(SC)c1C(=O)O]

In analogy to the procedure described for the synthesis of example B.1, the title compound was prepared from 2-methoxy-4-(trifluoromethyl)benzoic acid (commercial) and dimethyldisulfide.

Example B.3

Preparation of 2-Cyclopropyl-4-trifluoromethyl-benzoic acid

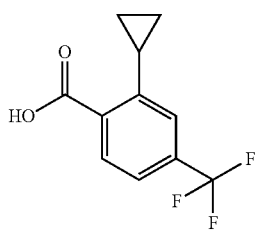 [SMILES: O=C(O)c1ccc(C(F)(F)F)cc1C1CC1]

a) step 1: 2-Bromo-4-trifluoromethyl-benzoic acid methyl ester

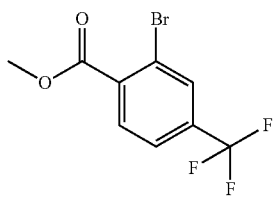

To a solution of 2 g (7.434 mmol) 2-bromo-4-trifluoromethyl-benzoic acid (CAS: 328-89-2) in 20 ml DMF under nitrogen at room temperature, was added 1.13 g (8.177 mmol) potassium carbonate and 557 ul (8.921 mmol) methyl iodide. The mixture was stirred overnight under nitrogen. The mixture was poured into water (300 ml). The aqueous layer was extracted with ethyl acetate (2×80 ml). The combined extracts were dried over sodium sulfate, filtered and concentrated in vacuo. The crude oil was purified on silica gel (Eluent: Heptane/ethyl acetate 0 to 10%) to provide 1.75 g (83%) of the title compound as an orange oil.

b) step 2: 2-Cyclopropyl-4-trifluoromethyl-benzoic acid methyl ester

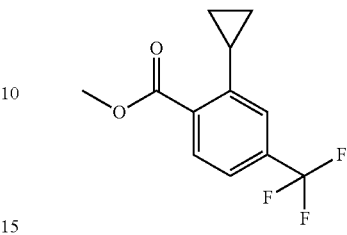

To a solution of 400 mg (1.413 mmol) 2-bromo-4-trifluoromethyl-benzoic acid methyl ester, 146 mg (1.696 mmol) cyclopropyl boronic acid, 1.21 g (4.946 mmol) tri-potassium phosphate monohydrate, 40.9 mg (0.141 mmol) tricyclohexyl phosphine in 6 ml toluene and 0.3 ml water under nitrogen at room temperature, was added 15.9 mg (0.0707 mmol) palladium acetate. The mixture was stirred in a 100° C. oil bath for 4 hours and overnight at room temperature under nitrogen. The mixture was cooled to room temperature. Water was added and the mixture extracted with ethyl acetate. The organic layer was washed once with brine, dried over sodium sulfate, filtered and concentrated in vacuo. The crude compound was purified on silica gel (Eluent: Heptane/ethyl acetate 0 to 10%) to provide 0.24 g (71%) of the title compound as a yellow oil.

c) step 3: 2-Cyclopropyl-4-trifluoromethyl-benzoic acid

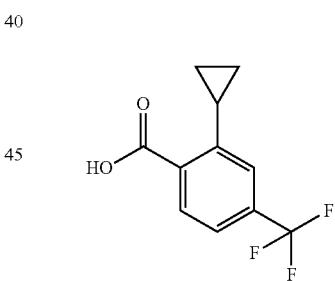

To a suspension of 485 mg (1.986 mmol) 2-cyclopropyl-4-trifluoromethyl-benzoic acid methyl ester in 8 ml ethanol at room temperature, was added 1.99 ml (3.972 mmol) 2N NaOH. The mixture was heated in an 80° C. oil bath for 30 minutes. The solution was cooled to room temperature and the ethanol was evaporated. The residue was diluted with water, acidified with 2N HCl to pH 2 and dichloromethane was added. The aqueous phase was extracted twice with dichloromethane. The combined organic phases were dried over sodium sulfate, filtered and concentrated in vacuo. The crude product was purified on silica gel (Eluent: Heptane/ethyl acetate 0 to 100%) to provide 0.197 g (27%) of the title compound as a light yellow solid.

MS (m/e): 229.0 (M−H).

55

Example B.4

Preparation of
5-Trifluoromethyl-biphenyl-2-carboxylic acid

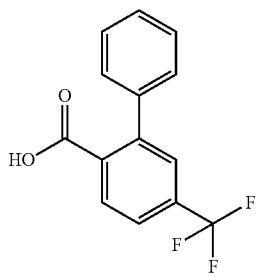 [SMILES: O=C(O)c1ccc(C(F)(F)F)cc1-c1ccccc1]

A mixture of 300 mg (0.949 mmol) 2-iodo-4-trifluoromethyl-benzoic acid (CAS: 54507-44-7), 239 mg (1.898 mmol) phenylboronic acid, 302 mg (2.847 mmol) sodium carbonate and 10.7 mg (0.0475 mmol) palladium acetate in 4.5 ml water was stirred at room temperature for 48 hours. The mixture was filtered and the filtrate was acidified with 37% HCl. The mixture was stirred at room temperature for 30 minutes. The solid was filtered, washed with water and dried to provide 225 mg (89%) of the title compound as a brown solid. MS (m/e): 264.9 (M+H$^+$)

Example B.5

Preparation of
2-Isopropoxy-4-trifluoromethyl-benzoic acid

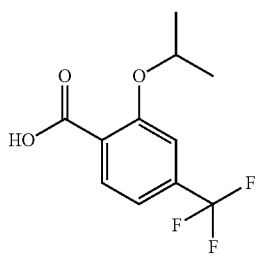 [SMILES: CC(C)Oc1cc(C(F)(F)F)ccc1C(=O)O]

To a solution of 500 mg (2.271 mmol) 2-hydroxy-4-trifluoromethyl-benzoic acid methyl ester (CAS: 345-28-8), 209 ul (2.725 mmol) 2-propanol and 706.2 mg (2.612 mmol) triphenylphosphine in 6.5 ml tetrahydrofuran under nitrogen at 0° C., was added dropwise a solution of 575.2 mg (2.498 mmol) di-tert-butyl azodicarboxylate in 1 ml tetrahydrofuran. The reaction mixture was allowed to warm to room temperature and stirred for 1.5 hours. 8 ml (15.9 mmol) 2N NaOH was added and the reaction mixture was warmed at 80° C. for 5 hours. The reaction mixture extracted twice with 5 ml ether. The aqueous layer was acidified under ice bath cooling with a 5N HCl solution to pH 1. The resulting precipitate was filtered and dried in vacuo to provide 444 mg (y: 78.8%) of the expected compound as a white solid. MS (m/e): 247.0 (MH+).

56

Example B.6

Preparation of 2-Methoxy-6-methylsulfanyl-4-trifluoromethyl-benzoyl chloride

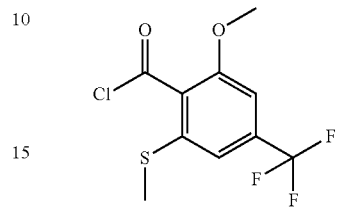

A mixture of 51 mg (0.191 mmol) 2-methoxy-6-methylsulfanyl-4-trifluoromethyl-benzoic acid (Example B.2) and 140 ul (1.91 mmol) thionylchloride in toluene (0.5 ml) was heated in a 80° C. oil bath for 4 hours. The solvent was removed in vacuo to provide the title compound.

Example B.7

Preparation of
2-Ethyl-4,6-bis-trifluoromethyl-benzoyl chloride

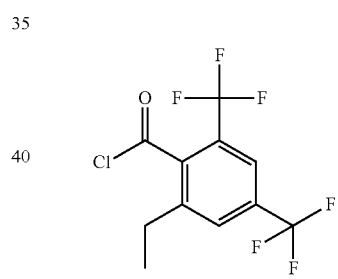

a) step 1: 2-Ethyl-4,6-bis-trifluoromethyl-benzoic acid

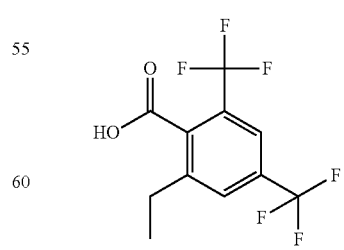

In analogy to the procedure described for the synthesis of example B.1, the title compound was prepared from 2,4-bis-trifluoromethyl-benzoic acid (commercial) and ethyliodide.

Example B.8

Preparation of 2-Difluoromethoxy-4-trifluoromethyl-benzoic acid

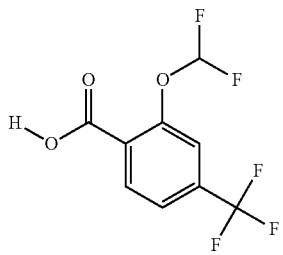 [SMILES: O=C(O)c1ccc(C(F)(F)F)cc1OC(F)F]

a) step 1: 2-Difluoromethoxy-4-trifluoromethyl-benzoic acid methyl ester

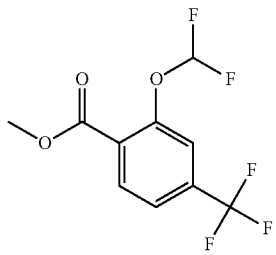 [SMILES: COC(=O)c1ccc(C(F)(F)F)cc1OC(F)F]

To a solution of 500 mg (2.271 mmol) 2-hydroxy-4-trifluoromethyl-benzoic acid methyl ester (CAS: 345-28-8) in 5 ml N,N-dimethylformamide at room temperature, was added 470.8 mg (3.407 mmol) potassium carbonate, followed by dropwise addition of 293.4 ul (2.725 mmol) methyl chlorodifluoroacetate. The reaction mixture was heated at 65° C. oil bath for 22 hours. Water and ethyl acetate were added. The organic phase was washed 3 times with water. The organic phase was dried over sodium sulfate, filtered and concentrated in vacuo to provide 449 mg of the title compound as a pink oil which was used in the next step without any further purification.

b) step 2: 2-Difluoromethoxy-4-trifluoromethyl-benzoic acid

In analogy to the procedure described for the synthesis of example B.3, step 3 the title compound was prepared from 2-difluoromethoxy-4-trifluoromethyl-benzoic acid methyl ester.

MS (m/e): 254.9 (M–H)

Example B.9

Preparation of 2-Pyrrolidin-1-yl-4-trifluoromethyl-benzoic acid

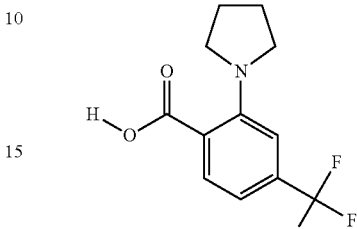

a) step 1: 2-Pyrrolidin-1-yl-4-trifluoromethyl-benzoic acid methyl ester

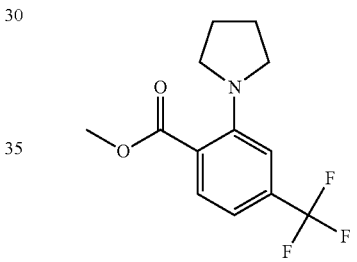

To 30 mg (0.0318 mmol) Pd$_2$ dba$_3$, 37.9 mg (0.106 mmol) 2-(dicyclohexyl-phosphino)biphenyl and 315 mg (1.484 mmol) potassium phosphate tribasic under argon at room temperature, was added a solution of 105.2 ul (1.272 mmol) pyrrolidine in 5.5 ml toluene dry, followed by 300 mg (1.06 mmol) 2-bromo-4-trifluoromethyl-benzoic acid methyl ester (CAS: 328-89-2). The reaction mixture was heated at 80° C. overnight. The mixture was cooled to room temperature and diluted with dichloromethane. The suspension was filtered. The filtrate was concentrated in vacuo. The residue was purified on silica (Eluent: heptane/ethyl acetate 0 to 10%) to provide 88 mg (30.4%) of the title compound as an orange oil. MS (m/e): 274.3 (MH+).

b) step 2: 2-Pyrrolidin-1-yl-4-trifluoromethyl-benzoic acid

In analogy to the procedure described for the synthesis of example B.3, step 3 the title compound was prepared from 2-pyrrolidin-1-yl-4-trifluoromethyl-benzoic acid methyl ester.

MS (m/e): 258.0 (M–H).

Example B.10

Preparation of
2-Cyclohexyl-4-trifluoromethyl-benzoic acid

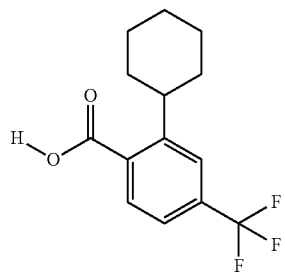 [SMILES: O=C(O)c1ccc(C(F)(F)F)cc1C1CCCCC1]

a) step 1: 2-Iodo-4-trifluoromethyl-benzoic acid methyl ester

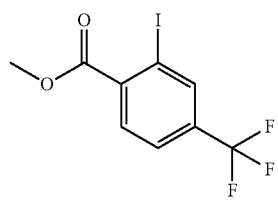

In analogy to the procedure described for the synthesis of example B.3, step 1 the title compound was prepared from 2-iodo-4-trifluoromethyl-benzoic acid (CAS: 54507-44-7).

b) step 2: 2-Cyclohexyl-4-trifluoromethyl-benzoic acid methyl ester

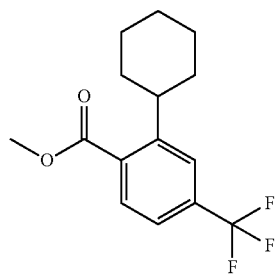 [SMILES: COC(=O)c1ccc(C(F)(F)F)cc1C1CCCCC1]

To a solution of 300 mg (0.909 mmol) 2-iodo-4-trifluoromethyl-benzoic acid methyl ester, 14.4 mg (0.0455 mmol) Pd(dppf)Cl$_2$ and 10.6 mg (0.0545 mmol) copper (I) iodide in THF (5 ml) was added at room temperature 2.73 ml (1.364 mmol) cyclohexylzinc bromide (0.5M). The mixture was stirred for 3 hours. Then it was heated to 50° C. and stirred for 4 hours and at room temperature over night. The mixture was concentrated in vacuo and dissolved in ethyl acetate. Then it was washed twice with a 1N HCl solution, twice with a saturated sodium bicarbonate solution and once with brine. The organic layer was dried over sodium sulfate, filtered and concentrated in vacuo. The residue was purified on silica (Eluent: heptane/ethyl acetate 0 to 20%) to provide 176 mg (68%) of the title compound as a light yellow oil. MS (m/e): 286 (MH+).

c) step 3: 2-Cyclohexyl-4-trifluoromethyl-benzoic acid

In analogy to the procedure described for the synthesis of example B.3, step 3 the title compound was prepared from 2-cyclohexyl-4-trifluoromethyl-benzoic acid methyl ester.

MS (m/e): 271.2 (M–H).

Example B.11

Preparation of
2-cyclopentyl-4-trifluoromethyl-benzoic acid

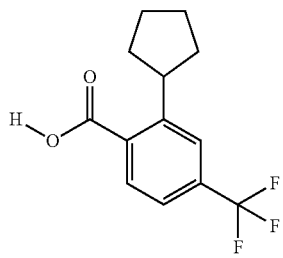 [SMILES: O=C(O)c1ccc(C(F)(F)F)cc1C1CCCC1]

In analogy to the procedure described for the synthesis of example B.10, the title compound was prepared from 2-iodo-4-trifluoromethyl-benzoic acid methyl ester and cyclopentyl zinc bromide followed by saponification with sodium hydroxide. MS (m/e): 257.0 (M–H).

Example B.12

Preparation of
2-Cyclobutyl-4-trifluoromethyl-benzoic acid

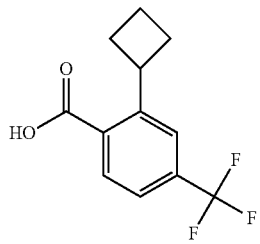 [SMILES: O=C(O)c1ccc(C(F)(F)F)cc1C1CCC1]

In analogy to the procedure described for the synthesis of example B.10, the title compound was prepared from 2-iodo-4-trifluoromethyl-benzoic acid methyl ester and cyclobutyl zinc bromide followed by saponification with sodium hydroxide. MS (m/e): 243.0 (M–H)

Example B.13

Preparation of 2-Isopropyl-4-trifluoromethyl-benzoic acid

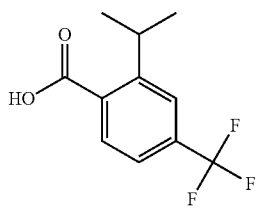 [SMILES: CC(C)c1cc(C(F)(F)F)ccc1C(=O)O]

In analogy to the procedure described for the synthesis of example B.10, the title compound was prepared from 2-iodo-4-trifluoromethyl-benzoic acid methyl ester and 2-propyl zinc bromide followed by saponification with sodium hydroxide. MS (m/e): 231.0 (M–H)

Example B.14

Preparation of 2,6-Dimethoxy-4-trifluoromethyl-benzoic acid

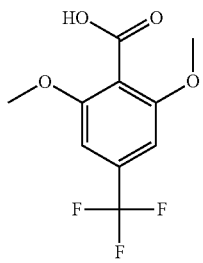

To a solution of sodium hydroxide (5.66 g, 141.4 mmol) in 33 ml water and 33 ml ethanol at room temperature under nitrogen, was added 2,6-dimethoxy-4-trifluoromethyl-benzonitrile (CAS: 51271-36-4) (3.27 g, 14.14 mmol). The reaction mixture was heated in a 90° C. oil bath for 37 hours. The reaction mixture was cooled to room temperature and 130 ml water was added. The product was collected by filtration and dried to provide 3.05 g of an off-white solid. To a solution of nitrosylsulfuric acid (15.6 g, 110.2 mmol) in 9.5 ml water at 0° C. under nitrogen, was added dropwise a suspension of the previously obtained material in 19 ml dichloromethane. The reaction mixture was stirred at 0° C. for 4.5 h. The reaction mixture was poured over ice and extracted with dichloromethane. The combined organic layers were dried over $Na_2SO_4$, filtered and dried to provide 1.51 g of product. The aqueous phase was filtered and the white solid was dried to provide 1.36 g of product. Both batches were mixed to provide 2.87 g (93.7%) of the title compound as a white solid. MS (m/e): 249.1 (M–H).

Example B.15

Preparation of 2-Methoxy-6-(2,2,2-trifluoro-ethoxy)-4-trifluoromethyl-benzoic acid

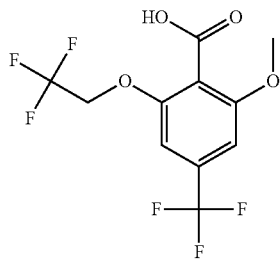 [SMILES: COc1cc(C(F)(F)F)cc(OCC(F)(F)F)c1C(=O)O]

a) step 1:
2-Methoxy-6-nitro-4-trifluoromethyl-benzonitrile

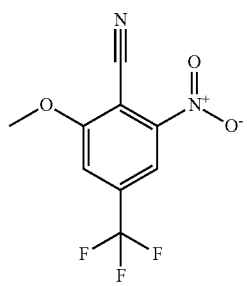 [SMILES: COc1cc(C(F)(F)F)cc([N+](=O)[O-])c1C#N]

To a solution of 3 g (11.49 mmol) 2,6-dinitro-4-trifluoromethyl-benzonitrile (CAS: 35213-02-6) in 30 ml methanol at 0° C. under nitrogen, was added 2.3 ml (11.49 mmol) of a 5M sodium methoxide in methanol. The reaction mixture was stirred at 0° C. for 1.5 hours then poured into ice water, stirred for 60 minutes and the product was collect by filtration. The crude solid was purified on silica (Eluent: heptane/ethyl acetate 0 to 30%) to provide 2.24 g (79%) of the title compound as a light yellow solid.

b) step 2: 2-Methoxy-6-(2,2,2-trifluoro-ethoxy)-4-trifluoromethyl-benzonitrile

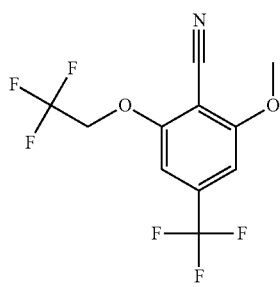 [SMILES: COc1cc(C(F)(F)F)cc(OCC(F)(F)F)c1C#N]

To a solution of 200 mg (0.804 mmol) 2-methoxy-6-nitro-4-trifluoromethyl-benzonitrile in 2.4 ml 2,2,2-trifluoroethanol under argon at 0° C. was added dropwise a solution of 81.3 mg (1.246 mmol) potassium hydroxide in 600 ul water. The mixture was refluxed for 2 days then cooled to room temperature and poured into ice/water. The resulting suspension was filtered and dried in vacuo to provide 112 mg (47%) of the title compound as a white solid. MS (m/e): 317.2 (M+H).

c) step 3: 2-Methoxy-6-(2,2,2-trifluoro-ethoxy)-4-trifluoromethyl-benzoic acid

In analogy to the procedure described for the synthesis of example B.14, the title compound was prepared from 2-methoxy-6-(2,2,2-trifluoro-ethoxy)-4-trifluoromethyl-benzonitrile. MS (m/e): 316.9 (M−H).

Example B.16

Preparation of 2-Ethyl-3-methyl-4-trifluoromethyl-benzoyl chloride

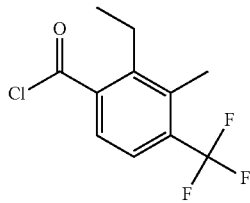 [SMILES: CCc1c(C(=O)Cl)ccc(C(F)(F)F)c1C]

a) step 1: 2-(2-Methoxy-4-trifluoromethyl-phenyl)-4,4-dimethyl-4,5-dihydro-oxazole

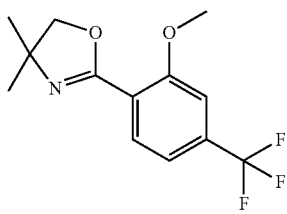 [SMILES: COc1cc(C(F)(F)F)ccc1C1=NC(C)(C)CO1]

To a solution of 24.98 g (113 mmol) 4-(trifluoromethyl)-2-methoxy-benzoic acid in 220 ml toluene were added 82 ml (1.13 mol) thionyl chloride and 5 drops dimethylformamide. The mixture was heated to 80° C. for 3 h. Then the reaction mixture was concentrated at 50° C./10 mbar. The remaining acid chloride, 27.9 g of a light yellow liquid, was dissolved in 160 ml dichloromethane, cooled to 0° C. and a solution of 20.34 g (228 mmol) 2-amino-2-methyl-propan-1-ol in 60 ml dichloromethane added. The mixture was allowed to stir at ambient temperature for 16 h. The off-white suspension was diluted with water, the aqueous phase evaporated and the organic phase extracted 3 times with ethyl acetate. The combined organic layers were dried over Na$_2$SO$_4$, filtered and concentrated. The crude product, 33.2 g N-(2-hydroxy-1,1-dimethyl-ethyl)-2-methoxy-4-trifluoro-methyl-benzamide, a light yellow oil was dissolved in 220 ml dichloromethane and cooled to 0° C. Then 24.7 ml (340 mmol) thionyl chloride was added drop-wise and the resulting light yellow solution stirred at ambient temperature for 16 h. Then the pH was adjusted to 10 by addition of saturated aqueous Na$_2$CO$_3$ solution. The aqueous layer was separated and extracted 3 times with tert-butyl methyl ether. The combined organic phases were washed twice with brine, dried over Na$_2$SO$_4$, filtered and concentrated to provide the title compound as light yellow oil which was used without further purification. MS (m/e): 274.1 (M+H$^+$).

b) step 2: 2-(2-Methoxy-3-methyl-4-trifluoromethyl-phenyl)-4,4-dimethyl-4,5-dihydro-oxazole

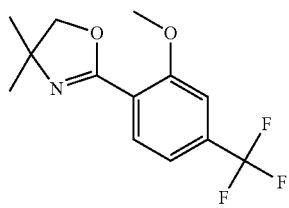 [SMILES: COc1cc(C(F)(F)F)ccc1C1=NC(C)(C)CO1]

To a solution of 5.465 g (20 mmol) 2-(2-methoxy-4-trifluoromethyl-phenyl)-4,4-dimethyl-4,5-dihydro-oxazole in 60 ml dry THF were added at <−60° C. 11.0 ml (22 mmol) lithium diisopropylamide solution 2M in THF/heptanes/ethylbenzene and the mixture stirred for 1.5 h at <−60° C. To the resulting dark brown solution were added 2.5 ml (40 mmol) iodomethane drop wise over 10 min (exothermal, Ti<−48° C.). The resulting light brown solution was stirred at <−50° C. for 2.5 h then quenched with sat. aq. NH$_4$Cl solution and extracted three times with tert-butyl methyl ether. The combined organic phases were washed 3× with brine, dried over Na$_2$SO$_4$, filtered and evaporated: 7.002 g yellow solid: which was purified by flash-chromatography on silica gel with heptane and 5 to 10% AcOEt over 25 min and heptane/AcOEt 90:10 for 20 min to provide the title compound as a light yellow oil. MS (m/e): 288.12 (M+H$^+$).

c) step 3: 2-(2-Ethyl-3-methyl-4-trifluoromethyl-phenyl)-4,4-dimethyl-4,5-dihydro-oxazole

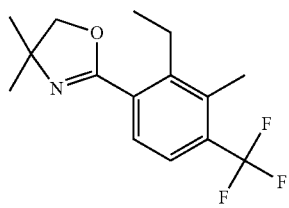 [SMILES: CCc1c(C2=NC(C)(C)CO2)ccc(C(F)(F)F)c1C]

To a cooled solution of 355 mg (1.17 mmol) 2-(2-methoxy-3-methyl-4-trifluoromethyl-phenyl)-4,4-dimethyl-4,5-dihydro-oxazole in 4 ml THF were added at <10° C. drop-wise over 20 min 2.35 ml (4.7 mmol) 2M ethylmagnesium chloride solution in THF. The resulting brown solution was stirred at ambient temperature for 1 h, then quenched with saturated aqueous NH$_4$Cl solution (cooling with ice bath) and extracted three times with tert-butyl methyl ether. The combined organic phases were washed three times with brine, dried over Na$_2$SO$_4$, filtered and evaporated. 2-(2-Ethyl-3-methyl-4-trifluoromethyl-phenyl)-4,4-dimethyl-4,5-dihydro-oxazole was obtained as yellow oil: MS (ISP): 286.1 ((M+H)$^+$.).

d) step 4: 2-(2-Ethyl-3-methyl-4-trifluoromethyl-phenyl)-3,4,4-trimethyl-4,5-dihydro-oxazol-3-ium iodide

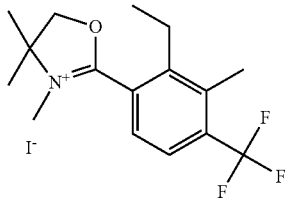 [SMILES: CCc1c(C2=[N+](C)C(C)(C)CO2)ccc(C(F)(F)F)c1C ; [I-]]

To a solution of 837 mg (2.9 mmol) 2-(2-ethyl-3-methyl-4-trifluoromethyl-phenyl)-4,4-dimethyl-4,5-dihydro-oxazole in 8 ml nitromethane were added 1.47 ml (23.5 mmol) methyl iodide and the mixture heated in a sealed tube to 70° C. for 18 h. The brown solution was diluted with tert-butyl methyl ether, the suspension filtered and the precipitate washed with tert-butyl methyl ether and dried. 2-(2-Ethyl-3-methyl-4-trifluoromethyl-phenyl)-3,4,4-trimethyl-4,5-dihydro-oxazol-3-ium iodide was obtained as colourless solid: MS (ISP): 300.1 (M$^+$.).

e) step 5:
2-Ethyl-3-methyl-4-trifluoromethyl-benzoic acid

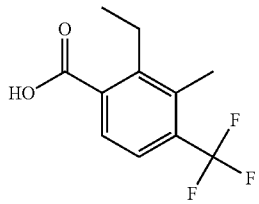

A solution of 960 mg (2.25 mmol) 2-(2-ethyl-3-methyl-4-trifluoromethyl-phenyl)-3,4,4-trimethyl-4,5-dihydro-oxazol-3-ium iodide in 10 ml MeOH and 5 ml 20% NaOH was heated to 70° C. for 17 h The yellow solution was cooled to rt, MeOH distilled off, the residue acidified with conc. HCl to pH 1 and extracted three times with tert-butyl methyl ether. The combined organic phases were washed twice with brine, dried over Na$_2$SO$_4$, filtered and evaporated: 2-Ethyl-3-methyl-4-trifluoromethyl-benzoic acid was obtained as yellow solid: MS (ISN): 231.06 ((M−H)$^-$.).

f) step 6:
2-Ethyl-3-methyl-4-trifluoromethyl-benzoyl chloride

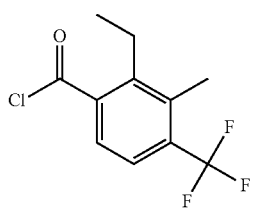 [SMILES: CCc1c(C(=O)Cl)ccc(C(F)(F)F)c1C]

In analogy to the procedure described for the synthesis of example B.6, the title compound was prepared from 2-Ethyl-3-methyl-4-trifluoromethyl-benzoic acid.

Example C.1

Preparation of N-(1,6-Dimethyl-3-phenyl-piperidin-3-yl)-2-methoxy-6-methylsulfanyl-4-trifluoromethyl-benzamide

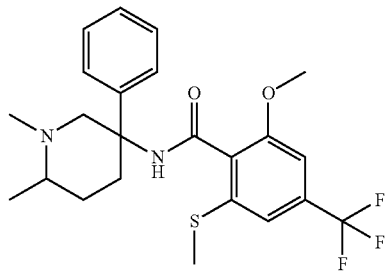

a) step 1:
(3-Hydroxy-1-methyl-propyl)-methyl-carbamic acid tert-butyl ester

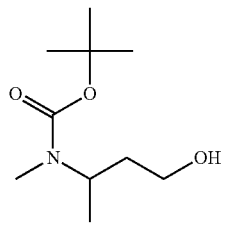

To a solution of 2 g (19.39 mmol) 3-(methylamino)-1-butanol (commercial, CAS: 89585-18-2) in 15 ml dichloromethane under nitrogen at room temperature, was added 3.24 ml (23.27 mmol) triethylamine. The reaction mixture was cooled to 0° C. and a solution of 5.13 g (23.27 mmol) di-tert-butyl dicarbonate in 5 ml dichloromethane was added dropwise. The reaction mixture was stirred at room temperature for 2 days, then quenched with a saturated solution of sodium bicarbonate. The organic layer was dried over sodium sulfate, filtered and concentrated in vacuo. The residue was purified on silica (Eluent: heptane/ethyl acetate 0 to 40%) to provide 3.3 g (84%) of the title compound as a colorless oil. MS (m/e): 204.3 (M+H).

b) step 2:
(3-Bromo-1-methyl-propyl)-methyl-carbamic acid tert-butyl ester

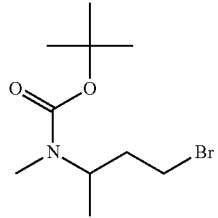

To a solution of 1 g (4.919 mmol) (3-hydroxy-1-methyl-propyl)-methyl-carbamic acid tert-butyl ester in 12.5 ml dichloromethane under nitrogen at 0° C., was added 1.46 g (5.411 mmol) triphenylphosphine, followed by a solution of 1.79 g (5.411 mmol) carbone tetrabromide in 3.5 ml dichloromethane. The reaction mixture was stirred at room temperature for 3 hours. The suspension was concentrated in vacuo. The residue was purified on silica (Eluent: heptane/ethyl acetate 0 to 15%) to provide 0.74 g (57%) of the title compound as a colorless oil.

MS (m/e): 210.1 (M-56).

c) step 3: Methyl-(1-methyl-4-nitro-4-phenyl-butyl)-carbamic acid tert-butyl ester

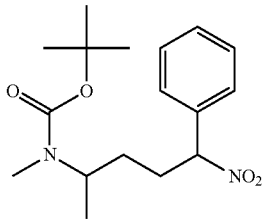 [SMILES: CC(CCC(c1ccccc1)[N+](=O)[O-])N(C)C(=O)OC(C)(C)C]

To a −78° C. solution of 304 mg (2.219 mmol) nitromethylbenzene (CAS: 622-42-4) in 5 ml tetrahydrofuran over mol-sieve and 1.29 ml HMPA, was added dropwise 2.91 ml (4.654 mmol) n-BuLi (1.6 M in hexane). After 45 minutes at −78° C., a solution of 590.7 mg (2.219 mmol) (3-bromo-1-methylpropyl)-methyl-carbamic acid tert-butyl ester in 1.5 ml tetrahydrofuran over mol-sieve was added dropwise. After 1 hour at −78° C., the reaction mixture was allowed to warm up slowly, during 2 hours, to −15° C. The mixture was then cooled again to −78° C. and quenched with 0.75 ml of acetic acid, then with 13 ml saturated ammonium chloride. Back to room temperature, the aqueous phase was extracted two times with ethylacetate. The combined organic layers were dried over sodium sulfate, filtered and concentrated in vacuo. The residue was purified on silica (Eluent: heptane/ethyl acetate 0 to 10%) to provide 201 mg (28%) of the title compound as a colorless oil. MS (m/e): 323.3 (M+H).

d) step 4: Methyl-(1-methyl-4-nitro-4-phenyl-butyl)-amine

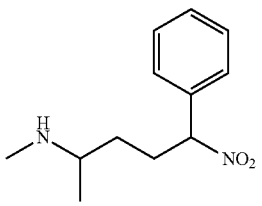 [SMILES: CNC(C)CCC(c1ccccc1)[N+](=O)[O-]]

In analogy to the procedure described for the synthesis of example A.22, step 4, the title compound was prepared from Methyl-(1-methyl-4-nitro-4-phenyl-butyl)-carbamic acid tert-butyl ester. MS (m/e): 223.3 (M+H).

e) step 5: 1,2-Dimethyl-5-nitro-5-phenyl-piperidine

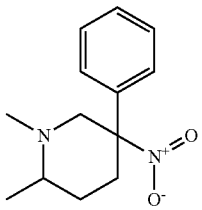 [SMILES: CC1CCC(c2ccccc2)([N+](=O)[O-])CN1C]

To a suspension of 138 mg (0.621 mmol) Methyl-(1-methyl-4-nitro-4-phenyl-butyl)-amine in 2.2 ml dioxane under argon at room temperature, was added 49.8 ul (0.683 mmol) formaldehyde (37% in water). The mixture was stirred at room temperature for 30 minutes and then at 65° C. for 4.5 hours. The mixture was cooled to room temperature and diluted with ethyl acetate. Sodium sulfate was added. The mixture was filtered and the filtrate was concentrated in vacuo. The residue was purified on silica (Eluent: heptane/ethyl acetate 0 to 20%) to provide 76 mg (52%) of the title compound as a colorless oil. MS (m/e): 235.3 (M+H).

f) step 6: 1,6-Dimethyl-3-phenyl-piperidin-3-ylamine

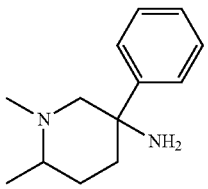

In analogy to the procedure described for the synthesis of example A.17, step 4, the title compound was prepared from 1,2-Dimethyl-5-nitro-5-phenyl-piperidine. MS (m/e): 205.3 (M+H).

g) step 7: N-(1,6-Dimethyl-3-phenyl-piperidin-3-yl)-2-methoxy-6-methylsulfanyl-4-trifluoromethyl-benzamide In analogy to the procedure described for the synthesis of example 16, the title compound was prepared from 1,6-Dimethyl-3-phenyl-piperidin-3-ylamine and 2-Methoxy-6-methylsulfanyl-4-trifluoromethyl-benzoyl chloride (Example B.6). MS (m/e): 453.2 (M+H).

Example C.2

Preparation of N-((3RS,5SR)-1,5-Dimethyl-3-phenyl-piperidin-3-yl)-2-ethyl-4-trifluoromethyl-benzamide

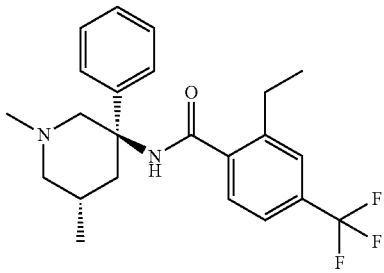 [SMILES: CCc1cc(C(F)(F)F)ccc1C(=O)N[C@@]1(c2ccccc2)C[C@H](C)CN(C)C1]

In analogy to the procedure described for the synthesis of example 1, the title compound was prepared from (3RS,5SR)-

1,5-Dimethyl-3-phenyl-piperidin-3-ylamine (Example A.20) and 2-Ethyl-4-trifluoromethyl-benzoic acid (CAS: 854531-63-8). MS (m/e): 405.4 (M+H).

Description of Active Examples

Example 1 rac-2-Chloro-N-(1-methyl-3-phenyl-piperidin-3-yl)-3-trifluoromethyl-benzamide

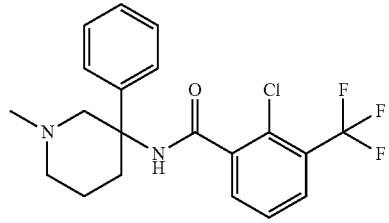 [SMILES: CN1CCCC(NC(=O)c2cccc(C(F)(F)F)c2Cl)(c2ccccc2)C1]

To a solution of 33 mg (0.144 mmol) 2-chloro-3-(trifluoromethyl)benzoic acid (commercial), 75 mg (0.197 mmol) HATU and 90 ul (0.524 mmol) N-ethyldiisopropylamine in DMF (1 ml) was added a solution of 25 mg (0.131 mmol) rac-1-methyl-3-phenyl-piperidin-3-ylamine (Example A.1) in DMF (0.25 ml). The mixture was stirred at room temperature for 22 hours. The solvent was removed in vacuo. The residue was dissolved in ethyl acetate. The solution was washed once with water and twice with a saturated sodium carbonate solution. The aqueous layer was extracted once with ethyl acetate. The combined extracts were dried over sodium sulfate, filtered and concentrated in vacuo. The crude product was purified on silica gel (Eluent: Heptane/ethyl acetate 0 to 100%) to provide 27 mg (52%) of the title compound as a light yellow oil. MS (m/e): MS (m/e): 397.2 (M+H)

In analogy to Example 1, compounds 2 to 15 of the following table were prepared from the acid derivatives and piperidine derivatives:

| Ex No. | Structure | Systematic Name | Starting materials | MW found (MH+) |
|---|---|---|---|---|
| 2 | 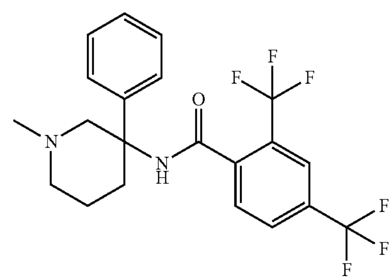 [SMILES: CN1CCCC(NC(=O)c2ccc(C(F)(F)F)cc2C(F)(F)F)(c2ccccc2)C1] | rac-N-(1-Methyl-3-phenyl-piperidin-3-yl)-2,4-bis-trifluoromethyl-benzamide | rac-1-Methyl-3-phenyl-piperidin-3-ylamine (Example A.1) and 2,4-bis(trifluoromethyl)benzoic acid (commercial) | 431.3 |
| 3 | 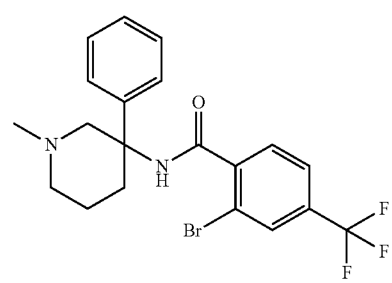 [SMILES: CN1CCCC(NC(=O)c2ccc(C(F)(F)F)cc2Br)(c2ccccc2)C1] | rac-2-Bromo-N-(1-methyl-3-phenyl-piperidin-3-yl)-4-trifluoromethyl-benzamide | rac-1-Methyl-3-phenyl-piperidin-3-ylamine (Example A.1) and 2-Bromo-4-trifluoromethyl-benzoic acid (CAS: 328-89-2) | 441.2 |
| 4 | 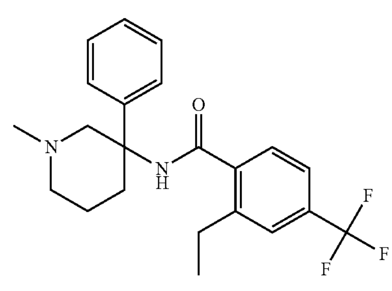 [SMILES: CCc1cc(C(F)(F)F)ccc1C(=O)NC1(c2ccccc2)CCCN(C)C1] | rac-2-Ethyl-N-(1-methyl-3-phenyl-piperidin-3-yl)-4-trifluoromethyl-benzamide | rac-1-Methyl-3-phenyl-piperidin-3-ylamine (Example A.1) and 2-Ethyl-4-trifluoromethyl-benzoic acid (CAS: 854531-63-8) | 391.2 |
| 5 | 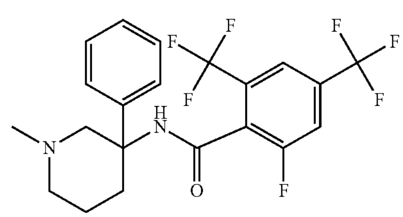 [SMILES: CN1CCCC(NC(=O)c2c(F)cc(C(F)(F)F)cc2C(F)(F)F)(c2ccccc2)C1] | rac-2-Fluoro-N-(1-methyl-3-phenyl-piperidin-3-yl)-4,6-bis-trifluoromethyl-benzamide | rac-1-Methyl-3-phenyl-piperidin-3-ylamine (Example A.1) and 2-fluoro-4,6-bis(trifluoromethyl)benzoic acid (commercial) | 449.2 |

-continued

| Ex No. | Structure | Systematic Name | Starting materials | MW found (MH+) |
|---|---|---|---|---|
| 6 | 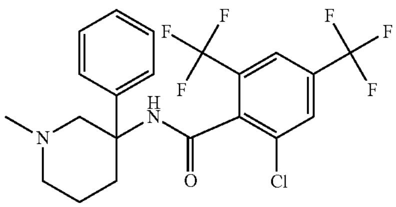 | rac-2-Chloro-N-(1-methyl-3-phenyl-piperidin-3-yl)-4,6-bis-trifluoromethyl-benzamide | rac-1-Methyl-3-phenyl-piperidin-3-ylamine (Example A.1) and 2-chloro-4,6-bis(trifluoromethyl)benzoic acid (commercial) | 465.1 |
| 7 | 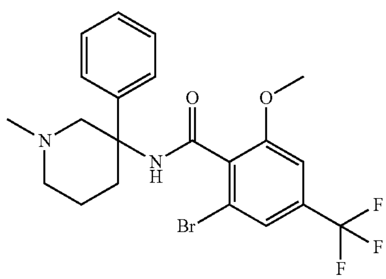 [SMILES: COc1cc(C(F)(F)F)cc(Br)c1C(=O)NC1(c2ccccc2)CCCN(C)C1] | rac-2-Bromo-6-methoxy-N-(1-methyl-3-phenyl-piperidin-3-yl)-4-trifluoromethyl-benzamide | rac-1-Methyl-3-phenyl-piperidin-3-ylamine (Example A.1) and 2-Bromo-6-methoxy-4-trifluoromethyl-benzoic acid (Example B1) | 471.1 |
| 8 | 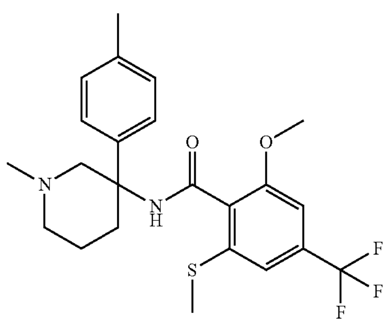 [SMILES: COc1cc(C(F)(F)F)cc(SC)c1C(=O)NC1(c2ccc(C)cc2)CCCN(C)C1] | rac-2-Methoxy-6-methylsulfanyl-N-(1-methyl-3-p-tolyl-piperidin-3-yl)-4-trifluoromethyl-benzamide | rac-1-Methyl-3-p-tolyl-piperidin-3-ylamine (Example A.4) and 2-Methoxy-6-methylsulfanyl-4-trifluoromethyl-benzoic acid (Example B.2) | 453.3 |
| 9 | 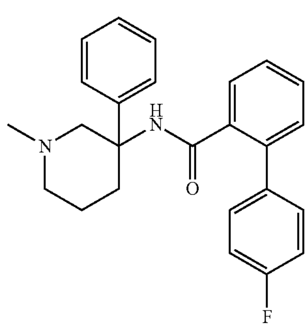 [SMILES: CN1CCCC(NC(=O)c2ccccc2-c2ccc(F)cc2)(c2ccccc2)C1] | rac-4'-Fluoro-biphenyl-2-carboxylic acid (1-methyl-3-phenyl-piperidin-3-yl)-amide | rac-1-Methyl-3-phenyl-piperidin-3-ylamine (Example A.1) and 4'-fluorobiphenyl-2-carboxylic acid (commercial) | 389.1 |
| 10 | 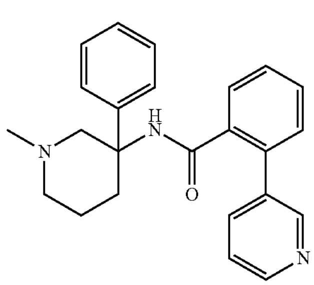 [SMILES: CN1CCCC(NC(=O)c2ccccc2-c2cccnc2)(c2ccccc2)C1] | rac-N-(1-Methyl-3-phenyl-piperidin-3-yl)-2-pyridin-3-yl-benzamide | rac-1-Methyl-3-phenyl-piperidin-3-ylamine (Example A.1) and 2-pyrid-3-yl-benzoic acid (commercial) | 372.2 |

| Ex No. | Structure | Systematic Name | Starting materials | MW found (MH+) |
| --- | --- | --- | --- | --- |
| 11 | 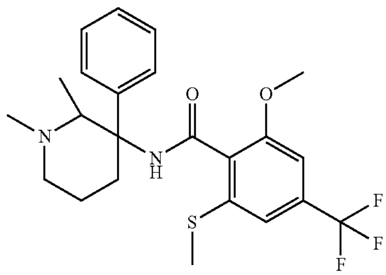 [SMILES: COc1cc(C(F)(F)F)cc(SC)c1C(=O)NC1(c2ccccc2)CCCN(C)C1C] | rac-N-(1,2-Dimethyl-3-phenyl-piperidin-3-yl)-2-methoxy-6-methylsulfanyl-4-trifluoromethyl-benzamide | rac-1,2-Dimethyl-3-phenyl-piperidin-3-ylamine (Example A.5) and 2-Methoxy-6-methylsulfanyl-4-trifluoromethyl-benzoic acid (Example B.2) | 453.2 |
| 12 | 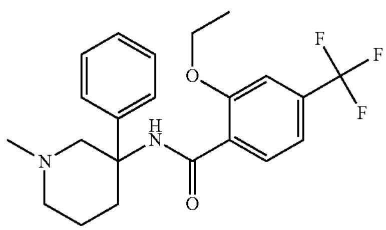 [SMILES: CCOc1cc(C(F)(F)F)ccc1C(=O)NC1(c2ccccc2)CCCN(C)C1] | rac-2-Ethoxy-N-(1-methyl-3-phenyl-piperidin-3-yl)-4-trifluoromethyl-benzamide | rac-1-Methyl-3-phenyl-piperidin-3-ylamine (Example A.1) and 2-Ethoxy-4-trifluoromethyl-benzoic acid (CAS: 334018-39-2) | 407.4 |
| 13 | 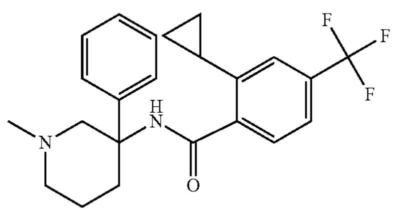 [SMILES: CN1CCCC(NC(=O)c2ccc(C(F)(F)F)cc2C2CC2)(c2ccccc2)C1] | rac-2-Cyclopropyl-N-(1-methyl-3-phenyl-piperidin-3-yl)-4-trifluoromethyl-benzamide | rac-1-Methyl-3-phenyl-piperidin-3-ylamine (Example A.1) and 2-Cyclopropyl-4-trifluoromethyl-benzoic acid (Example B.3) | 403.3 |
| 14 | 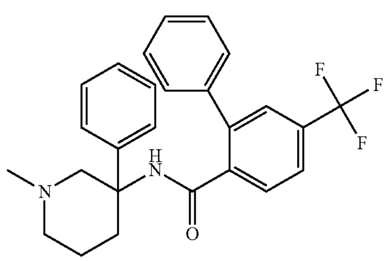 [SMILES: CN1CCCC(NC(=O)c2ccc(C(F)(F)F)cc2-c2ccccc2)(c2ccccc2)C1] | rac-5-Trifluoromethyl-biphenyl-2-carboxylic acid (1-methyl-3-phenyl-piperidin-3-yl)-amide | rac-1-Methyl-3-phenyl-piperidin-3-ylamine (Example A.1) and 5-Trifluoromethyl-biphenyl-2-carboxylic acid (Example B.4) | 439.4 |
| 15 | 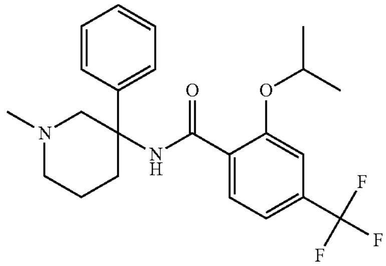 [SMILES: CC(C)Oc1cc(C(F)(F)F)ccc1C(=O)NC1(c2ccccc2)CCCN(C)C1] | rac-2-Isopropoxy-N-(1-methyl-3-phenyl-piperidin-3-yl)-4-trifluoromethyl-benzamide | rac-1-Methyl-3-phenyl-piperidin-3-ylamine (Example A.1) and 2-Isopropoxy-4-trifluoromethyl-benzoic acid (Example B.5) | 421.2 |

Example 16 rac-2-Methoxy-N-(1-methyl-3-phenyl-piperidin-3-yl)-4,6-bis-trifluoromethyl-benzamide

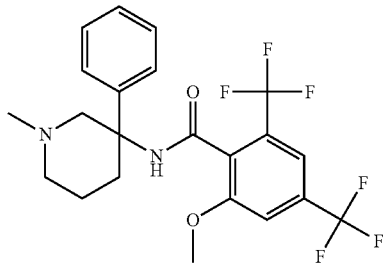 [SMILES: COc1cc(C(F)(F)F)cc(C(F)(F)F)c1C(=O)NC1(c2ccccc2)CCCN(C)C1]

To a solution of 205 mg (1.077 mmol) rac-1-methyl-3-phenyl-piperidin-3-ylamine (Example A.1) and 369 ul (2.154 mmol) N-ethyldiisopropylamine in dichloromethane (2.5 ml) was added dropwise a solution of 430 mg (1.4 mmol) 2-methoxy-4,6-bis-trifluoromethyl-benzoyl chloride (CAS: 886503-47-5) in dichloromethane (2.0 ml) at room temperature. The mixture was stirred at room temperature for 16 hours. The solvent was removed in vacuo. The crude product was purified on silica gel (Eluent: Heptane/ethyl acetate 0 to 100%) to provide 340 mg (69%) of the title compound as a light yellow foam. MS (m/e): MS (m/e): 461.4 (M+H).

In analogy to Example 16, compounds 17 to 28 of the following table were prepared from the acyl chloride derivatives and piperidine derivatives:

| Ex. No. | Structure | Systematic Name | Starting materials | MW found (MH+) |
|---|---|---|---|---|
| 17 | 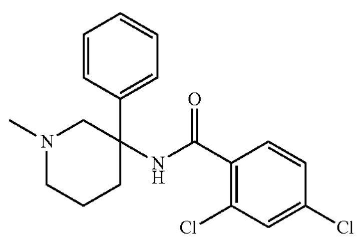 [SMILES: CN1CCCC(NC(=O)c2ccc(Cl)cc2Cl)(c2ccccc2)C1] | rac-2,4-Dichloro-N-(1-methyl-3-phenyl-piperidin-3-yl)-benzamide | rac-1-Methyl-3-phenyl-piperidin-3-ylamine (Example A.1) and 2,4-dichloro-benzoyl chloride (CAS: 98499-66-2) | 363.1 |
| 18 | 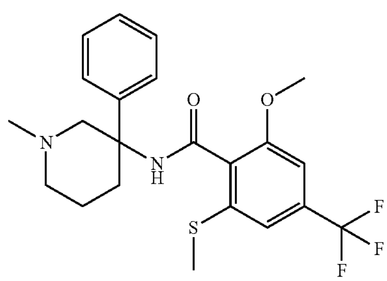 [SMILES: COc1cc(C(F)(F)F)cc(SC)c1C(=O)NC1(c2ccccc2)CCCN(C)C1] | rac-2-Methoxy-N-(1-methyl-3-phenyl-piperidin-3-yl)-6-methylsulfanyl-4-trifluoromethyl-benzamide | rac-1-Methyl-3-phenyl-piperidin-3-ylamine (Example A.1) and 2-Methoxy-6-methylsulfanyl-4-trifluoromethyl-benzoyl chloride (Example B.6) | 439.4 |
| 19 | 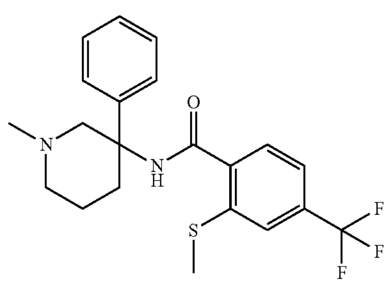 [SMILES: CSc1cc(C(F)(F)F)ccc1C(=O)NC1(c2ccccc2)CCCN(C)C1] | rac-N-(1-Methyl-3-phenyl-piperidin-3-yl)-2-methylsulfanyl-4-trifluoromethyl-benzamide | rac-1-Methyl-3-phenyl-piperidin-3-ylamine (Example A.1) and 2-Methylsulfanyl-4-trifluoromethyl-benzoyl chloride (CAS: 956830-68-5) | 409.3 |
| 20 | 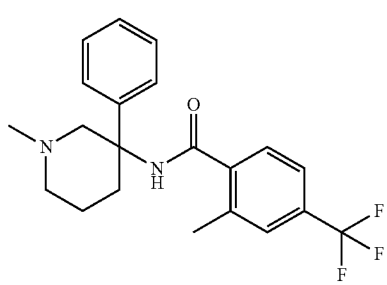 [SMILES: Cc1cc(C(F)(F)F)ccc1C(=O)NC1(c2ccccc2)CCCN(C)C1] | rac-2-Methyl-N-(1-methyl-3-phenyl-piperidin-3-yl)-4-trifluoromethyl-benzamide | rac-1-Methyl-3-phenyl-piperidin-3-ylamine (Example A.1) and 2-Methyl-4-trifluoromethyl-benzoyl chloride (CAS: 98499-66-2) | 377.3 |

-continued

| Ex. No. | Structure | Systematic Name | Starting materials | MW found (MH+) |
|---|---|---|---|---|
| 21 | 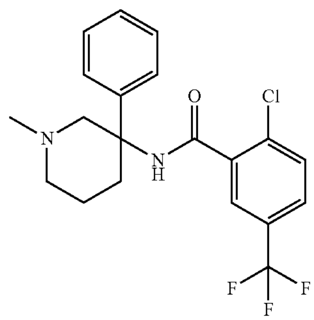 [SMILES: CN1CCCC(NC(=O)c2cc(C(F)(F)F)ccc2Cl)(c2ccccc2)C1] | rac-2-Chloro-N-(1-methyl-3-phenyl-piperidin-3-yl)-5-trifluoromethyl-benzamide | rac-1-Methyl-3-phenyl-piperidin-3-ylamine (Example A.1) and 2-Chloro-5-trifluoromethyl-benzoyl chloride (CAS: 657-05-6) | 397.2 |
| 22 | 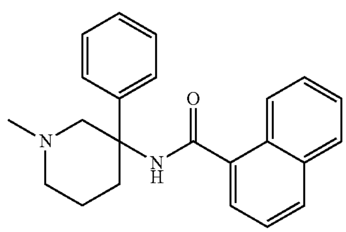 [SMILES: CN1CCCC(NC(=O)c2cccc3ccccc23)(c2ccccc2)C1] | rac-Naphthalene-1-carboxylic acid (1-methyl-3-phenyl-piperidin-3-yl)-amide | rac-1-Methyl-3-phenyl-piperidin-3-ylamine (Example A.1) and 1-Naphthoyl chloride (commercial) | 345.3 |
| 23 | 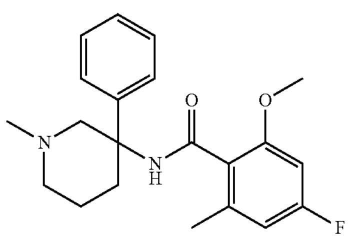 [SMILES: COc1cc(F)cc(C)c1C(=O)NC1(c2ccccc2)CCCN(C)C1] | rac-4-Fluoro-2-methoxy-6-methyl-N-(1-methyl-3-phenyl-piperidin-3-yl)-benzamide | rac-1-Methyl-3-phenyl-piperidin-3-ylamine (Example A.1) and 4-Fluoro-2-methoxy-6-methyl-benzoyl chloride (CAS: 960531-76-4) | 357.4 |
| 24 | 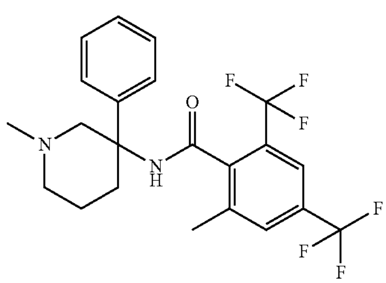 [SMILES: Cc1cc(C(F)(F)F)cc(C(F)(F)F)c1C(=O)NC1(c2ccccc2)CCCN(C)C1] | rac-2-Methyl-N-(1-methyl-3-phenyl-piperidin-3-yl)-4,6-bis-trifluoromethyl-benzamide | rac-1-Methyl-3-phenyl-piperidin-3-ylamine (Example A.1) and 2-Methyl-4,6-bis-trifluoromethyl-benzoyl chloride (CAS: 895580-42-4) | 445.4 |
| 25 | 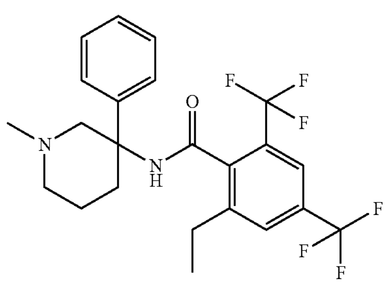 [SMILES: CCc1cc(C(F)(F)F)cc(C(F)(F)F)c1C(=O)NC1(c2ccccc2)CCCN(C)C1] | rac-2-Ethyl-N-(1-methyl-3-phenyl-piperidin-3-yl)-4,6-bis-trifluoromethyl-benzamide | rac-1-Methyl-3-phenyl-piperidin-3-ylamine (Example A.1) and 2-Ethyl-4,6-bis-trifluoromethyl-benzoyl chloride (Example B.7) | 459.4 |

-continued

| Ex. No. | Structure | Systematic Name | Starting materials | MW found (MH+) |
|---|---|---|---|---|
| 26 | 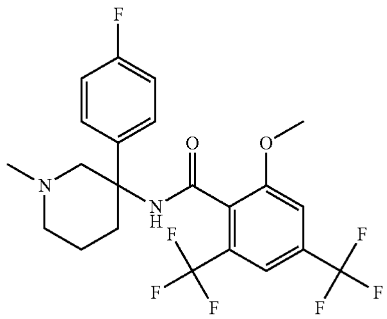 [SMILES: COc1cc(C(F)(F)F)cc(C(F)(F)F)c1C(=O)NC1(c2ccc(F)cc2)CCCN(C)C1] | rac-N-[3-(4-Fluoro-phenyl)-1-methyl-piperidin-3-yl]-2-methoxy-4,6-bis-trifluoromethyl-benzamide | rac-3-(4-Fluoro-phenyl)-1-methyl-piperidin-3-ylamine (Example A.2) and 2-Methoxy-4,6-bis-trifluoromethyl-benzoyl chloride (CAS: 886503-47-5) | 479.1 |
| 27 | 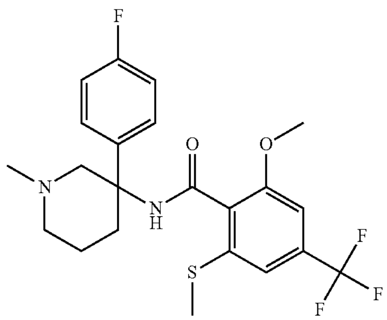 [SMILES: COc1cc(C(F)(F)F)cc(SC)c1C(=O)NC1(c2ccc(F)cc2)CCCN(C)C1] | rac-N-[3-(4-Fluoro-phenyl)-1-methyl-piperidin-3-yl]-2-methoxy-6-methylsulfanyl-4-trifluoromethyl-benzamide | rac-3-(4-Fluoro-phenyl)-1-methyl-piperidin-3-ylamine (Example A.2) and 2-Methoxy-6-methylsulfanyl-4-trifluoromethyl-benzoyl chloride (Example B1) | 457.2 |
| 28 | 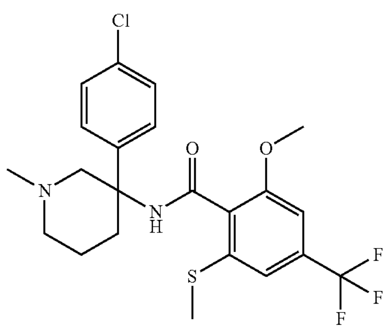 [SMILES: COc1cc(C(F)(F)F)cc(SC)c1C(=O)NC1(c2ccc(Cl)cc2)CCCN(C)C1] | rac-N-[3-(4-Chloro-phenyl)-1-methyl-piperidin-3-yl]-2-methoxy-6-methylsulfanyl-4-trifluoromethyl-benzamide | rac-3-(4-Chloro-phenyl)-1-methyl-piperidin-3-ylamine (Example A.3) and 2-Methoxy-6-methylsulfanyl-4-trifluoromethyl-benzoyl chloride (Example B1) | 473.3 |

Example 29 rac-2-Methoxy-N-(3-phenyl-piperidin-3-yl)-4,6-bis-trifluoromethyl-benzamide

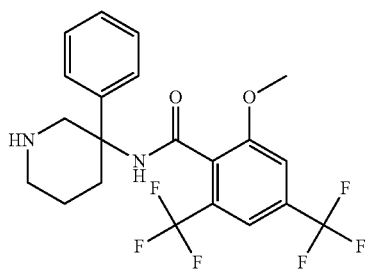 [SMILES: COc1cc(C(F)(F)F)cc(C(F)(F)F)c1C(=O)NC1(c2ccccc2)CCCNC1]

a) step 1:
rac-3-Amino-3-phenyl-piperidine-1-carboxylic acid benzyl ester

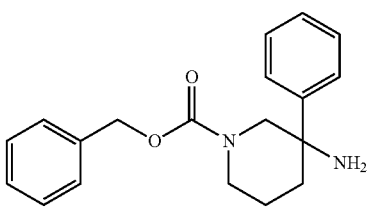 [SMILES: NC1(c2ccccc2)CCCN(C(=O)OCc2ccccc2)C1]

To a refluxing solution of 500 mg (1.486 mmol) rac-3-azido-3-phenyl-piperidine-1-carboxylic acid benzyl ester (example A.1, step 2) and 281 mg (7.43 mmol) NaBH₄ in THF (5 ml) was added dropwise 2.0 ml methanol over 1.5 hour. The mixture was refluxed for another hour and then stirred at room temperature overnight. Another 114 mg (3 mmol) NaBH₄ were added and the mixture was refluxed for 2 hours. The mixture was cooled in an ice bath and acidified with HCl 1N. The mixture was basified with 1N NaOH and extracted three times with ethyl acetate. The combined extracts were dried over sodium sulfate, filtered and concentrated in vacuo. The crude product was purified on silica gel (Eluent: Heptane/ethyl acetate 0 to 100%) to provide 220 mg (48%) of the title compound as a colorless oil. MS (m/e): MS (m/e): 311.4 (M+H).

b) step 2: rac-3-(2-Methoxy-4,6-bis-trifluoromethyl-benzoylamino)-3-phenyl-piperidine-1-carboxylic acid benzyl ester

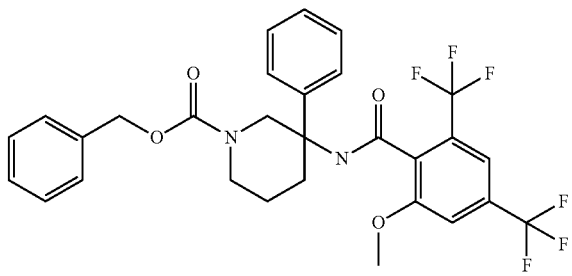 [SMILES: COc1cc(C(F)(F)F)cc(C(F)(F)F)c1C(=O)NC1(c2ccccc2)CCCN(C(=O)OCc2ccccc2)C1]

In analogy to the procedure described for the synthesis of example 16, the title compound was prepared from rac-3-amino-3-phenyl-piperidine-1-carboxylic acid benzyl ester and 2-methoxy-4,6-bis-trifluoromethyl-benzoyl chloride (CAS: 886503-47-5).

c) step 3: rac-2-Methoxy-N-(3-phenyl-piperidin-3-yl)-4,6-bis-trifluoromethyl-benzamide To a solution of 445 mg (0.767 mmol) rac-3-(2-methoxy-4,6-bis-trifluoromethyl-benzoylamino)-3-phenyl-piperidine-1-carboxylic acid benzyl ester in methanol (4.5 ml) were added 44 mg Pd/C 10%. The mixture was stirred under a hydrogen atmosphere at room temperature for 1.5 hour. The apparatus was purged with argon. The catalyst was filtered and the filtrate was concentrated in vacuo to provide 330 mg (96%) of the title compound as a white foam. MS (m/e): 447.3 (M+H).

Example 30 rac-N-(1-Ethyl-3-phenyl-piperidin-3-yl)-2-methoxy-4,6-bis-trifluoromethyl-benzamide

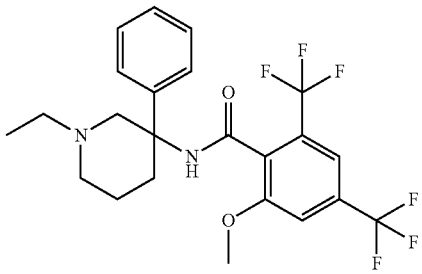

To a solution of 25.mg (0.056 mmol) rac-2-methoxy-N-(3-phenyl-piperidin-3-yl)-4,6-bis-trifluoromethyl-benzamide in 0.25 ml dichloromethane were added 19.7 ul (0.112 mmol) N-ethyldiisopropylamine and finally 6.0 ul (0.0728 mmol) iodoethane. The solution was stirred at room temperature for 20 hours. The solvent was removed in vacuo. The crude product was purified on silica gel (Eluent: Heptane/ethyl acetate 0 to 100%) to provide 15 mg (58%) of the title compound as a colorless oil. MS (m/e): 475.2 (M+H).

Example 31 rac-N-(1-Isopropyl-3-phenyl-piperidin-3-yl)-2-methoxy-4,6-bis-trifluoromethyl-benzamide

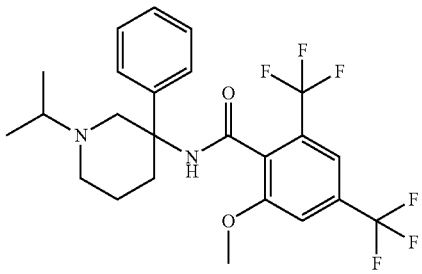 [SMILES: CCN1CCCC(NC(=O)c2c(OC)cc(C(F)(F)F)cc2C(F)(F)F)(c2ccccc2)C1]

To a solution of 35.7 mg (0.08 mmol) rac-2-methoxy-N-(3-phenyl-piperidin-3-yl)-4,6-bis-trifluoromethyl-benzamide in methanol were added 28 ul (0.48 mmol) acetic acid, 59 ul (0.8 mmol) acetone and finally 30 mg (0.4 mmol) sodium cyanoborohydride. The mixture was stirred at room temperature for 4 hours. The solvent was removed in vacuo. The residue was taken in ethyl acetate. The mixture was washed once with a 1N NaOH solution, once with water and once with brine. The aqueous layer was extracted once with ethyl acetate. The combined organic layers were dried over sodium sulfate, filtered and concentrated in vacuo. The crude product was purified on silica gel (Eluent: Heptane/ethyl acetate 0 to 100%) to provide 33 mg (85%) of the title compound as a white foam. MS (m/e): 489.4 (M+H).

In analogy to Example 31, compounds 32 to 34 of the following table were prepared from rac-2-methoxy-N-(3-phenyl-piperidin-3-yl)-4,6-bis-trifluoromethyl-benzamide and carbonyl derivatives:

| Ex. No. | Structure | Systematic Name | Starting materials | MW found (MH+) |
|---|---|---|---|---|
| 32 | 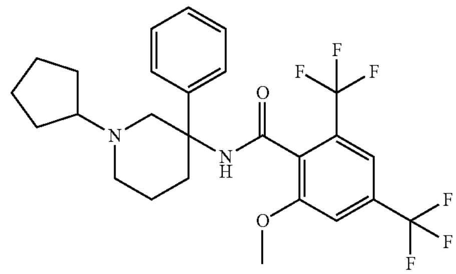 [SMILES: COc1cc(C(F)(F)F)cc(C(F)(F)F)c1C(=O)NC1(c2ccccc2)CCCN(C2CCCC2)C1] | rac-N-(1-Cyclopentyl-3-phenyl-piperidin-3-yl)-2-methoxy-4,6-bis-trifluoromethyl-benzamide | cyclopentanone | 515.5 |
| 33 | 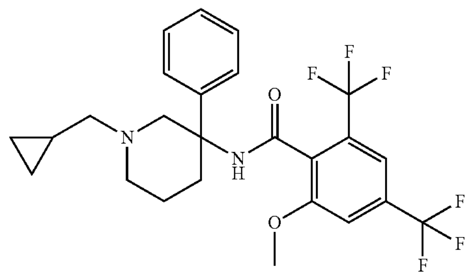 [SMILES: COc1cc(C(F)(F)F)cc(C(F)(F)F)c1C(=O)NC1(c2ccccc2)CCCN(CC2CC2)C1] | rac-N-(1-Cyclopropylmethyl-3-phenyl-piperidin-3-yl)-2-methoxy-4,6-bis-trifluoromethyl-benzamide | cyclopropanecarbox-aldehyde | 501.3 |
| 34 | 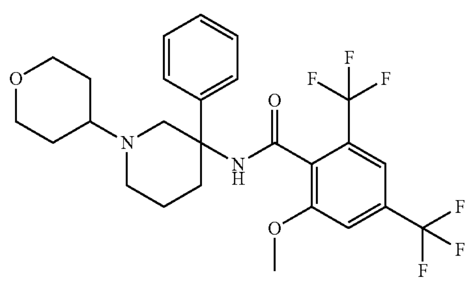 [SMILES: COc1cc(C(F)(F)F)cc(C(F)(F)F)c1C(=O)NC1(c2ccccc2)CCCN(C2CCOCC2)C1] | rac-2-Methoxy-N-[3-phenyl-1-(tetrahydro-pyran-4-yl)-piperidin-3-yl]-4,6-bis-trifluoromethyl-benzamide | tetrahydro-4H-pyran-4-one | 531.3 |

The examples 35-38 have been prepared by separation of the racemic material by chiral HPLC:

| Ex No. | Structure | Systematic Name | Starting racemic material | Retent. time (min.)* | MW found (MH+) |
|---|---|---|---|---|---|
| 35 | 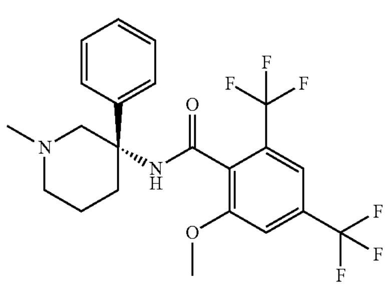 [SMILES: COc1cc(C(F)(F)F)cc(C(F)(F)F)c1C(=O)N[C@]1(c2ccccc2)CCCN(C)C1] | 2-Methoxy-N-((S)-1-methyl-3-phenyl-piperidin-3-yl)-4,6-bis-trifluoromethyl-benzamide | rac-2-Methoxy-N-(1-methyl-3-phenyl-piperidin-3-yl)-4,6-bis-trifluoromethyl-benzamide (Example 16) | 5.4 | 461.4 |

-continued

| Ex No. | Structure | Systematic Name | Starting racemic material | Retent. time (min.)* | MW found (MH+) |
|---|---|---|---|---|---|
| 36 | 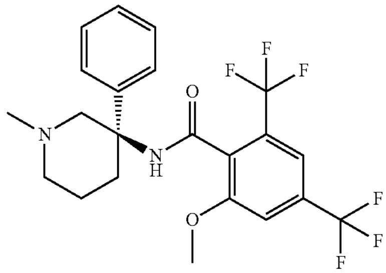 [SMILES: COc1cc(C(F)(F)F)cc(C(F)(F)F)c1C(=O)N[C@@]1(c2ccccc2)CCCN(C)C1] | 2-Methoxy-N-((R)-1-methyl-3-phenyl-piperidin-3-yl)-4,6-bis-trifluoromethyl-benzamide | rac-2-Methoxy-N-(1-methyl-3-phenyl-piperidin-3-yl)-4,6-bis-trifluoromethyl-benzamide (Example 16) | 10.3 | 461.4 |
| 37 | 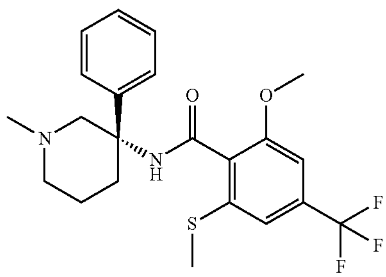 [SMILES: COc1cc(C(F)(F)F)cc(SC)c1C(=O)N[C@]1(c2ccccc2)CCCN(C)C1] | 2-Methoxy-N-((S)-1-methyl-3-phenyl-piperidin-3-yl)-6-methylsulfanyl-4-trifluoromethyl-benzamide hydrochloride | rac-2-Methoxy-N-(1-methyl-3-phenyl-piperidin-3-yl)-6-methylsulfanyl-4-trifluoromethyl-benzamide (Example 18) | 7.3 | 439.3 |
| 38 | 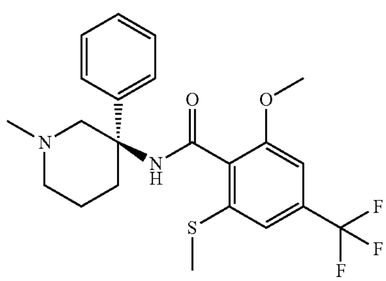 [SMILES: COc1cc(C(F)(F)F)cc(SC)c1C(=O)N[C@@]1(c2ccccc2)CCCN(C)C1] | 2-Methoxy-N-((R)-1-methyl-3-phenyl-piperidin-3-yl)-6-methylsulfanyl-4-trifluoromethyl-benzamide hydrochloride | rac-2-Methoxy-N-(1-methyl-3-phenyl-piperidin-3-yl)-6-methylsulfanyl-4-trifluoromethyl-benzamide (Example 18) | 14.1 | 439.3 |

*Analytical separation conditions: Column: Chiralpak AD; Eluent: 15% Isopropanol/Heptane; flow 35 ml, UV detection: 254 nm In analogy to Example 1, compounds 39 to 44 of the following table were prepared from the acid derivatives and piperidine derivatives:

| Ex No. | Structure | Systematic Name | Starting materials | MW found (MH+) |
|---|---|---|---|---|
| 39 | 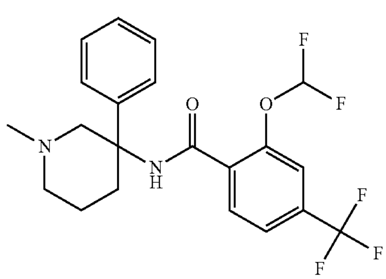 | rac-2-Difluoromethoxy-N-(1-methyl-3-phenyl-piperidin-3-yl)-4-trifluoromethyl-benzamide | rac-1-Methyl-3-phenyl-piperidin-3-ylamine (Example A.1) and 2-Difluoromethoxy-4-trifluoromethyl-benzoic acid (Example B.8) | 429.2 |

| Ex No. | Structure | Systematic Name | Starting materials | MW found (MH+) |
|---|---|---|---|---|
| 40 | 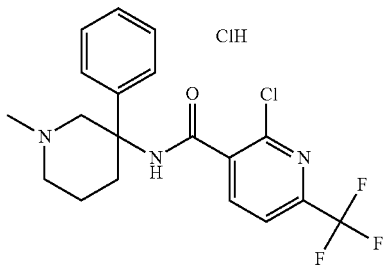 [SMILES: CN1CCCC(NC(=O)c2ccc(C(F)(F)F)nc2Cl)(c2ccccc2)C1 ; Cl] | rac-2-Chloro-N-(1-methyl-3-phenyl-piperidin-3-yl)-6-trifluoromethyl-nicotinamide hydrochloride | rac-1-Methyl-3-phenyl-piperidin-3-ylamine (Example A.1) and 2-chloro-6-(trifluoromethyl) nicotinic acid (commercial) | 398.1 |
| 41 | 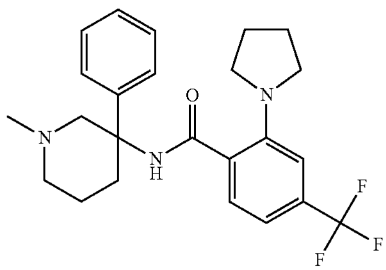 [SMILES: CN1CCCC(NC(=O)c2ccc(C(F)(F)F)cc2N2CCCC2)(c2ccccc2)C1] | rac-2-Chloro-N-(1-methyl-3-phenyl-piperidin-3-yl)-6-trifluoromethyl-nicotinamide hydrochloride | rac-1-Methyl-3-phenyl-piperidin-3-ylamine (Example A.1) and 2-Pyrrolidin-1-yl-4-trifluoromethyl-benzoic acid (Example B.9) | 432.4 |
| 42 | 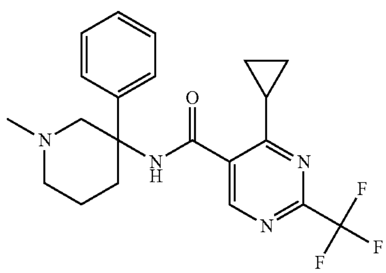 [SMILES: CN1CCCC(NC(=O)c2cnc(C(F)(F)F)nc2C2CC2)(c2ccccc2)C1] | rac-4-Cyclopropyl-2-trifluoromethyl-pyrimidine-5-carboxylic acid (1-methyl-3-phenyl-piperidin-3-yl)-amide | rac-1-Methyl-3-phenyl-piperidin-3-ylamine (Example A.1) and 4-cyclopropyl-2-trifluoromethyl-pyrimidine-5-carboxylic acid (commercial) | 405.4 |
| 43 | 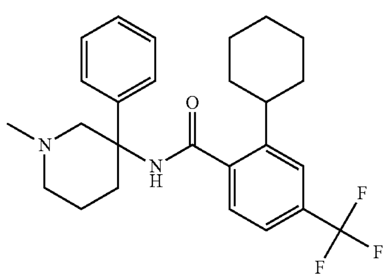 [SMILES: CN1CCCC(NC(=O)c2ccc(C(F)(F)F)cc2C2CCCCC2)(c2ccccc2)C1] | rac-2-Cyclohexyl-N-(1-methyl-3-phenyl-piperidin-3-yl)-4-trifluoromethyl-benzamide | rac-1-Methyl-3-phenyl-piperidin-3-ylamine (Example A.1) and 2-Cyclohexyl-4-trifluoromethyl-benzoic acid (Example B.10) | 445.4 |
| 44 | 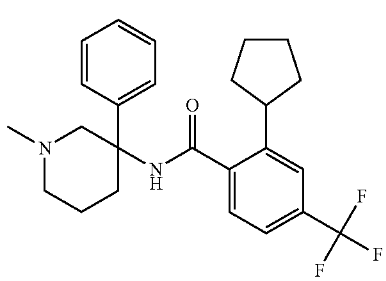 | rac-2-Cyclopentyl-N-(1-methyl-3-phenyl-piperidin-3-yl)-4-trifluoromethyl-benzamide | rac-1-Methyl-3-phenyl-piperidin-3-ylamine (Example A.1) and 2-Cyclopentyl-4-trifluoromethyl-benzoic acid (Example B.11) | 431.3 |

In analogy to Example 16, compounds 45 to 48 of the following table were prepared from the acyl chloride derivatives and piperidine derivatives:

| Ex. No. | Structure | Systematic Name | Starting materials | MW found (MH+) |
|---|---|---|---|---|
| 45 | 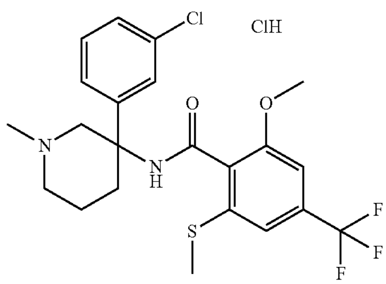 [SMILES: COc1cc(C(F)(F)F)cc(SC)c1C(=O)NC1(c2cccc(Cl)c2)CCCN(C)C1 ; Cl] | rac-N-[3-(3-Chloro-phenyl)-1-methyl-piperidin-3-yl]-2-methoxy-6-methylsulfanyl-4-trifluoromethyl-benzamide hydrochloride | rac-3-(3-Chloro-phenyl)-1-methyl-piperidin-3-ylamine (Example A.6) and 2-Methoxy-6-methylsulfanyl-4-trifluoromethyl-benzoyl chloride (Example B6) | 473.2 |
| 46 | 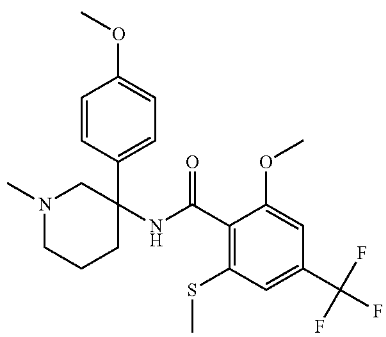 [SMILES: COc1ccc(C2(NC(=O)c3c(OC)cc(C(F)(F)F)cc3SC)CCCN(C)C2)cc1] | rac-2-Methoxy-N-[3-(4-methoxy-phenyl)-1-methyl-piperidin-3-yl]-6-methylsulfanyl-4-trifluoromethyl-benzamide | rac-3-(4-Methoxy-phenyl)-1-methyl-piperidin-3-ylamine (Example A.7) and 2-Methoxy-6-methylsulfanyl-4-trifluoromethyl-benzoyl chloride (Example B6) | 469.2 |
| 47 | 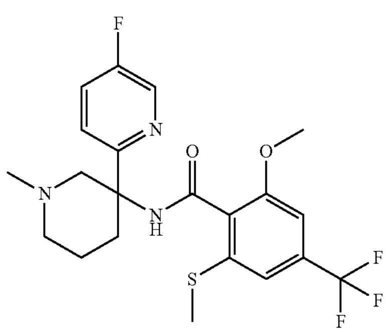 [SMILES: COc1cc(C(F)(F)F)cc(SC)c1C(=O)NC1(c2ccc(F)cn2)CCCN(C)C1] | rac-N-(5-Fluoro-1'-methyl-1',4',5',6'-tetrahydro-2'H-[2,3']bipyridinyl-3'-yl)-2-methoxy-6-methylsulfanyl-4-trifluoromethyl-benzamide | rac-5-Fluoro-1'-methyl-1',4',5',6'-tetrahydro-2H-[2,3']bipyridinyl-3'-ylamine (Example A.8) and 2-Methoxy-6-methylsulfanyl-4-trifluoromethyl-benzoyl chloride (Example B6) | 458.2 |
| 48 | 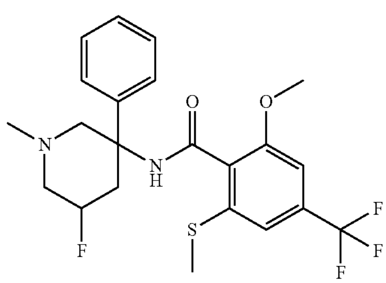 | rac-N-(5-Fluoro-1-methyl-3-phenyl-piperidin-3-yl)-2-methoxy-6-methylsulfanyl-4-trifluoromethyl-benzamide | rac-5-Fluoro-1-methyl-3-phenyl-piperidin-3-ylamine (Example A.9) and 2-Methoxy-6-methylsulfanyl-4-trifluoromethyl-benzoyl chloride (Example B6) | 457.2 |

Example 49 rac-2-Cyclopropyl-N-(3-phenyl-piperidin-3-yl)-4-trifluoromethyl-benzamide

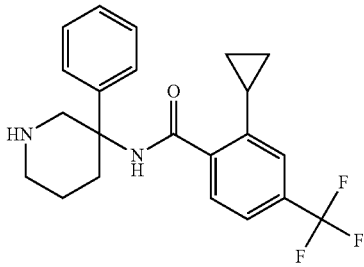 [SMILES: O=C(NC1(c2ccccc2)CCCNC1)c1ccc(C(F)(F)F)cc1C1CC1]

In analogy to the procedure described for the synthesis of example 29, the title compound was prepared from rac-3-amino-3-phenyl-piperidine-1-carboxylic acid benzyl ester and 2-cyclopropyl-4-trifluoromethyl-benzoic acid (Example B.3). MS (m/e): 389.1 (MH+).

Example 50 rac-2-Methoxy-6-methylsulfanyl-N-(3-phenyl-piperidin-3-yl)-4-trifluoromethyl-benzamide hydrochloride

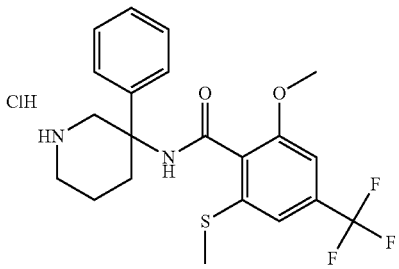 [SMILES: Cl ; COc1cc(C(F)(F)F)cc(SC)c1C(=O)NC1(c2ccccc2)CCCNC1]

a) step 1: rac-3-(2-Methoxy-6-methylsulfanyl-4-trifluoromethyl-benzoylamino)-3-phenyl-piperidine-1-carboxylic acid benzyl ester

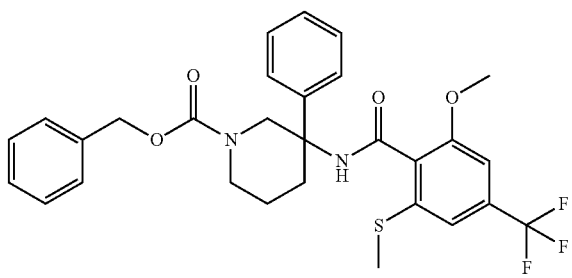 [SMILES: COc1cc(C(F)(F)F)cc(SC)c1C(=O)NC1(c2ccccc2)CCCN(C(=O)OCc2ccccc2)C1]

In analogy to the procedure described for the synthesis of example 16, the title compound was prepared from rac-3-amino-3-phenyl-piperidine-1-carboxylic acid benzyl ester (example 29, step 1) and 2-methoxy-6-methylsulfanyl-4-trifluoromethyl-benzoyl chloride (Example B.6).
MS (m/e): 559.1 (MH+)

b) step 2: rac-2-Methoxy-6-methylsulfanyl-N-(3-phenyl-piperidin-3-yl)-4-trifluoromethyl-benzamide hydrochloride To a solution of 50 mg (0.0895 mmol) rac-3-(2-methoxy-6-methylsulfanyl-4-trifluoromethyl-benzoylamino)-3-phenyl-piperidine-1-carboxylic acid benzyl ester in 1 ml ethanol under argon at room temperature, were added 57 mg (0.895 mmol) ammonium formate and 50 mg Pd/C 10%. The mixture was refluxed for 20 minutes, filtered and the filtrate was concentrated in vacuo. The residue was taken in water. The aqueous layer was basified with a 2M $Na_2CO_3$ solution and extracted 3 times with dichloromethane. The combined extracts were dried over sodium sulfate, filtered and concentrated in vacuo. The crude product was purified on silica gel (Eluent: heptane/ethyl acetate 0 to 100%) to provide 13.4 mg of product which was dissolved in methanol. The solution was acidified with a 1.6M HCl/methanol solution. The solvent was removed in vacuo to provide 13 mg of the title compound as a light yellow solid. MS (m/e): 425.1 (MH+).

Example 51 rac-N-(5-Hydroxy-1-methyl-3-phenyl-piperidin-3-yl)-2-methoxy-6-methylsulfanyl-4-trifluoromethyl-benzamide

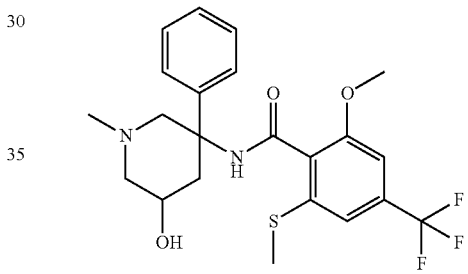

a) step 1: rac-2-Methoxy-N-(5-methoxymethoxy-1-methyl-3-phenyl-piperidin-3-yl)-6-methylsulfanyl-4-trifluoromethyl-benzamide

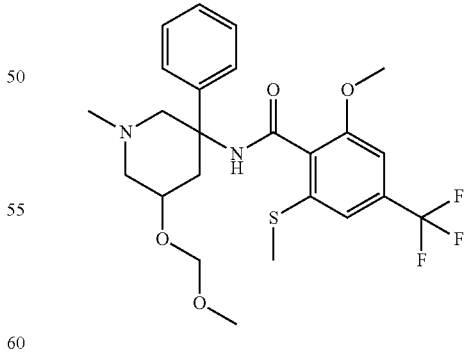

In analogy to the procedure described for the synthesis of example 16, the title compound was prepared from rac-5-methoxymethoxy-1-methyl-3-phenyl-piperidin-3-ylamine (Example A.10) and 2-methoxy-6-methylsulfanyl-4-trifluoromethyl-benzoyl chloride (Example B.6).
MS (m/e): 499.3 (MH+).

b) step 2: rac-N-(5-Hydroxy-1-methyl-3-phenyl-piperidin-3-yl)-2-methoxy-6-methylsulfanyl-4-trifluoromethyl-benzamide To a solution of 17 mg (0.0341 mmol) rac-2-methoxy-N-(5-methoxymethoxy-1-methyl-3-phenyl-piperidin-3-yl)-6-methylsulfanyl-4-trifluoromethyl-benzamide in 0.5 ml methanol were added 102 ul (0.102 mmol) of an aqueous 1N HCl solution. The mixture was stirred at room temperature for 30 minutes and then in a 65° C. oil bath for 24 hours. The solvent was removed in vacuo. The residue was taken in water. The aqueous layer was basified with a 2M Na₂CO₃ solution and extracted 3 times with dichloromethane. The combined extracts were dried over sodium sulfate, filtered and concentrated in vacuo. The crude product was purified on silica gel (Eluent: Heptane/ethyl acetate 0 to 100%) to provide 8 mg (52%) of the title compound as a white solid. MS (m/e): 455.2 (MH+).

Example 52 rac-2-Methoxy-N-[1-(2-methoxy-ethyl)-3-phenyl-piperidin-3-yl]-6-methylsulfanyl-4-trifluoromethyl-benzamide; hydrochloride

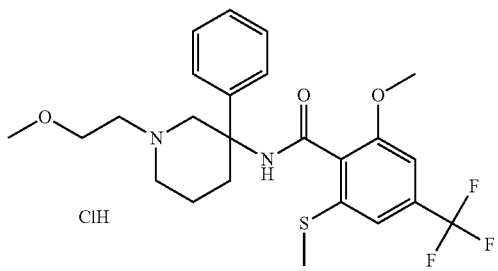 [SMILES: COCCN1CCCC(NC(=O)c2c(OC)cc(C(F)(F)F)cc2SC)(c2ccccc2)C1 ; Cl]

In analogy to the procedure described for the synthesis of example 30, the title compound was prepared from rac-2-methoxy-6-methylsulfanyl-N-(3-phenyl-piperidin-3-yl)-4-trifluoromethyl-benzamide hydrochloride (Example 50) and 2-bromoethyl methyl ether.
MS (m/e): 483.2 (MH+).

Example 53 rac-N-[1-(2-Hydroxy-ethyl)-3-phenyl-piperidin-3-yl]-2-methoxy-6-methylsulfanyl-4-trifluoromethyl-benzamide; hydrochloride

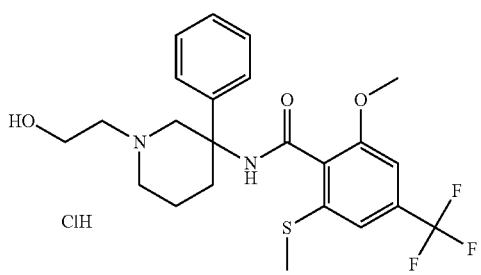 [SMILES: COc1cc(C(F)(F)F)cc(SC)c1C(=O)NC1(c2ccccc2)CCCN(CCO)C1 ; Cl]

In analogy to the procedure described for the synthesis of example 30, the title compound was prepared from rac-2-methoxy-6-methylsulfanyl-N-(3-phenyl-piperidin-3-yl)-4-trifluoromethyl-benzamide hydrochloride (Example 50) and 2-iodoethanol. MS (m/e): 469.2 (MH+).

Example 54 rac-N-(1-Cyclobutyl-3-phenyl-piperidin-3-yl)-2-methoxy-6-methylsulfanyl-4-trifluoromethyl-benzamide; hydrochloride

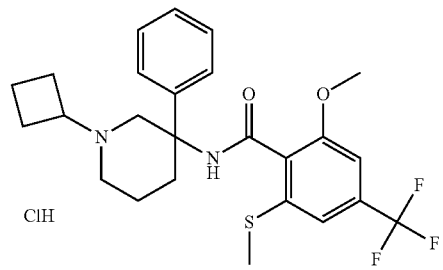 [SMILES: COc1cc(C(F)(F)F)cc(SC)c1C(=O)NC1(c2ccccc2)CCCN(C2CCC2)C1 ; Cl]

In analogy to the procedure described for the synthesis of example 31, the title compound was prepared from rac-2-methoxy-6-methylsulfanyl-N-(3-phenyl-piperidin-3-yl)-4-trifluoromethyl-benzamide hydrochloride (Example 50) and cyclobutanone. MS (m/e): 479.1 (MH+).

Example 55 rac-N-(1-Isopropyl-3-phenyl-piperidin-3-yl)-2-methoxy-6-methylsulfanyl-4-trifluoromethyl-benzamide; hydrochloride

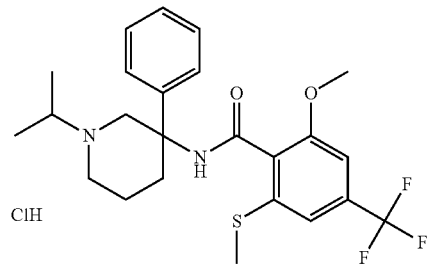 [SMILES: COc1cc(C(F)(F)F)cc(SC)c1C(=O)NC1(c2ccccc2)CCCN(C(C)C)C1 ; Cl]

In analogy to the procedure described for the synthesis of example 31, the title compound was prepared from rac-2-methoxy-6-methylsulfanyl-N-(3-phenyl-piperidin-3-yl)-4-trifluoromethyl-benzamide hydrochloride (Example 50) and acetone. MS (m/e): 467.2 (MH+).

The examples 56-57 have been prepared by separation of the racemic material by chiral HPLC followed by formation of the hydrochloride salt with HCl/Methanol:

| Ex. No. | Structure | Systematic Name | Starting racemic material | Retent. time (min.)* | MW found (MH+) |
|---|---|---|---|---|---|
| 56 | 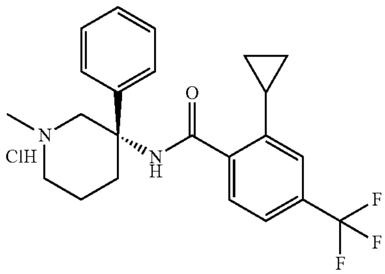 [SMILES: CN1CCC[C@](NC(=O)c2ccc(C(F)(F)F)cc2C2CC2)(c2ccccc2)C1 ; Cl] | 2-Cyclopropyl-N-((S)-1-methyl-3-phenyl-piperidin-3-yl)-4-trifluoromethyl-benzamide hydrochloride | rac-2-Cyclopropyl-N-(1-methyl-3-phenyl-piperidin-3-yl)-4-trifluoromethyl-benzamide (Example 13) | 5.6 | 403.3 |
| 57 | 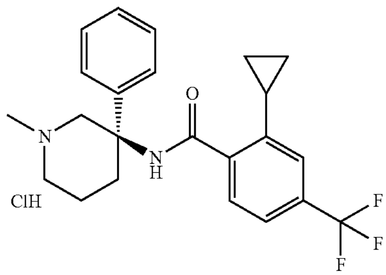 [SMILES: CN1CCC[C@@](NC(=O)c2ccc(C(F)(F)F)cc2C2CC2)(c2ccccc2)C1 ; Cl] | 2-Cyclopropyl-N-((R)-1-methyl-3-phenyl-piperidin-3-yl)-4-trifluoromethyl-benzamide hydrochloride | rac-2-Cyclopropyl-N-(1-methyl-3-phenyl-piperidin-3-yl)-4-trifluoromethyl-benzamide (Example 13) | 18.8 | 403.3 |

*Analytical separation conditions: Column: Chiralpak AD; Eluent: 15% Isopropanol/Heptane; flow 35 ml, UV detection: 254 nm

Example 58 rac-N-(3-Cyclohexyl-1-methyl-piperidin-3-yl)-2-methoxy-6-methylsulfanyl-4-trifluoromethyl-benzamide

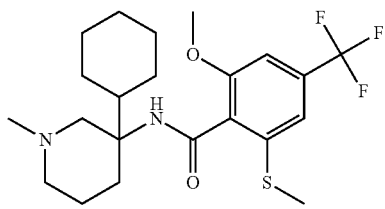 [SMILES: COc1cc(C(F)(F)F)cc(SC)c1C(=O)NC1(C2CCCCC2)CCCN(C)C1]

In analogy to the procedure described for the synthesis of example 16, the title compound was prepared from rac-3-cyclohexyl-1-methyl-piperidin-3-ylamine (Example A.11) and 2-methoxy-6-methylsulfanyl-4-trifluoromethyl-benzoyl chloride (Example B6). MS (m/e): 445.2 (MH+).

Example 59 rac-2-Methoxy-6-methylsulfanyl-N-[1-methyl-3-(tetrahydro-pyran-4-yl)-piperidin-3-yl]-4-trifluoromethyl-benzamide

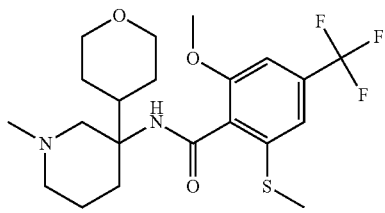 [SMILES: COc1cc(C(F)(F)F)cc(SC)c1C(=O)NC1(C2CCOCC2)CCCN(C)C1]

In analogy to the procedure described for the synthesis of example 16, the title compound was prepared from rac-1-methyl-3-(tetrahydro-pyran-4-yl)-piperidin-3-ylamine (Example A.12) and 2-methoxy-6-methylsulfanyl-4-trifluoromethyl-benzoyl chloride (Example B6). MS (m/e): 447.2 (MH+).

Example 60 rac-N-(1,3-Dimethyl-piperidin-3-yl)-2-methoxy-6-methylsulfanyl-4-trifluoromethyl-benzamide

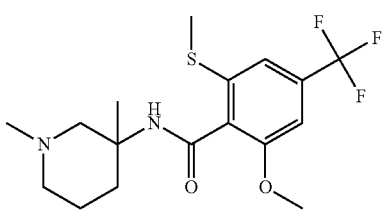 [SMILES: COc1cc(C(F)(F)F)cc(SC)c1C(=O)NC1(C)CCCN(C)C1]

In analogy to the procedure described for the synthesis of example 16, the title compound was prepared from rac-1,3-dimethyl-piperidin-3-ylamine dihydrochloride (Example A.13) and 2-methoxy-6-methylsulfanyl-4-trifluoromethyl-benzoyl chloride (Example B6). MS (m/e): 377.3 (MH+).

The examples 61-62 have been prepared by separation of the racemic material by chiral HPLC:

| Ex. No. | Structure | Systematic Name | Starting racemic material | Retent. time (min)* | MW found (MH+) |
|---|---|---|---|---|---|
| 61 | 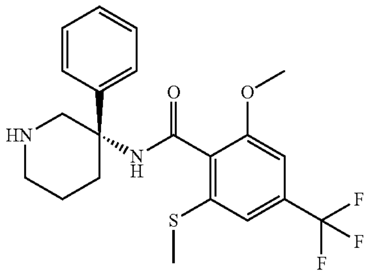 [SMILES: COc1cc(C(F)(F)F)cc(SC)c1C(=O)N[C@]1(c2ccccc2)CCCNC1] | 2-Methoxy-6-methylsulfanyl-N-((S) or (R)-3-phenyl-piperidin-3-yl)-4-trifluoromethyl-benzamide | rac-2-Methoxy-6-methylsulfanyl-N-(3-phenyl-piperidin-3-yl)-4-trifluoromethyl-benzamide (Example 50) | 11.0 | 425.1 |
| 62 | 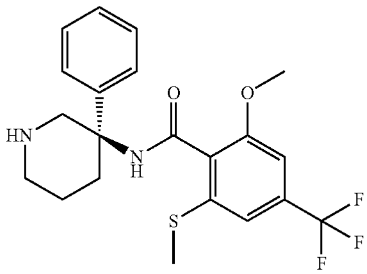 [SMILES: COc1cc(C(F)(F)F)cc(SC)c1C(=O)N[C@@]1(c2ccccc2)CCCNC1] | 2-Methoxy-6-methylsulfanyl-N-((R) or (S)-3-phenyl-piperidin-3-yl)-4-trifluoromethyl-benzamide | rac-2-Methoxy-6-methylsulfanyl-N-(3-phenyl-piperidin-3-yl)-4-trifluoromethyl-benzamide (Example 50) | 13.5 | 425.1 |

*Analytical separation conditions: Column: Chiralpak AD; Eluent: 15% Isopropanol/Heptane;

Example 63

[2H-methyl]-2-Methoxy-N—(R) or (S)-1-methyl-3-phenyl-piperidin-3-yl)-6-methylsulfanyl-4-trifluoromethyl-benzamide hydrochloride

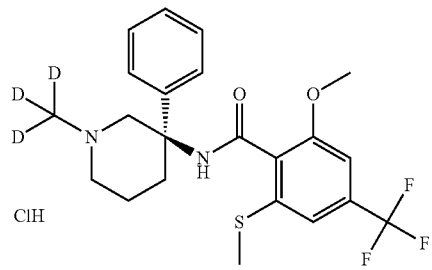 [SMILES: [2H]C([2H])([2H])N1CCC[C@@](NC(=O)c2c(OC)cc(C(F)(F)F)cc2SC)(c2ccccc2)C1 ; Cl]

In analogy to the procedure described for the synthesis of example 30, the title compound was prepared from 2-Methoxy-6-methylsulfanyl-N—((R) or (S)-3-phenyl-piperidin-3-yl)-4-trifluoromethyl-benzamide (Example 62) and tri-deuteromethyl iodide. MS (m/e): 442.3 (MH+).

Example 64 rac-2-Methoxy-6-methylsulfanyl-N-(1-oxetan-3-yl-3-phenyl-piperidin-3-yl)-4-trifluoromethyl-benzamide hydrochloride

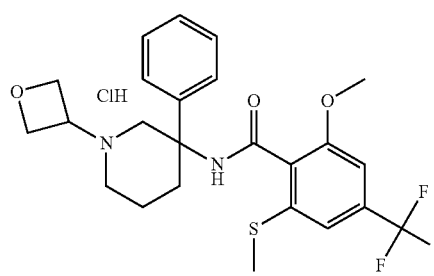

In analogy to the procedure described for the synthesis of example 31, the title compound was prepared from rac-2-methoxy-6-methylsulfanyl-N-(3-phenyl-piperidin-3-yl)-4-trifluoromethyl-benzamide hydrochloride (Example 50) and oxetanone. MS (m/e): 481.1 (MH+).

Example 65

N-((3RS,5RS)-5-Hydroxy-1-methyl-3-phenyl-piperidin-3-yl)-2-methoxy-6-methylsulfanyl-4-trifluoromethyl-benzamide

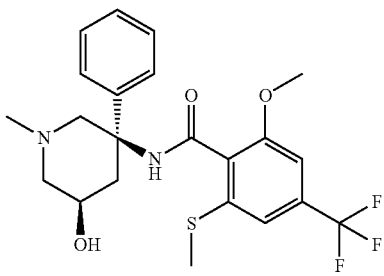 [SMILES: COc1cc(C(F)(F)F)cc(SC)c1C(=O)N[C@@]1(c2ccccc2)C[C@@H](O)CN(C)C1]

a) step 1: rac-2-Methoxy-N-(1-methyl-5-oxo-3-phenyl-piperidin-3-yl)-6-methylsulfanyl-4-trifluoromethyl-benzamide

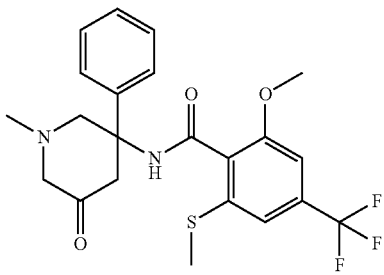 [SMILES: COc1cc(C(F)(F)F)cc(SC)c1C(=O)NC1(c2ccccc2)CC(=O)CN(C)C1]

To a −50° C. solution of 11 ul (0.21 mmol) oxalyl chloride in 0.8 ml dichloromethane was added a solution of 17.2 ul DMSO in 0.2 ml dichloromethane over a period of 15 minutes. The reaction mixture was stirred for 10 minutes, after which a solution of 50 mg (0.11 mmol) rac-N-(5-hydroxy-1-methyl-3-phenyl-piperidin-3-yl)-2-methoxy-6-methylsulfanyl-4-trifluoromethyl-benzamide (example 51) in 0.8 ml dichloromethane was added over a period of 15 minutes. After 30 min stirring, 77 ul (0.55 mmol) triethylamine was added. The reaction mixture was stirred for 15 minutes, then allowed to warm to room temperature and quenched with water and the aqueous layer was extracted with dichloromethane. The combined extracts were dried over sodium sulfate, filtered and concentrated in vacuo. The crude product was purified on silica gel (Eluent: Heptane/ethyl acetate 0 to 15%) to provide 44 mg (89%) of the title compound as a white foam. MS (m/e): 453.1 (MH+).

b) step 2: N-((3RS,5RS)-5-Hydroxy-1-methyl-3-phenyl-piperidin-3-yl)-2-methoxy-6 methylsulfanyl-4-trifluoromethyl-benzamide To a solution of 23 mg (0.0508 mmol) rac-2-methoxy-N-(1-methyl-5-oxo-3-phenyl-piperidin-3-yl)-6-methylsulfanyl-4-trifluoromethyl-benzamide in 0.46 ml methanol was added 3.9 mg (0.102 mmol) sodium borohydride. The mixture was stirred at room temperature for 30 minutes, quenched with 1.0 ml HCl 1N and stirred for 15 minutes. Water was added and the mixture was basified with a 2M sodium carbonate solution. The mixture was extracted 3 times with dichloromethane. The combined extracts were dried over sodium sulfate, filtered and concentrated in vacuo. The crude product was purified on silica gel (Eluent: heptane/ethyl acetate 0 to 100%) to provide 4.5 mg (20%) of the title compound as a white solid. MS (m/e): 455.2 (MH+).

In analogy to Example 1, compounds 66 to 84 of the following table were prepared from the acid derivatives and piperidine derivatives:

| Ex No. | Structure | Systematic Name | Starting materials | MW found (MH+) |
|---|---|---|---|---|
| 66 | 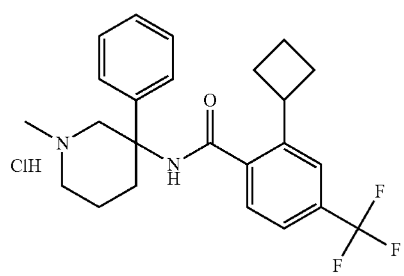 [SMILES: Cl ; CN1CCCC(NC(=O)c2ccc(C(F)(F)F)cc2C2CCC2)(c2ccccc2)C1] | rac-2-Cyclobutyl-N-(1-methyl-3-phenyl-piperidin-3-yl)-4-trifluoromethyl-benzamide hydrochloride | rac-1-Methyl-3-phenyl-piperidin-3-ylamine (Example A.1) and 2-Cyclobutyl-4-trifluoromethyl-benzoic acid (Example B.12) | 417.3 |
| 67 | 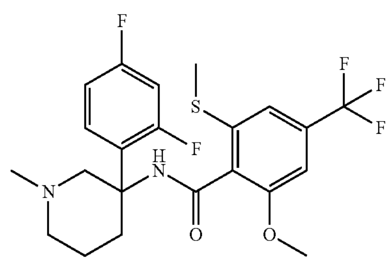 [SMILES: COc1cc(C(F)(F)F)cc(SC)c1C(=O)NC1(c2ccc(F)cc2F)CCCN(C)C1] | rac-N-[3-(2,4-Difluoro-phenyl)-1-methyl-piperidin-3-yl]-2-methoxy-6-methylsulfanyl-4-trifluoromethyl-benzamide | rac-3-(2,4-Difluorophenyl)-1-methyl-piperidin-3-ylamine (Example A.14) and 2-Methoxy-6-methylsulfanyl-4-trifluoromethyl-benzoic acid (Example B.2) | 475.5 |
| 68 | 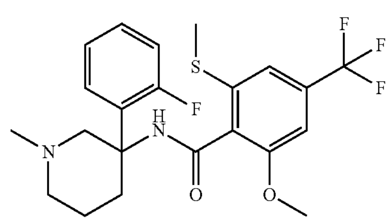 [SMILES: COc1cc(C(F)(F)F)cc(SC)c1C(=O)NC1(c2ccccc2F)CCCN(C)C1] | rac-N-[3-(2-Fluoro-phenyl)-1-methyl-piperidin-3-yl]-2-methoxy-6-methylsulfanyl-4-trifluoromethyl-benzamide | rac-3-(2-Fluoro-phenyl)-1-methyl-piperidin-3-ylamine (Example A.15) and 2-Methoxy-6-methylsulfanyl-4-trifluoromethyl-benzoic acid (Example B.2) | 457.6 |
| 69 | 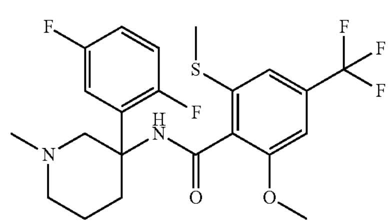 [SMILES: COc1cc(C(F)(F)F)cc(SC)c1C(=O)NC1(c2cc(F)ccc2F)CCCN(C)C1] | rac-N-[3-(2,5-Difluoro-phenyl)-1-methyl-piperidin-3-yl]-2-methoxy-6-methylsulfanyl-4-trifluoromethyl-benzamide | rac-3-(2,5-Difluoro-phenyl)-1-methyl-piperidin-3-ylamine (Example A.16) and 2-Methoxy-6-methylsulfanyl-4-trifluoromethyl-benzoic acid (Example B.2) | 475.5 |

-continued

| Ex No. | Structure | Systematic Name | Starting materials | MW found (MH+) |
|---|---|---|---|---|
| 70 | 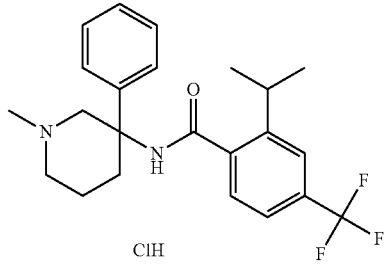 [SMILES: CC(C)c1cc(C(F)(F)F)ccc1C(=O)NC1(c2ccccc2)CCCN(C)C1 ; Cl] | rac-2-Isopropyl-N-(1-methyl-3-phenyl-piperidin-3-yl)-4-trifluoromethyl-benzamide hydrochloride | rac-1-Methyl-3-phenyl-piperidin-3-ylamine (Example A.1) and 2-Isopropyl-4-trifluoromethyl-benzoic acid (Example B.13) | 405.4 |
| 71 | 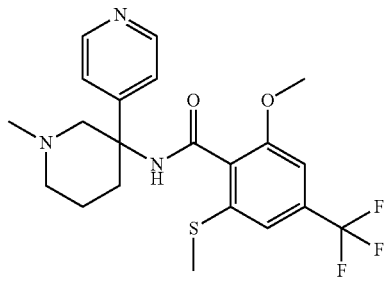 [SMILES: COc1cc(C(F)(F)F)cc(SC)c1C(=O)NC1(c2ccncc2)CCCN(C)C1] | rac-2-Methoxy-6-methylsulfanyl-N-(1-methyl-1,4,5,6-tetrahydro-2H-[3,4']bipyridinyl-3-yl)-4-trifluoromethyl-benzamide | rac-1-Methyl-1,4,5,6-tetrahydro-2H-[3,4']bipyridinyl-3-ylamine (Example A.17) and 2-Methoxy-6-methylsulfanyl-4-trifluoromethyl-benzoic acid (Example B.2) | 440.2 |
| 72 | 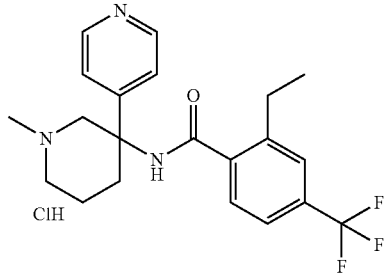 [SMILES: CCc1cc(C(F)(F)F)ccc1C(=O)NC1(c2ccncc2)CCCN(C)C1 ; Cl] | rac-2-Ethyl-N-(1-methyl-1,4,5,6-tetrahydro-2H-[3,4']bipyridinyl-3-yl)-4-trifluoromethyl-benzamide hydrochloride | rac-1-Methyl-1,4,5,6-tetrahydro-2H-[3,4']bipyridinyl-3-ylamine (Example A.17) and 2-Ethyl-4-trifluoromethyl-benzoic acid (CAS: 854531-63-8) | 392.2 |
| 73 | 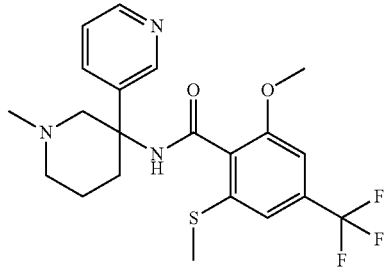 | rac-2-Methoxy-6-methylsulfanyl-N-(1-methyl-1,4,5,6-tetrahydro-2H-[3,3']bipyridinyl-3-yl)-4-trifluoromethyl-benzamide | rac-1-Methyl-1,4,5,6-tetrahydro-2H-[3,3']bipyridinyl-3-ylamine (Example A.18) and 2-Methoxy-6-methylsulfanyl-4-trifluoromethyl-benzoic acid (Example B.2) | 440.2 |
| 74 | 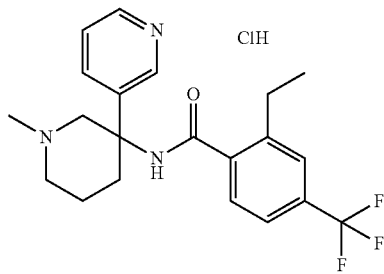 [SMILES: CCc1cc(C(F)(F)F)ccc1C(=O)NC1(c2cccnc2)CCCN(C)C1 ; Cl] | rac-2-Ethyl-N-(1-methyl-1,4,5,6-tetrahydro-2H-[3,3']bipyridinyl-3-yl)-4-trifluoromethyl-benzamide hydrochloride | rac-1-Methyl-1,4,5,6-tetrahydro-2H-[3,3']bipyridinyl-3-ylamine (Example A.18) and 2-Ethyl-4-trifluoromethyl-benzoic acid (CAS: 854531-63-8) | 392.2 |

| Ex No. | Structure | Systematic Name | Starting materials | MW found (MH+) |
|---|---|---|---|---|
| 75 | 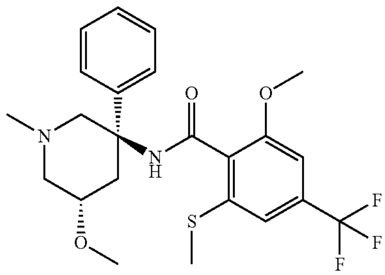 [SMILES: COc1cc(C(F)(F)F)cc(SC)c1C(=O)N[C@@]1(c2ccccc2)C[C@H](OC)CN(C)C1] | 2-Methoxy-N-((3RS,5SR)-5-methoxy-1-methyl-3-phenyl-piperidin-3-yl)-6-methylsulfanyl-4-trifluoromethyl-benzamide | (3RS,5SR)-5-Methoxy-1-methyl-3-phenyl-piperidin-3-ylamine (Example A.19) and 2-Methoxy-6-methylsulfanyl-4-trifluoromethyl-benzoic acid (Example B.2) | 469.2 |
| 76 | 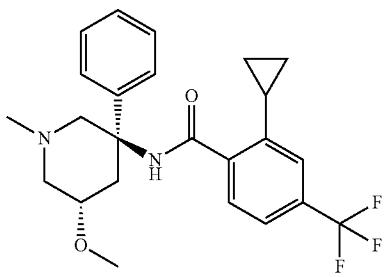 [SMILES: CO[C@@H]1CN(C)C[C@](NC(=O)c2ccc(C(F)(F)F)cc2C2CC2)(c2ccccc2)C1] | 2-Cyclopropyl-N-((3RS,5SR)-5-methoxy-1-methyl-3-phenyl-piperidin-3-yl)-4-trifluoromethyl-benzamide | (3RS,5SR)-5-Methoxy-1-methyl-3-phenyl-piperidin-3-ylamine (Example A.19) and 2-Cyclopropyl-4-trifluoromethyl-benzoic acid (Example B.3) | 433.4 |
| 77 | 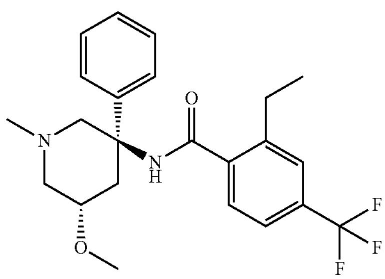 [SMILES: CCc1cc(C(F)(F)F)ccc1C(=O)N[C@@]1(c2ccccc2)C[C@H](OC)CN(C)C1] | 2-Ethyl-N-((3RS,5SR)-5-methoxy-1-methyl-3-phenyl-piperidin-3-yl)-4-trifluoromethyl-benzamide | (3RS,5SR)-5-Methoxy-1-methyl-3-phenyl-piperidin-3-ylamine (Example A.19) and 2-Ethyl-4-trifluoromethyl-benzoic acid (CAS: 854531-63-8) | 421.1 |
| 78 | 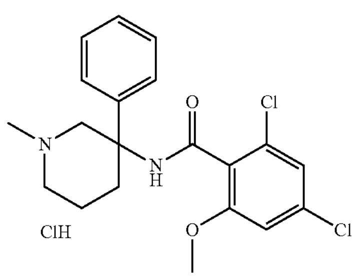 [SMILES: COc1cc(Cl)cc(Cl)c1C(=O)NC1(c2ccccc2)CCCN(C)C1 ; Cl] | rac-2,4-Dichloro-6-methoxy-N-(1-methyl-3-phenyl-piperidin-3-yl)-benzamide hydrochloride | rac-1-Methyl-3-phenyl-piperidin-3-ylamine (Example A.1) and 2,4-Dichloro-6-methoxy-benzoic acid (CAS: 92294-09-4) | 393 |
| 79 | 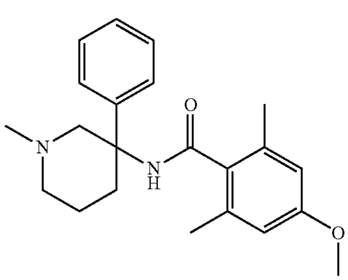 | rac-4-Methoxy-2,6-dimethyl-N-(1-methyl-3-phenyl-piperidin-3-yl)-benzamide | rac-1-Methyl-3-phenyl-piperidin-3-ylamine (Example A.1) and 4-Methoxy-2,6-dimethyl-benzoic acid (CAS: 37934-89-7) | 353.3 |

-continued

| Ex No. | Structure | Systematic Name | Starting materials | MW found (MH+) |
|---|---|---|---|---|
| 80 | 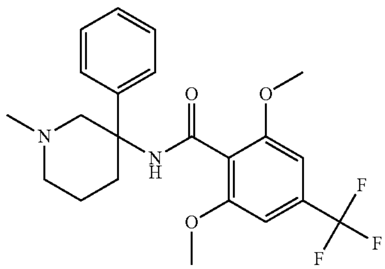 [SMILES: COc1cc(C(F)(F)F)cc(OC)c1C(=O)NC1(c2ccccc2)CCCN(C)C1] | rac-2,6-Dimethoxy-N-(1-methyl-3-phenyl-piperidin-3-yl)-4-trifluoromethyl-benzamide | rac-1-Methyl-3-phenyl-piperidin-3-ylamine (Example A.1) and 2,6-Dimethoxy-4-trifluoromethyl-benzoic acid (Example B.14) | 423.2 |
| 81 | 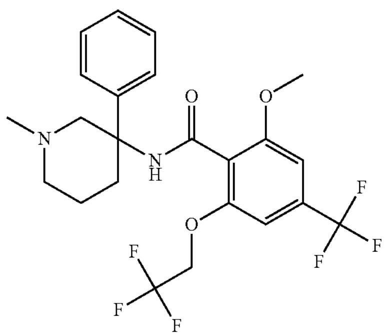 [SMILES: COc1cc(C(F)(F)F)cc(OCC(F)(F)F)c1C(=O)NC1(c2ccccc2)CCCN(C)C1] | rac-2-Methoxy-N-(1-methyl-3-phenyl-piperidin-3-yl)-6-(2,2,2-trifluoro-ethoxy)-4-trifluoromethyl-benzamide | rac-1-Methyl-3-phenyl-piperidin-3-ylamine (Example A.1) and 2-Methoxy-6-(2,2,2-trifluoro-ethoxy)-4-trifluoromethyl-benzoic acid (Example B.15) | 491.2 |
| 82 | 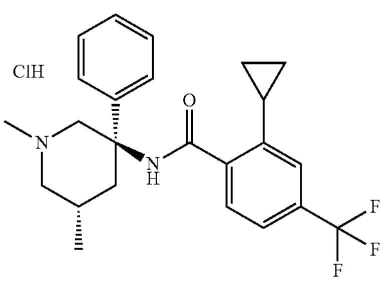 [SMILES: C[C@@H]1CN(C)C[C@](NC(=O)c2ccc(C(F)(F)F)cc2C2CC2)(c2ccccc2)C1 ; Cl] | 2-Cyclopropyl-N-((3RS,5SR)-1,5-dimethyl-3-phenyl-piperidin-3-yl)-4-trifluoromethyl-benzamide hydrochloride | (3RS,5SR)-1,5-Dimethyl-3-phenyl-piperidin-3-ylamine (Example A.20) and 2-Cyclopropyl-4-trifluoromethyl-benzoic acid (Example B.3) | 417.3 |
| 83 | 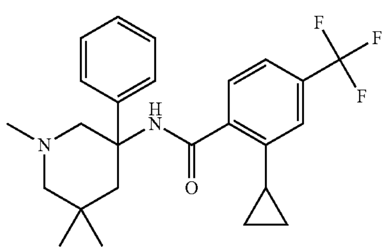 [SMILES: CN1CC(C)(C)CC(NC(=O)c2ccc(C(F)(F)F)cc2C2CC2)(c2ccccc2)C1] | rac-2-Cyclopropyl-4-trifluoromethyl-N-(1,5,5-trimethyl-3-phenyl-piperidin-3-yl)-benzamide | rac-1,5,5-Trimethyl-3-phenyl-piperidin-3-ylamine (Example A.21) and 2-Cyclopropyl-4-trifluoromethyl-benzoic acid (Example B.3) | 431.3 |
| 84 | 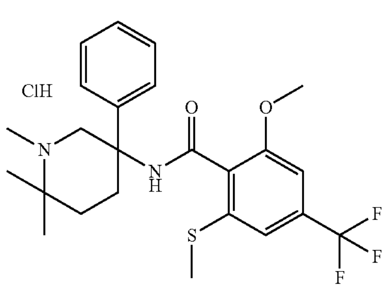 [SMILES: COc1cc(C(F)(F)F)cc(SC)c1C(=O)NC1(c2ccccc2)CCC(C)(C)N(C)C1 ; Cl] | rac-2-Methoxy-6-methylsulfanyl-4-trifluoromethyl-N-(1,6,6-trimethyl-3-phenyl-piperidin-3-yl)-benzamide hydrochloride | rac-1,6,6-Trimethyl-3-phenyl-piperidin-3-ylamine (Example A.22) and 2-Methoxy-6-methylsulfanyl-4-trifluoromethyl-benzoic acid (Example B.2) | 467.2 |

In analogy to Example 16, compounds 85 to 105 of the following table were prepared from the acyl chloride derivatives and piperidine derivatives:

| Ex. No. | Structure | Systematic Name | Starting materials | MW found (MH+) |
|---|---|---|---|---|
| 85 | 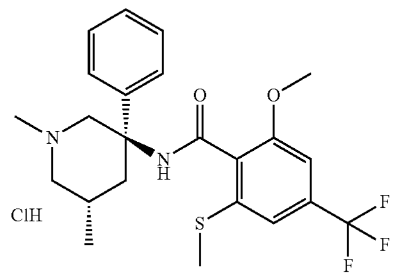 [SMILES: COc1cc(C(F)(F)F)cc(SC)c1C(=O)N[C@@]1(c2ccccc2)C[C@H](C)CN(C)C1 ; Cl] | N-((3R,5SR)-1,5-Dimethyl-3-phenyl-piperidin-3-yl)-2-methoxy-6-methylsulfanyl-4-trifluoromethyl-benzamide hydrochloride | (3RS,5SR)-1,5-Dimethyl-3-phenyl-piperidin-3-ylamine (Example A.20) and 2-Methoxy-6-methylsulfanyl-4-trifluoromethyl-benzoyl chloride (Example B6) | 453.5 |
| 86 | 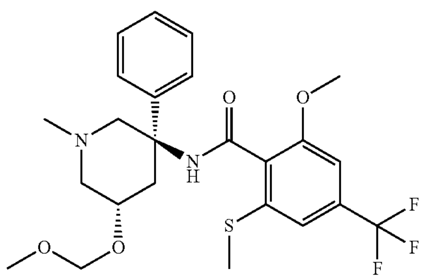 [SMILES: COCO[C@@H]1CN(C)C[C@](NC(=O)c2c(OC)cc(C(F)(F)F)cc2SC)(c2ccccc2)C1] | 2-Methoxy-N-((3RS,5SR)-5-methoxymethoxy-1-methyl-3-phenyl-piperidin-3-yl)-6-methylsulfanyl-4-trifluoromethyl-benzamide | rac-5-Methoxymethoxy-1-methyl-3-phenyl-piperidin-3-ylamine (Example A.10) and 2-Methoxy-6-methylsulfanyl-4-trifluoromethyl-benzoyl chloride (Example B6) | 499.3 |
| 87 | 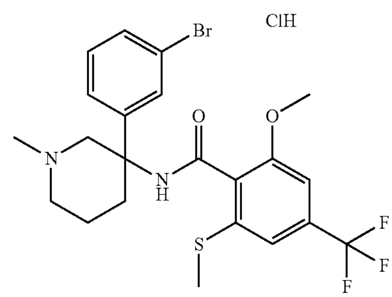 [SMILES: Cl ; COc1cc(C(F)(F)F)cc(SC)c1C(=O)NC1(c2cccc(Br)c2)CCCN(C)C1] | rac-N-[3-(3-Bromo-phenyl)-1-methyl-piperidin-3-yl]-2-methoxy-6-methylsulfanyl-4-trifluoromethyl-benzamide hydrochloride | rac-3-(3-Bromo-phenyl)-1-methyl-piperidin-3-ylamine (Example A.23) and 2-Methoxy-6-methylsulfanyl-4-trifluoromethyl-benzoyl chloride (Example B6) | 517.2 |
| 88 | 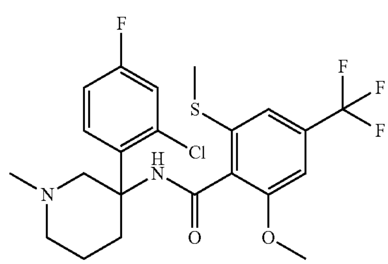 [SMILES: COc1cc(C(F)(F)F)cc(SC)c1C(=O)NC1(c2ccc(F)cc2Cl)CCCN(C)C1] | rac-N-[3-(2-Chloro-4-fluoro-phenyl)-1-methyl-piperidin-3-yl]-2-methoxy-6-methylsulfanyl-4-trifluoromethyl-benzamide | rac-3-(2-Chloro-4-fluoro-phenyl)-1-methyl-piperidin-3-ylamine (Example A.24) and 2-Methoxy-6-methylsulfanyl-4-trifluoromethyl-benzoyl chloride (Example B6) | 491.1 |
| 89 | 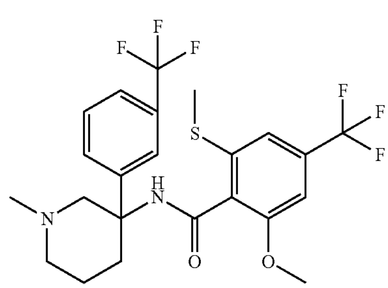 [SMILES: COc1cc(C(F)(F)F)cc(SC)c1C(=O)NC1(c2cccc(C(F)(F)F)c2)CCCN(C)C1] | rac-2-Methoxy-6-methylsulfanyl-N-[1-methyl-3-(3-trifluoromethyl-phenyl)-piperidin-3-yl]-4-trifluoromethyl-benzamide | rac-1-Methyl-3-(3-trifluoromethyl-phenyl)-piperidin-3-ylamine (Example A.26) and 2-Methoxy-6-methylsulfanyl-4-trifluoromethyl-benzoyl chloride (Example B6) | 507.2 |

| Ex. No. | Structure | Systematic Name | Starting materials | MW found (MH+) |
|---|---|---|---|---|
| 90 | 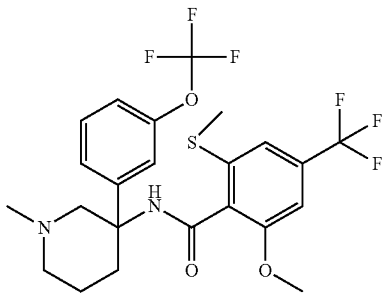 [SMILES: COc1cc(C(F)(F)F)cc(SC)c1C(=O)NC1(c2cccc(OC(F)(F)F)c2)CCCN(C)C1] | rac-2-Methoxy-6-methylsulfanyl-N-[1-methyl-3-(3-trifluoromethoxy-phenyl)-piperidin-3-yl]-4-trifluoromethyl-benzamide | rac-1-Methyl-3-(3-trifluoromethoxy-phenyl)-piperidin-3-ylamine (Example A.27) and 2-Methoxy-6-methylsulfanyl-4-trifluoromethyl-benzoyl chloride (Example B6) | 523.1 |
| 91 | 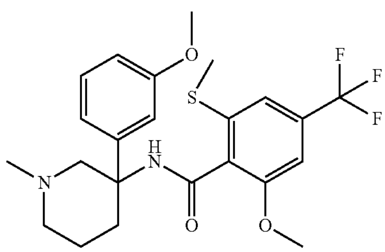 [SMILES: COc1cccc(C2(NC(=O)c3c(OC)cc(C(F)(F)F)cc3SC)CCCN(C)C2)c1] | rac-2-Methoxy-N-[3-(3-methoxy-phenyl)-1-methyl-piperidin-3-yl]-6-methylsulfanyl-4-trifluoromethyl-benzamide | rac-3-(3-Methoxy-phenyl)-1-methyl-piperidin-3-ylamine (Example A.28) and 2-Methoxy-6-methylsulfanyl-4-trifluoromethyl-benzoyl chloride (Example B6) | 469.2 |
| 92 | 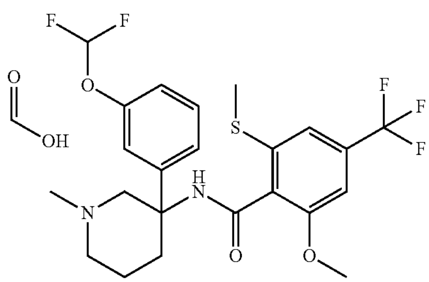 | rac-N-[3-(3-Difluoromethoxy-phenyl)-1-methyl-piperidin-3-yl]-2-methoxy-6-methylsulfanyl-4-trifluoromethyl-benzamide formic acid | rac-3-(3-Difluoromethoxy-phenyl)-1-methyl-piperidin-3-ylamine (Example A.29) and 2-Methoxy-6-methylsulfanyl-4-trifluoromethyl-benzoyl chloride (Example B6) | 505.2 |
| 93 | 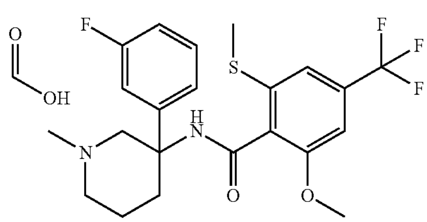 | rac-N-[3-(3-Fluoro-phenyl)-1-methyl-piperidin-3-yl]-2-methoxy-6-methylsulfanyl-4-trifluoromethyl-benzamide formic acid | rac-3-(3-Fluoro-phenyl)-1-methyl-piperidin-3-ylamine (Example A.30) and 2-Methoxy-6-methylsulfanyl-4-trifluoromethyl-benzoyl chloride (Example B6) | 457.2 |
| 94 | 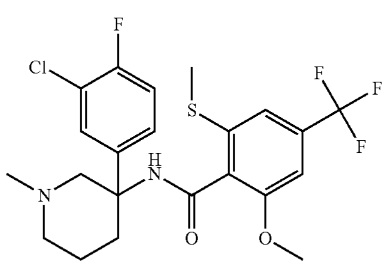 | rac-N-[3-(3-Chloro-4-fluoro-phenyl)-1-methyl-piperidin-3-yl]-2-methoxy-6-methylsulfanyl-4-trifluoromethyl-benzamide | rac-3-(3-Chloro-4-fluoro-phenyl)-1-methyl-piperidin-3-ylamine (Example A.31) and 2-Methoxy-6-methylsulfanyl-4-trifluoromethyl-benzoyl chloride (Example B6) | 491.1 |

-continued

| Ex. No. | Structure | Systematic Name | Starting materials | MW found (MH+) |
|---|---|---|---|---|
| 95 | 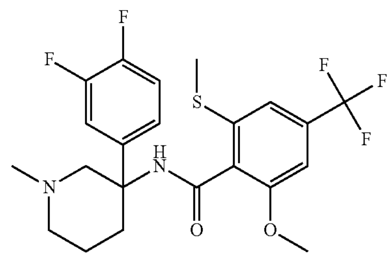 [SMILES: COc1cc(C(F)(F)F)cc(SC)c1C(=O)NC1(c2ccc(F)c(F)c2)CCCN(C)C1] | rac-N-[3-(3,4-Difluoro-phenyl)-1-methyl-piperidin-3-yl]-2-methoxy-6-methylsulfanyl-4-trifluoromethyl-benzamide | rac-3-(3,4-Difluoro-phenyl)-1-methyl-piperidin-3-ylamine (Example A.32) and 2-Methoxy-6-methylsulfanyl-4-trifluoromethyl-benzoyl chloride (Example B6) | 475.1 |
| 96 | 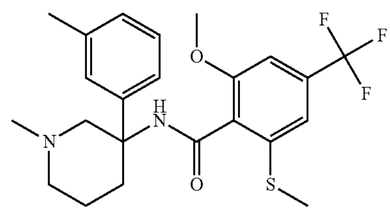 [SMILES: COc1cc(C(F)(F)F)cc(SC)c1C(=O)NC1(c2cccc(C)c2)CCCN(C)C1] | rac-2-Methoxy-6-methylsulfanyl-N-(1-methyl-3-m-tolyl-piperidin-3-yl)-4-trifluoromethyl-benzamide | rac-1-Methyl-3-m-tolyl-piperidin-3-ylamine (Example A.33) and 2-Methoxy-6-methysulfanyl-4-trifluoromethyl-benzoyl chloride Example B6) | 453.2 |
| 97 | 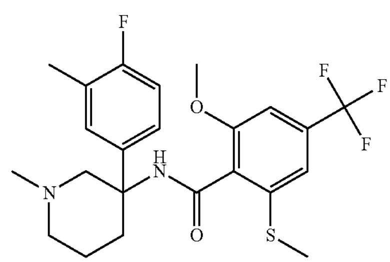 [SMILES: COc1cc(C(F)(F)F)cc(SC)c1C(=O)NC1(c2ccc(F)c(C)c2)CCCN(C)C1] | rac-N-[3-(4-Fluoro-3-methyl-phenyl)-1-methyl-piperidin-3-yl]-2-methoxy-6-methylsulfanyl-4-trifluoromethyl-benzamide | rac-3-(4-Fluoro-3-methyl-phenyl)-1-methyl-piperidin-3-ylamine (Example A.34) and 2-Methoxy-6-methylsulfanyl-4-trifluoromethyl-benzoyl chloride (Example B6) | 471.2 |
| 98 | 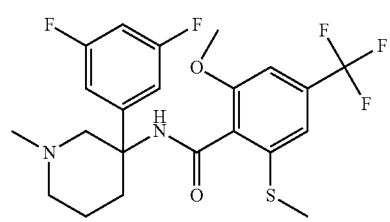 [SMILES: COc1cc(C(F)(F)F)cc(SC)c1C(=O)NC1(c2cc(F)cc(F)c2)CCCN(C)C1] | rac-N-[3-(3,5-Difluoro-phenyl)-1-methyl-piperidin-3-yl]-2-methoxy-6-methylsulfanyl-4-trifluoromethyl-benzamide | rac-3-(3,5-Difluoro-phenyl)-1-methyl-piperidin-3-ylamine (Example A.35) and 2-Methoxy-6-methylsulfanyl-4-trifluoromethyl-benzoyl chloride (Example B6) | 475.1 |
| 99 | 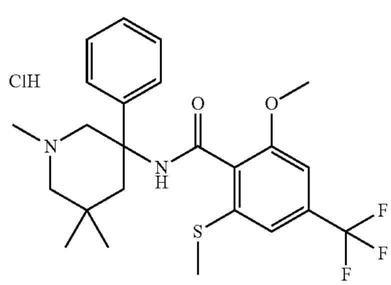 [SMILES: COc1cc(C(F)(F)F)cc(SC)c1C(=O)NC1(c2ccccc2)CN(C)CC(C)(C)C1 ; Cl] | rac-2-Methoxy-6-methylsulfanyl-4-trifluoromethyl-N-(1,5,5-trimethyl-3-phenyl-piperidin-3-yl)-benzamide hydrochloride | rac-1,5,5-Trimethyl-3-phenyl-piperidin-3-ylamine (Example A.21) and 2-Methxoy-6-methylsulfanyl-4-trifluoromethyl-benzoyl chloride (Example B6) | 467.2 |
| 100 | 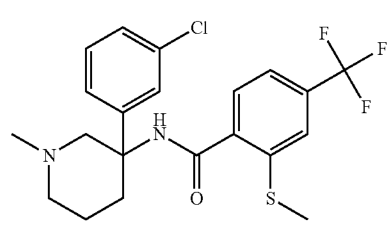 [SMILES: CSc1cc(C(F)(F)F)ccc1C(=O)NC1(c2cccc(Cl)c2)CCCN(C)C1] | rac-N-[3-(3-Chloro-phenyl)-1-methyl-piperidin-3-yl]-2-methylsulfanyl-4-trifluoromethyl-benzamide | rac-3-(3-Chloro-phenyl)-1-methyl-piperidin-3-ylamine (Example A.6) and 2-Methylsulfanyl-4-trifluoromethyl-benzoyl chloride (CAS: 956830-68-5) | 443.1 |

-continued

| Ex. No. | Structure | Systematic Name | Starting materials | MW found (MH+) |
|---|---|---|---|---|
| 101 | 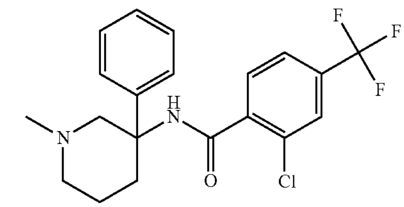 [SMILES: CN1CCCC(NC(=O)c2ccc(C(F)(F)F)cc2Cl)(c2ccccc2)C1] | rac-2-Chloro-N-(1-methyl-3-phenyl-piperidin-3-yl)-4-trifluoromethyl-benzamide | rac-1-Methyl-3-phenyl-piperidin-3-ylamine (Example A.1) and 2-Chloro-4-trifluoromethyl-benzoyl chloride (CAS: 76286-03-8) | 397.1 |
| 102 | 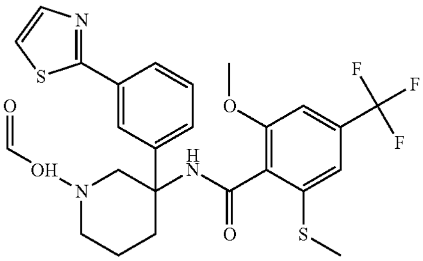 [SMILES: COc1cc(C(F)(F)F)cc(SC)c1C(=O)NC1(c2cccc(-c3nccs3)c2)CCCN(OC=O)C1] | rac-2-Methoxy-6-methylsulfanyl-N-[1-methyl-3-(3-thiazol-2-yl-phenyl)-piperidin-3-yl]-4-trifluoromethyl-benzamide formic acid | rac-1-Methyl-3-(3-thiazol-2-yl-phenyl)-piperidin-3-ylamine (Example A.36) and 2-Methoxy-6-methylsulfanyl-4-trifluoromethyl-benzoyl chloride (Example B6) | 522.1 |
| 103 | 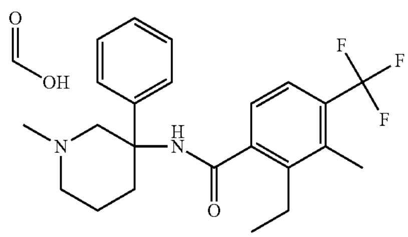 | rac-2-Ethyl-3-methyl-N-(1-methyl-3-phenyl-piperidin-3-yl)-4-trifluoromethyl-benzamide formic acid | rac-1-Methyl-3-phenyl-piperidin-3-ylamine (Example A.1) and 2-Ethyl-3-methyl-4-trifluoromethyl-benzoyl chloride (Example B.16) | 405.2 |
| 104 | 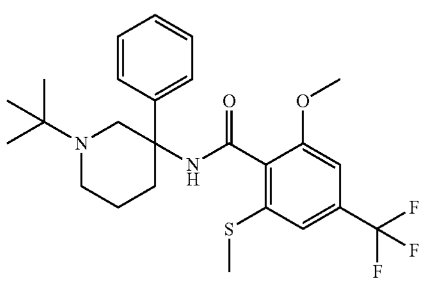 [SMILES: COc1cc(C(F)(F)F)cc(SC)c1C(=O)NC1(c2ccccc2)CCCN(C(C)(C)C)C1] | rac-N-(1-tert-Butyl-3-phenyl-piperidin-3-yl)-2-methoxy-6-methylsulfanyl-4-trifluoromethyl-benzamide | rac-1-tert-Butyl-3-phenyl-piperidin-3-ylamine (Example A.37) and 2-Methoxy-6-methylsulfanyl-4-trifluoromethyl-benzoyl chloride Example B6) | 481.2 |
| 105 | 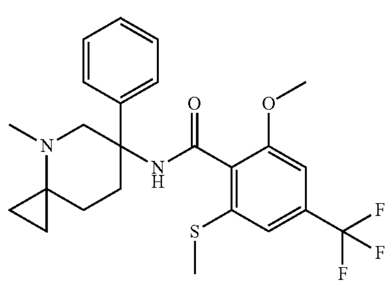 [SMILES: COc1cc(C(F)(F)F)cc(SC)c1C(=O)NC1(c2ccccc2)CCC2(CC2)N(C)C1] | rac-2-Methoxy-N-(4-methyl-6-phenyl-4-aza-spiro[2.5]oct-6-yl)-6-methylsulfanyl-4-trifluoromethyl-benzamide | rac-4-Methyl-6-phenyl-4-aza-spiro[2.5]oct-6-ylamine hydrochloride (Example A.38) and 2-Methoxy-6-methylsulfanyl-4-trifluoromethyl-benzoyl chloride (Example B6) | 465.2 |

The examples 106-128 have been prepared by separation of the racemic material by chiral HPLC:

| Ex. No. | Structure | Systematic Name | Starting racemic material | Col. type | Retent. time (min.)* | MW found (MH+) |
|---|---|---|---|---|---|---|
| 106 | 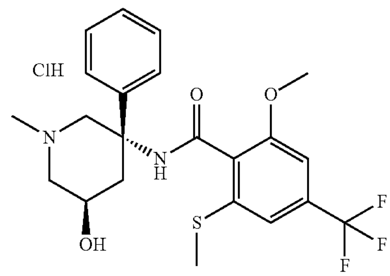 [SMILES: COc1cc(C(F)(F)F)cc(SC)c1C(=O)N[C@]1(c2ccccc2)C[C@@H](O)CN(C)C1 ; Cl] | N-((3S,5R) or (3R,5S)-5-Hydroxy-1-methyl-3-phenyl-piperidin-3-yl)-2-methoxy-6-methylsulfanyl-4-trifluoromethyl-benzamide hydrochloride | rac-N-(5-Hydroxy-1-methyl-3-phenyl-piperidin-3-yl)-2-methoxy-6-methylsulfanyl-4-trifluoromethyl-benzamide (Example 51) | A | 6.9 | 455.2 |
| 107 | 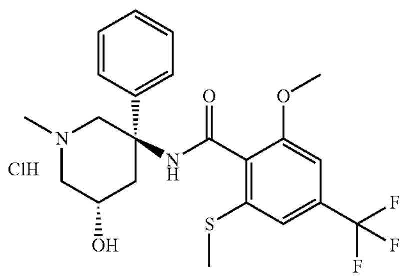 [SMILES: Cl ; COc1cc(C(F)(F)F)cc(SC)c1C(=O)N[C@@]1(c2ccccc2)C[C@H](O)CN(C)C1] | N-((3R,5S) or (3S,5R)-5-Hydroxy-1-methyl-3-phenyl-piperidin-3-yl)-2-methoxy-6-methylsulfanyl-4-trifluoromethyl-benzamide hydrochloride | rac-N-(5-Hydroxy-1-methyl-3-phenyl-piperidin-3-yl)-2-methoxy-6-methylsulfanyl-4-trifluoromethyl-benzamide (Example 51) | A | 10.2 | 455.2 |
| 108 | 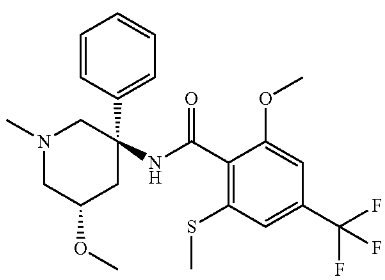 [SMILES: COc1cc(C(F)(F)F)cc(SC)c1C(=O)N[C@@]1(c2ccccc2)C[C@H](OC)CN(C)C1] | 2-Methoxy-N-((3R,5S) or (3S,5R)-5-methoxy-1-methyl-3-phenyl-piperidin-3-yl)-6-methylsulfanyl-4-trifluoromethyl-benzamide | 2-Methoxy-N-((3RS,5SR)-5-methoxy-1-methyl-3-phenyl-piperidin-3-yl)-6-methylsulfanyl-4-trifluoromethyl-benzamide (Example 75) | B | 22.7 | 469.2 |
| 109 | 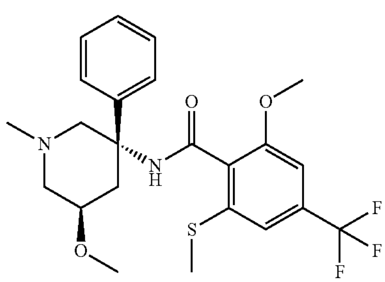 [SMILES: COc1cc(C(F)(F)F)cc(SC)c1C(=O)N[C@]1(c2ccccc2)C[C@@H](OC)CN(C)C1] | 2-Methoxy-N-((3S,5R) or (3R,5S)-5-methoxy-1-methyl-3-phenyl-piperidin-3-yl)-6-methylsulfanyl-4-trifluoromethyl-benzamide | 2-Methoxy-N-((3RS,5SR)-5-methoxy-1-methyl-3-phenyl-piperidin-3-yl)-6-methylsulfanyl-4-trifluoromethyl-benzamide (Example 75) | B | 31.4 | 469.2 |
| 110 | 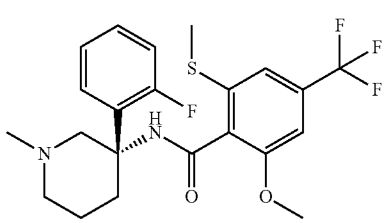 [SMILES: COc1cc(C(F)(F)F)cc(SC)c1C(=O)N[C@]1(c2ccccc2F)CCCN(C)C1] | N-[(S or R)-3-(2-Fluoro-phenyl)-1-methyl-piperidin-3-yl]-2-methoxy-6-methylsulfanyl-4-trifluoromethyl-benzamide | rac-N-[3-(2-Fluoro-phenyl)-1-methyl-piperidin-3-yl]-2-methoxy-6-methylsulfanyl-4-trifluoromethyl-benzamide (Example 68) | A | 8.0 | 457.2 |

-continued

| Ex. No. | Structure | Systematic Name | Starting racemic material | Col. type | Retent. time (min.)* | MW found (MH+) |
|---|---|---|---|---|---|---|
| 111 | 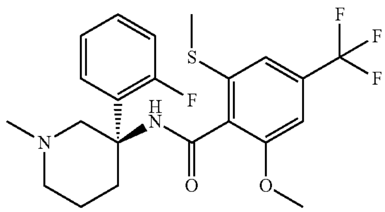 [SMILES: COc1cc(C(F)(F)F)cc(SC)c1C(=O)N[C@@]1(c2ccccc2F)CCCN(C)C1] | N-[(R or S)-3-(2-Fluoro-phenyl)-1-methyl-piperidin-3-yl]-2-methoxy-6-methylsulfanyl-4-trifluoromethyl-benzamide | rac-N-[3-(2-Fluoro-phenyl)-1-methyl-piperidin-3-yl]-2-methoxy-6-methylsulfanyl-4-trifluoromethyl-benzamide (Example 68) | A | 14.6 | 457.2 |
| 112 | 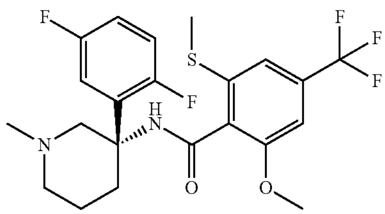 [SMILES: COc1cc(C(F)(F)F)cc(SC)c1C(=O)N[C@]1(c2cc(F)ccc2F)CCCN(C)C1] | N-[(S or R)-3-(2,5-Difluoro-phenyl)-1-methyl-piperidin-3-yl]-2-methoxy-6-methylsulfanyl-4-trifluoromethyl-benzamide | rac-N-[3-(2,5-Difluoro-phenyl)-1-methyl-piperidin-3-yl]-2-methoxy-6-methyl-sulfanyl-4-trifluoromethyl-benzamide (Example 69) | A | 14.6 | 475.1 |
| 113 | 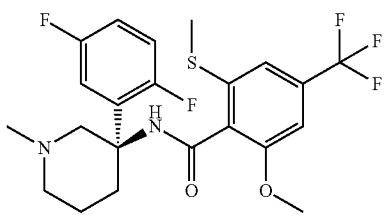 [SMILES: COc1cc(C(F)(F)F)cc(SC)c1C(=O)N[C@@]1(c2cc(F)ccc2F)CCCN(C)C1] | N-[(R or S)-3-(2,5-Difluoro-phenyl)-1-methyl-piperidin-3-yl]-2-methoxy-6-methylsulfanyl-4-trifluoromethyl-benzamide | rac-N-[3-(2,5-Difluoro-phenyl)-1-methyl-piperidin-3-yl]-2-methoxy-6-methylsulfanyl-4-trifluoro-methyl-benzamide (Example 69) | A | 15.8 | 475.1 |
| 114 | 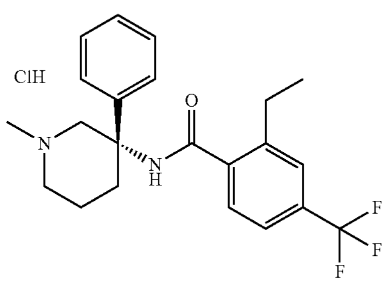 [SMILES: CCc1cc(C(F)(F)F)ccc1C(=O)N[C@]1(c2ccccc2)CCCN(C)C1 ; Cl] | 2-Ethyl-N-((S or R)-1-methyl-3-phenyl-piperidin-3-yl)-4-trifluoromethyl-benzamide hydrochloride | rac-2-Ethyl-N-(1-methyl-3-phenyl-piperidin-3-yl)-4-trifluoro-methyl-benzamide (Example 4) | A | 5.4 | 391.2 |
| 115 | 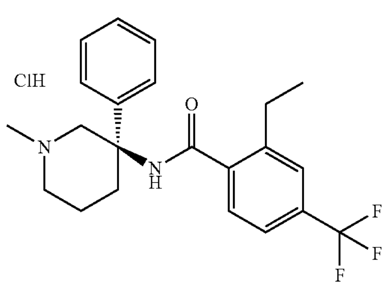 [SMILES: CCc1cc(C(F)(F)F)ccc1C(=O)N[C@@]1(c2ccccc2)CCCN(C)C1 ; Cl] | 2-Ethyl-N-((R or S)-1-methyl-3-phenyl-piperidin-3-yl)-4-trifluoromethyl-benzamide hydrochloride | rac-2-Ethyl-N-(1-methyl-3-phenyl-piperidin-3-yl)-4-trifluoro-methyl-benzamide (Example 4) | A | 9.9 | 391.1 |

| Ex. No. | Structure | Systematic Name | Starting racemic material | Col. type | Retent. time (min.)* | MW found (MH+) |
|---|---|---|---|---|---|---|
| 116 | 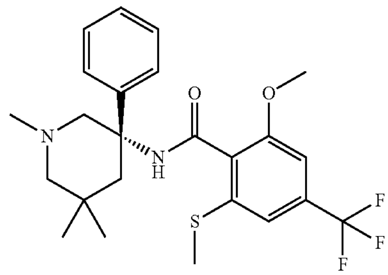 [SMILES: COc1cc(C(F)(F)F)cc(SC)c1C(=O)N[C@@]1(c2ccccc2)CN(C)CC(C)(C)C1] | 2-Methoxy-6-methylsulfanyl-4-trifluoromethyl-N-((S or R)-1,5,5-trimethyl-3-phenyl-piperidin-3-yl)-benzamide | rac-2-Methoxy-6-methylsulfanyl-4-trifluoromethyl-N-(1,5,5-trimethyl-3-phenyl-piperidin-3-yl)-benzamide hydrochloride (example 99) | C | 9.8 | 467.2 |
| 117 | 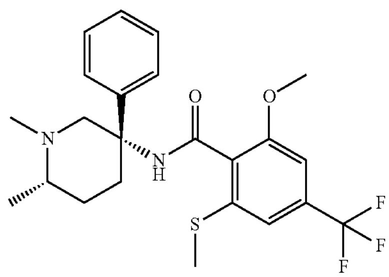 [SMILES: COc1cc(C(F)(F)F)cc(SC)c1C(=O)N[C@]1(c2ccccc2)CC[C@H](C)N(C)C1] | N-((3S,6S) or (3R,6R)-1,6-Dimethyl-3-phenyl-piperidin-3-yl)-2-methoxy-6-methylsulfanyl-4-trifluoromethyl-benzamide | N-(1,6-Dimethyl-3-phenyl-piperidin-3-yl)-2-methoxy-6-methylsulfanyl-4-trifluoromethyl-benzamide (Example C.1) | A | 7.5 | 453.2 |
| 118 | 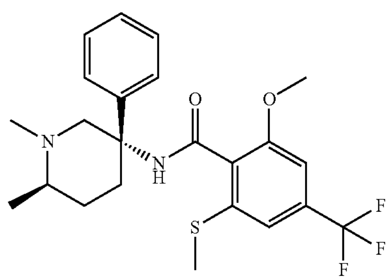 [SMILES: COc1cc(C(F)(F)F)cc(SC)c1C(=O)N[C@]1(c2ccccc2)CC[C@@H](C)N(C)C1] | N-((3S,6R) or (3R,6S)-1,6-Dimethyl-3-phenyl-piperidin-3-yl)-2-methoxy-6-methylsulfanyl-4-trifluoromethyl-benzamide | N-(1,6-Dimethyl-3-phenyl-piperidin-3-yl)-2-methoxy-6-methylsulfanyl-4-trifluoromethyl-benzamide (Example C.1) | A | 8.9 | 453.2 |
| 119 | 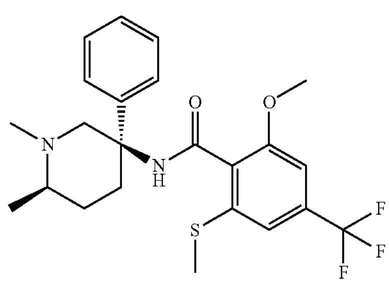 [SMILES: COc1cc(C(F)(F)F)cc(SC)c1C(=O)N[C@@]1(c2ccccc2)CC[C@@H](C)N(C)C1] | N-((3R,6R) or (3S,6S)-1,6-Dimethyl-3-phenyl-piperidin-3-yl)-2-methoxy-6-methylsulfanyl-4-trifluoromethyl-benzamide | N-(1,6-Dimethyl-3-phenyl-piperidin-3-yl)-2-methoxy-6-methylsulfanyl-4-trifluoromethyl-benzamide (Example C.1) | A | 10.8 | 453.2 |
| 120 | 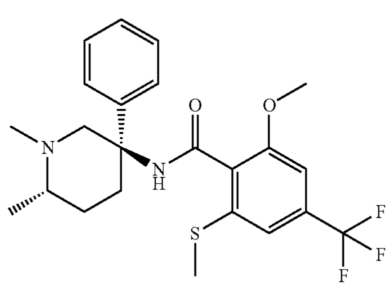 [SMILES: COc1cc(C(F)(F)F)cc(SC)c1C(=O)N[C@@]1(c2ccccc2)CC[C@H](C)N(C)C1] | N-((3R,6S) or (3S,6R)-1,6-Dimethyl-3-phenyl-piperidin-3-yl)-2-methoxy-6-methylsulfanyl-4-trifluoromethyl-benzamide | N-(1,6-Dimethyl-3-phenyl-piperidin-3-yl)-2-methoxy-6-methylsulfanyl-4-trifluoromethyl-benzamide (Example C.1) | A | 15.7 | 453.2 |

-continued

| Ex. No. | Structure | Systematic Name | Starting racemic material | Col. type | Retent. time (min.)* | MW found (MH+) |
|---|---|---|---|---|---|---|
| 121 | 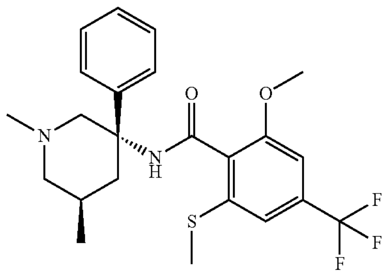 [SMILES: COc1cc(C(F)(F)F)cc(SC)c1C(=O)N[C@]1(c2ccccc2)C[C@@H](C)CN(C)C1] | N-((3S,5R) or (3R,5S)-1,5-Dimethyl-3-phenyl-piperidin-3-yl)-2-methoxy-6-methylsulfanyl-4-trifluoromethyl-benzamide | N-((3RS,5SR)-1,5-Dimethyl-3-phenyl-piperidin-3-yl)-2-methoxy-6-methylsulfanyl-4-trifluoro-methyl-benzamide hydrochloride (Example 85) | C | 14.4 | 453.2 |
| 122 | 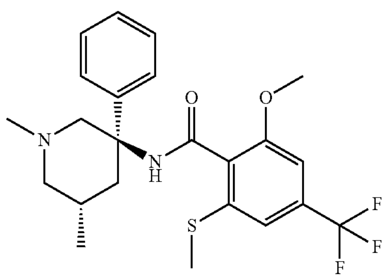 [SMILES: COc1cc(C(F)(F)F)cc(SC)c1C(=O)N[C@@]1(c2ccccc2)C[C@H](C)CN(C)C1] | N-((3R,5S) or (3S,5R)-1,5-Dimethyl-3-phenyl-piperidin-3-yl)-2-methoxy-6-methylsulfanyl-4-trifluoromethyl-benzamide | N-((3RS,5SR)-1,5-Dimethyl-3-phenyl-piperidin-3-yl)-2-methoxy-6-methylsulfanyl-4-trifluoro-methyl-benzamide hydrochloride (Example 85) | C | 17.7 | 453.2 |
| 123 | 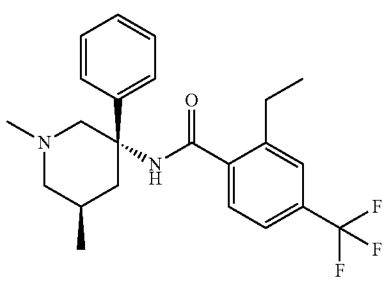 [SMILES: CCc1cc(C(F)(F)F)ccc1C(=O)N[C@]1(c2ccccc2)C[C@@H](C)CN(C)C1] | N-((3S,5R) or (3R,5S)-1,5-Dimethyl-3-phenyl-piperidin-3-yl)-2-ethyl-4-trifluoromethyl-benzamide | N-((3RS,5SR)-1,5-Dimethyl-3-phenyl-piperidin-3-yl)-2-ethyl-4-trifluoromethyl-benzamide (Example C.2) | A | 5.6 | 405.2 |
| 124 | 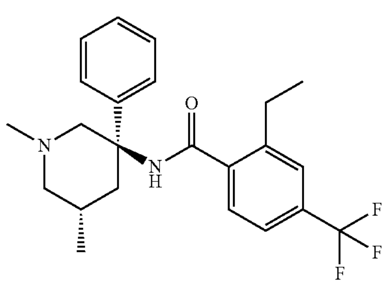 [SMILES: CCc1cc(C(F)(F)F)ccc1C(=O)N[C@@]1(c2ccccc2)C[C@H](C)CN(C)C1] | N-((3R,5S) or (3S,5R)-1,5-Dimethyl-3-phenyl-piperidin-3-yl)-2-ethyl-4-trifluoromethyl-benzamide | N-((3RS,5SR)-1,5-Dimethyl-3-phenyl-piperidin-3-yl)-2-ethyl-4-trifluoromethyl-benzamide (Example C.2) | A | 17.8 | 405.2 |
| 125 | 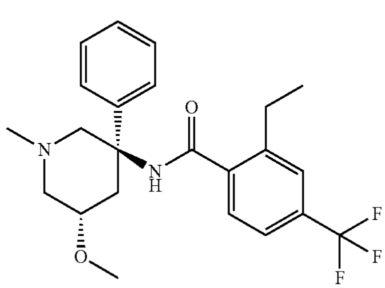 [SMILES: CCc1cc(C(F)(F)F)ccc1C(=O)N[C@@]1(c2ccccc2)C[C@H](OC)CN(C)C1] | 2-Ethyl-N-((3R,5S) or (3S,5R)-5-methoxy-1-methyl-3-phenyl-piperidin-3-yl)-4-trifluoromethyl-benzamide | 2-Ethyl-N-((3RS,5SR)-5-methoxy-1-methyl-3-phenyl-piperidin-3-yl)-4-trifluoro-methyl-benzamide (Example 77) | B | 7.1 | 421.2 |

-continued

| Ex. No. | Structure | Systematic Name | Starting racemic material | Col. type | Retent. time (min.)* | MW found (MH+) |
|---|---|---|---|---|---|---|
| 126 | 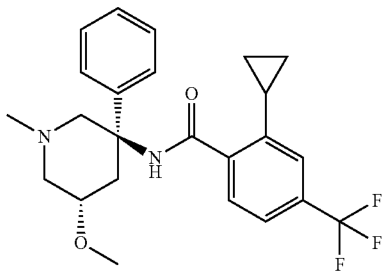 [SMILES: CO[C@@H]1CN(C)C[C@](NC(=O)c2ccc(C(F)(F)F)cc2C2CC2)(c2ccccc2)C1] | 2-Cyclopropyl-N-((3R,5S) or (3S,5R)-5-methoxy-1-methyl-3-phenyl-piperidin-3-yl)-4-trifluoromethyl-benzamide | 2-Cyclopropyl-N-((3RS,5SR)-5-methoxy-1-methyl-3-phenyl-piperidin-3-yl)-4-trifluoro-methyl-benzamide (Example 76) | C | 18 | 433.4 |
| 127 | 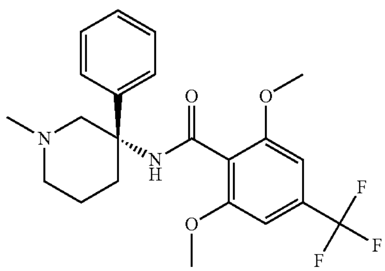 [SMILES: COc1cc(C(F)(F)F)cc(OC)c1C(=O)N[C@]1(c2ccccc2)CCCN(C)C1] | 2,6-Dimethoxy-N-((S) or (R)-1-methyl-3-phenyl-piperidin-3-yl)-4-trifluoromethyl-benzamide | rac-2,6-Dimethoxy-N-(1-methyl-3-phenyl-piperidin-3-yl)-4-trifluoro-methyl-benzamide (Example 80) | B | 9.7 | 423.2 |
| 128 | 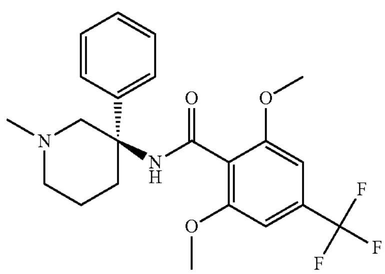 [SMILES: COc1cc(C(F)(F)F)cc(OC)c1C(=O)N[C@@]1(c2ccccc2)CCCN(C)C1] | 2,6-Dimethoxy-N-(R or (S)-1-methyl-3-phenyl-piperidin-3-yl)-4-trifluoromethyl-benzamide | rac-2,6-Dimethoxy-N-(1-methyl-3-phenyl-piperidin-3-yl)-4-trifluoro-methyl-benzamide (Example 80) | B | 20.7 | 423.2 |

*Analytical separation conditions: Column: A: Chiralpak AD; B: Lux 2 cellulose; C: Reprosil chiral NR. Eluent: 15% Isopropanol/Heptane;

The compounds of formula I and their pharmaceutically usable addition salts possess valuable pharmacological properties. Specifically, compounds of the present invention are good inhibitors of the glycine transporter I (GlyT-1). The compounds were investigated in accordance with the test given hereinafter.

Solutions and Materials

DMEM complete Medium:
Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies)

Uptake Buffer (UB):
150 mM NaCl, 10 mM Hepes-Tris, pH 7.4, 1 mM $CaCl_2$, 2.5 mM KCl, 2.5 mM $MgSO_4$, 10 mM (+) D-glucose.
Flp-in™-CHO (Invitrogen Cat n° R758-07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 µM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

The compounds described in examples 1-60 have an $IC_{50}$ data <1.0 µM. $IC_{50}$ data (<0.2 µM) for compounds 1-128 is provided in table 1.

TABLE 1

| Example | $IC_{50}$ data (µM) |
|---|---|
| 4 | 0.0264 |
| 5 | 0.1074 |
| 7 | 0.0854 |
| 11 | 0.0202 |
| 13 | 0.013 |
| 16 | 0.1379 |

TABLE 1-continued

| Example | IC$_{50}$ data (μM) |
|---|---|
| 18 | 0.0244 |
| 19 | 0.0672 |
| 25 | 0.1256 |
| 26 | 0.0593 |
| 27 | 0.0262 |
| 28 | 0.0277 |
| 36 | 0.0839 |
| 37 | 0.1817 |
| 38 | 0.0101 |
| 39 | 0.1843 |
| 45 | 0.0245 |
| 46 | 0.1693 |
| 47 | 0.1811 |
| 48 | 0.1973 |
| 51 | 0.0582 |
| 55 | 0.0777 |
| 56 | 0.1617 |
| 57 | 0.0227 |
| 58 | 0.1561 |
| 63 | 0.0100 |
| 66 | 0.243 |
| 67 | 0.1289 |
| 68 | 0.1746 |
| 69 | 0.1175 |
| 70 | 0.1973 |
| 71 | 0.0559 |
| 72 | 0.0369 |
| 73 | 0.0544 |
| 74 | 0.1226 |
| 75 | 0.0538 |
| 76 | 0.0929 |
| 77 | 0.0881 |
| 80 | 0.1759 |
| 82 | 0.0253 |
| 83 | 0.03 |
| 84 | 0.0173 |
| 85 | 0.0313 |
| 86 | 0.0715 |
| 87 | 0.0396 |
| 88 | 0.1457 |
| 89 | 0.107 |
| 91 | 0.1132 |
| 93 | 0.0479 |
| 94 | 0.0596 |
| 95 | 0.0515 |
| 96 | 0.0682 |
| 97 | 0.1851 |
| 98 | 0.0622 |
| 99 | 0.0366 |
| 103 | 0.0773 |
| 104 | 0.1734 |
| 105 | 0.0293 |
| 107 | 0.0312 |
| 108 | 0.0409 |
| 109 | 0.1507 |
| 111 | 0.0573 |
| 113 | 0.0564 |
| 115 | 0.0259 |
| 116 | 0.0358 |
| 117 | 0.0324 |
| 119 | 0.0139 |
| 120 | 0.0127 |
| 121 | 0.0165 |
| 124 | 0.0127 |
| 125 | 0.1761 |
| 126 | 0.0312 |
| 128 | 0.1255 |

The present invention also provides pharmaceutical compositions containing compounds of the invention, for example, compounds of formula I or pharmaceutically acceptable acid addition salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include disorders of the central nervous system, for example the treatment or prevention of schizophrenia, cognitive impairment and Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.

4. Add item 5 and mix for three minutes; compress on a suitable press.

Capsule Formulation

|      |                    | mg/capsule |       |        |        |
|------|--------------------|------|-------|--------|--------|
| Item | Ingredients        | 5 mg | 25 mg | 100 mg | 500 mg |
| 1.   | Compound of formula I | 5    | 25    | 100    | 500    |
| 2.   | Hydrous Lactose    | 159  | 123   | 148    | —      |
| 3.   | Corn Starch        | 25   | 35    | 40     | 70     |
| 4.   | Talc               | 10   | 15    | 10     | 25     |
| 5.   | Magnesium Stearate | 1    | 2     | 2      | 5      |
|      | Total              | 200  | 200   | 300    | 600    |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:
1. A compound of formula I

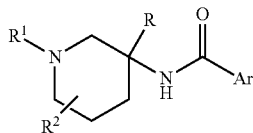

wherein
R$^1$ is hydrogen, lower alkyl, CD$_3$, —(CH$_2$)$_n$—CHO,— (CH$_2$)$_n$—O-lower alkyl,—(CH$_2$)$_n$—OH, —(CH$_2$)$_n$-cycloalkyl or heterocycloalkyl;
R$^2$ is hydrogen, halogen, hydroxy, lower alkyl, di-lower alkyl, —OCH$_2$—O-lower alkyl, or lower alkoxy; or the piperidin ring together with R$^2$ forms 4-aza-spiro[2.5]oct-6-yl;
Ar is phenyl substituted by one or two CF$_3$ groups and optionally substituted by one or two substituents selected from halogen, lower alkyl, lower alkyl substituted by halogen, lower alkoxy halogen, cycloalkyl, lower alkoxy, S-lower alkyl, heteroaryl, heterocycloalkyl, and phenyl optionally substituted by R', to give no more than three substituents total on Ar;
R' is lower alkyl, lower alkoxy, lower alkoxy substituted by halogen, or heteroaryl;
R is phenyl optionally substituted by one or two R'; and
n is 0, 1 2 or 3;
or a pharmaceutically acceptable acid addition salt, racemic mixture, enantiomer, or optical isomer thereof.
2. A compound of claim 1, wherein R$^1$ is lower alkyl.
3. A compound of claim 1, wherein the phenyl group for Ar is substituted by two CF$_3$ groups.
4. A compound of claim 1, selected from the group consisting of
rac-2-fluoro-N-(1-methyl-3-phenyl-piperidin-3-yl)-4,6-bis-trifluoromethyl-benzamide;
rac-2-methoxy-N-(1-methyl-3-phenyl-piperidin-3-yl)-4,6-bis-trifluoromethyl-benzamide;
rac-2-ethyl-N-(1-methyl-3-phenyl-piperidin-3-yl)-4,6-bis-trifluoromethyl-benzamide;
rac-N-[3-(4-fluoro-phenyl)-1-methyl-piperidin-3-yl]-2-methoxy-4,6-bis-trifluoromethyl-benzamide; and
2-methoxy-N-((R)-1-methyl-3-phenyl-piperidin-3-yl)-4,6-bis-trifluoromethyl-benzamide.
5. A compound of claim 1, selected from the group consisting of
rac-2-ethyl-N-(1-methyl-3-phenyl-piperidin-3-yl)-4-trifluoromethyl-benzamide;
rac-2-bromo-6-methoxy-N-(1-methyl-3-phenyl-piperidin-3-yl)-4-trifluoromethyl-benzamide;
rac-N-(1,2-dimethyl-3-phenyl-piperidin-3-yl)-2-methoxy-6-methylsulfanyl-4-trifluoromethyl-benzamide;
rac-2-cyclopropyl-N-(1-methyl-3-phenyl-piperidin-3-yl)-4-trifluoromethyl-benzamide;
rac-2-methoxy-N-(1-methyl-3-phenyl-piperidin-3-yl)-6-methylsulfanyl-4-trifluoromethyl-benzamide;
rac-N-(1-methyl-3-phenyl-piperidin-3-yl)-2-methylsulfanyl-4-trifluoromethyl-benzamide;
rac-N-[3-(4-fluoro-phenyl)-1-methyl-piperidin-3-yl]-2-methoxy-6-methyl sulfanyl-4-trifluoromethyl-benzamide;
rac-N-[3-(4-chloro-phenyl)-1-methyl-piperidin-3-yl]-2-methoxy-6-methylsulfanyl-4-trifluoromethyl-benzamide;
2-methoxy-N—((S)-1-methyl-3-phenyl-piperidin-3-yl)-6-methylsulfanyl-4-trifluoromethyl-benzamide;
2-methoxy-N-((R)-1-methyl-3-phenyl-piperidin-3-yl)-6-methylsulfanyl-4-trifluoromethyl-benzamide; and
rac-2-difluoromethoxy-N-(1-methyl-3-phenyl-piperidin-3-yl)-4-trifluoromethyl-benzamide.
6. A compound of claim 1, selected from the group consisting of
rac-N-[3-(3-chloro-phenyl)-1-methyl-piperidin-3-yl]-2-methoxy-6-methylsulfanyl-4-trifluoromethyl-benzamide;
rac-2-methoxy-N-[3-(4-methoxy-phenyl)-1-methyl-piperidin-3-yl]-6-methylsulfanyl-4-trifluoromethyl-benzamide;
rac-N-(5-fluoro-1-methyl-3-phenyl-piperidin-3-yl)-2-methoxy-6-methylsulfanyl-4-trifluoromethyl-benzamide;
rac-N-(1-isopropyl-3-phenyl-piperidin-3-yl)-2-methoxy-6-methylsulfanyl-4-trifluoromethyl-benzamide;
2-cyclopropyl-N—((S)-1-methyl-3-phenyl-piperidin-3-yl)-4-trifluoromethyl-benzamide;
2-cyclopropyl-N-((R)-1-methyl-3-phenyl-piperidin-3-yl)-4-trifluoromethyl-benzamide;
rac-2-cyclobutyl-N-(1-methyl-3-phenyl-piperidin-3-yl)-4-trifluoromethyl-benzamide;
rac-N-[3-(2,4-difluoro-phenyl)-1-methyl-piperidin-3-yl]-2-methoxy-6-methylsulfanyl-4-trifluoromethyl-benzamide;
rac-N-[3-(2-fluoro-phenyl)-1-methyl-piperidin-3-yl]-2-methoxy-6-methylsulfanyl-4-trifluoromethyl-benzamide;
rac-N-[3-(2,5-difluoro-phenyl)-1-methyl-piperidin-3-yl]-2-methoxy-6-methylsulfanyl-4-trifluoromethyl-benzamide; and
rac-2-isopropyl-N-(1-methyl-3-phenyl-piperidin-3-yl)-4-trifluoromethyl-benzamide.
7. A compound of claim 1, selected from the group consisting of
2-methoxy-N-((3RS,5 SR)-5-methoxy-1-methyl-3-phenyl-piperidin-3-yl)-6-methylsulfanyl-4-trifluoromethyl-benzamide;
2-cyclopropyl-N-((3 RS,5 SR)-5-methoxy-1-methyl-3-phenyl-piperidin-3-yl)-4-trifluoromethyl-benzamide;
2-ethyl-N-((3RS,5SR)-5-methoxy-1-methyl-3-phenyl-piperidin-3-yl)-4-trifluoromethyl-benzamide;

rac-2,6-dimethoxy-N-(1-methyl-3-phenyl-piperidin-3-yl)-4-trifluoromethyl-benzamide;
2-cyclopropyl-N-((3RS,5SR)-1,5-dimethyl-3-phenyl-piperidin-3-yl)-4-trifluoromethyl-benzamide;
rac-2-cyclopropyl-4-trifluoromethyl-N-(1,5,5-trimethyl-3-phenyl-piperidin-3-yl)-benzamide; and
rac-2-methoxy-6-methylsulfanyl-4-trifluoromethyl-N-(1,6,6-trimethyl-3-phenyl-piperidin-3-yl)-benzamide.

8. A compound of claim 1, selected from the group consisting of
N-((3RS,5SR)-1,5-dimethyl-3-phenyl-piperidin-3-yl)-2-methoxy-6-methylsulfanyl-4-trifluoromethyl-benzamide;
2-methoxy-N-((3RS,5SR)-5-methoxymethoxy-1-methyl-3-phenyl-piperidin-3-yl)-6-methylsulfanyl-4-trifluoromethyl-benzamide;
rac-N-[3-(3-bromo-phenyl)-1-methyl-piperidin-3-yl]-2-methoxy-6-methylsulfanyl-4-trifluoromethyl-benzamide;
rac-N-[3-(2-chloro-4-fluoro-phenyl)-1-methyl-piperidin-3-yl]-2-methoxy-6-methylsulfanyl-4-trifluoromethyl-benzamide;
rac-2-methoxy-6-methylsulfanyl-N-[1-methyl-3-(3-trifluoromethyl-phenyl)-piperidin-3-yl]-4-trifluoromethyl-benzamide;
rac-2-methoxy-N-[3-(3-methoxy-phenyl)-1-methyl-piperidin-3-yl]-6-methylsulfanyl-4-trifluoromethyl-benzamide;
rac-N-[3-(3-fluoro-phenyl)-1-methyl-piperidin-3-yl]-2-methoxy-6-methylsulfanyl-4-trifluoromethyl-benzamide;
rac-N-[3-(3-chloro-4-fluoro-phenyl)-1-methyl-piperidin-3-yl]-2-methoxy-6-methylsulfanyl-4-trifluoromethyl-benzamide;
rac-N-[3-(3,4-difluoro-phenyl)-1-methyl-piperidin-3-yl]-2-methoxy-6-methylsulfanyl-4-trifluoromethyl-benzamide; and
rac-2-methoxy-6-methylsulfanyl-N-(1-methyl-3-m-tolyl-piperidin-3-yl)-4-trifluoromethyl-benzamide.

9. A compound of claim 1, selected from the group consisting of
rac-N-[3-(4-fluoro-3-methyl-phenyl)-1-methyl-piperidin-3-yl]-2-methoxy-6-methylsulfanyl-4-trifluoromethyl-benzamide;
rac-N-[3-(3,5-difluoro-phenyl)-1-methyl-piperidin-3-yl]-2-methoxy-6-methylsulfanyl-4-trifluoromethyl-benzamide;
rac-2-methoxy-6-methylsulfanyl-4-trifluoromethyl-N-(1,5,5-trimethyl-3-phenyl-piperidin-3-yl)-benzamide;
rac-2-ethyl-3-methyl-N-(1-methyl-3-phenyl-piperidin-3-yl)-4-trifluoromethyl-benzamide;
rac-N-(1-tert-butyl-3-phenyl-piperidin-3-yl)-2-methoxy-6-methylsulfanyl-4-trifluoromethyl-benzamide;
rac-2-methoxy-N-(4-methyl-6-phenyl-4-aza-spiro[2.5]oct-6-yl)-6-methylsulfanyl-4-trifluoromethyl-benzamide;
N-((3R,5S) or (3S,5R)-5-hydroxy-1-methyl-3-phenyl-piperidin-3-yl)-2-methoxy-6-methylsulfanyl-4-trifluoromethyl-benzamide;
2-methoxy-N-((3R,5S) or (3S,5R)-5-methoxy-1-methyl-3-phenyl-piperidin-3-yl)-6-methylsulfanyl-4-trifluoromethyl-benzamide;
2-methoxy-N-((3S,5R) or (3R,5S)-5-methoxy-1-methyl-3-phenyl-piperidin-3-yl)-6-methylsulfanyl-4-trifluoromethyl-benzamide; and
N—[(R or S)-3-(2-fluoro-phenyl)-1-methyl-piperidin-3-yl]-2-methoxy-6-methylsulfanyl-4-trifluoromethyl-benzamide.

10. A compound of claim 1, selected from the group consisting of
N—[(R or S)-3-(2,5-difluoro-phenyl)-1-methyl-piperidin-3-yl]-2-methoxy-6-methylsulfanyl-4-trifluoromethyl-benzamide;
2-ethyl-N-((R or S)-1-methyl-3-phenyl-piperidin-3-yl)-4-trifluoromethyl-benzamide;
2-methoxy-6-methylsulfanyl-4-trifluoromethyl-N—((S or R)-1,5,5-trimethyl-3-phenyl-piperidin-3-yl)-benzamide;
N-((3S,6S) or (3R,6R)-1,6-dimethyl-3-phenyl-piperidin-3-yl)-2-methoxy-6-methylsulfanyl-4-trifluoromethyl-benzamide;
N-((3R,6R) or (3S,6S)-1,6-dimethyl-3-phenyl-piperidin-3-yl)-2-methoxy-6-methylsulfanyl-4-trifluoromethyl-benzamide;
N-((3R,6S) or (3S,6R)-1,6-dimethyl-3-phenyl-piperidin-3-yl)-2-methoxy-6-methylsulfanyl-4-trifluoromethyl-benzamide;
N-((3S,5R) or (3R,5S)-1,5-dimethyl-3-phenyl-piperidin-3-yl)-2-methoxy-6-methylsulfanyl-4-trifluoromethyl-benzamide;
N-((3R,5S) or (3S,5R)-1,5-dimethyl-3-phenyl-piperidin-3-yl)-2-ethyl-4-trifluoromethyl-benzamide;
2-ethyl-N-((3R,5S) or (3S,5R)-5-methoxy-1-methyl-3-phenyl-piperidin-3-yl)-4-trifluoromethyl-benzamide;
2-cyclopropyl-N-((3R,5S) or (3S,5R)-5-methoxy-1-methyl-3-phenyl-piperidin-3-yl)-4-trifluoromethyl-benzamide; and
2,6-Dimethoxy-N-(R or S)-1-methyl-3-phenyl-piperidin-3-yl)-4-trifluoromethyl-benzamide.

11. A compound of claim 1, wherein $R^1$ is cycloalkyl or heterocycloalkyl.

12. A compound of claim 11, selected from the group consisting of
rac-N-(1-cyclopentyl-3-phenyl-piperidin-3-yl)-2-methoxy-4,6-bis-trifluoromethyl-benzamide;
rac-N-(1-cyclopropylmethyl-3-phenyl-piperidin-3-yl)-2-methoxy-4,6-bis-trifluoromethyl-benzamide; and
rac-2-methoxy-N-[3-phenyl-1-(tetrahydro-pyran-4-yl)-piperidin-3-yl]-4,6-bis-trifluoromethyl-benzamide.

13. A compound of claim 1, wherein $R^1$ is hydrogen.

14. A compound of claim 13, wherein the compound is rac-2-cyclopropyl-N-(3-phenyl-piperidin-3-yl)-4-trifluoromethyl-benzamide.

15. A compound of claim 1, wherein $R^2$ is halogen.

16. A compound of claim 15, wherein the compound is rac-N-(5-fluoro-1-methyl-3-phenyl-piperidin-3-yl)-2-methoxy-6-methylsulfanyl-4-trifluoromethyl-benzamide.

17. A pharmaceutical composition comprising a therapeutically effective amount of a compound of formula I

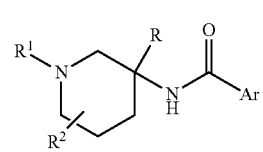

wherein
$R^1$ is hydrogen, lower alkyl, $CD_3$, —$(CH_2)_n$—CHO, —$(CH_2)_n$—O-lower alkyl, —$(CH_2)_n$—OH, —$(CH_2)_n$-cycloalkyl or heterocycloalkyl;

$R^2$ is hydrogen, halogen, hydroxy, lower alkyl, di-lower alkyl, —OCH$_2$—O-lower alkyl, or lower alkoxy; or the piperidin ring together with $R^2$ forms 4-aza-spiro[2.5]oct-6-yl;

Ar is phenyl substituted by one or two CF$_3$ groups and optionally substituted by one or two substituents selected from halogen, lower alkyl, lower alkyl substituted by halogen, lower alkoxy halogen, cycloalkyl, lower alkoxy, S-lower alkyl, heteroaryl, heterocycloalkyl, and phenyl optionally substituted by R', to give no more than three substituents total on Ar;

R' is lower alkyl, lower alkoxy, lower alkoxy substituted by halogen, or heteroaryl;

R is phenyl optionally substituted by one or two R'; and n is 0, 1 2 or 3;

or a pharmaceutically acceptable acid addition salt, racemic mixture, enantiomer, or optical isomer thereof and a pharmaceutically acceptable carrier.

\* \* \* \* \*